(12) United States Patent
Hwang et al.

(10) Patent No.: US 11,041,812 B2
(45) Date of Patent: Jun. 22, 2021

(54) FLUOROGENIC PH-SENSITIVE DYES, FILM AND KIT COMPRISING THE SAME

(71) Applicant: SFC CO., LTD., Chungcheongbuk-do (KR)

(72) Inventors: Moon-Chan Hwang, Gyeongsangnam-do (KR); Jong-Tae Je, Chungcheongbuk-do (KR)

(73) Assignee: SFC CO., LTD., Chungcheongbuk-do (KR)

( * ) Notice: Subject to any disclaimer, the term of this patent is extended or adjusted under 35 U.S.C. 154(b) by 537 days.

(21) Appl. No.: 15/870,146

(22) Filed: Jan. 12, 2018

(65) Prior Publication Data

US 2018/0231471 A1 Aug. 16, 2018

(30) Foreign Application Priority Data

Jan. 13, 2017 (KR) .......... 10-2017-0006461
Jan. 11, 2018 (KR) .......... 10-2018-0003690

(51) Int. Cl.

| G01N 21/00 | (2006.01) |
|---|---|
| G01N 21/80 | (2006.01) |
| C09B 49/10 | (2006.01) |
| C08L 5/12 | (2006.01) |
| C09B 11/02 | (2006.01) |
| G01N 33/84 | (2006.01) |
| C09B 67/02 | (2006.01) |
| C08B 37/00 | (2006.01) |
| C09B 5/62 | (2006.01) |
| C09B 23/14 | (2006.01) |
| C09B 57/00 | (2006.01) |
| C09B 57/02 | (2006.01) |
| G01N 31/22 | (2006.01) |
| G01N 33/58 | (2006.01) |

(52) U.S. Cl.
CPC .......... *G01N 21/80* (2013.01); *C08B 37/0039* (2013.01); *C08L 5/12* (2013.01); *C09B 5/62* (2013.01); *C09B 11/02* (2013.01); *C09B 23/14* (2013.01); *C09B 23/141* (2013.01); *C09B 49/10* (2013.01); *C09B 57/001* (2013.01); *C09B 57/02* (2013.01); *C09B 67/0097* (2013.01); *G01N 33/84* (2013.01); *G01N 31/221* (2013.01); *G01N 33/582* (2013.01)

(58) Field of Classification Search
CPC ...................................... G01N 21/80
USPC ...................................... 436/163
See application file for complete search history.

(56) References Cited

U.S. PATENT DOCUMENTS

2013/0005583 A1 * 1/2013 Haushalter .......... C12Q 1/6825
506/2

OTHER PUBLICATIONS

Mills et al. "Highly CO2 sensitive extruded fluorescent plastic indicator film based on HPTS" Analyst, 2016, 141, 999 (Year: 2016).*

\* cited by examiner

*Primary Examiner* — Lyle Alexander
*Assistant Examiner* — Emily R. Berkeley
(74) *Attorney, Agent, or Firm* — Kinney & Lange, P.A.

(57) ABSTRACT

The present disclosure relates to a fluorogenic pH-sensitive dye and a film for detecting pH using the fluorogenic pH-sensitive dye on a polymer film. The fluorogenic pH-sensitive dye includes an aryl compound having a sulfonyl group ($-SO_2$) and an agarose compound covalently bonded to the sulfonyl group ($-SO_2$) of the aryl compound.

19 Claims, 12 Drawing Sheets

FLUOROGENIC PH-SENSITIVE DYES, FILM AND KIT COMPRISING THE SAME

CROSS-REFERENCE TO RELATED APPLICATIONS

This application claims the priority of Korean Patent Application No. 10-2017-0006461 filed on Jan. 13, 2017 and No. 10-2018-0003690 filed on Jan. 11, 2018, in the Korean Intellectual Property Office, the disclosure of which is hereby incorporated by reference in its entirety.

BACKGROUND

1. Technical Field

The present disclosure relates to a fluorogenic pH-sensitive dye, a film and a kit comprising the same.

2. Description of the Related Art

Fluorogenic is the most commonly used technique for tracking or analyzing biological molecules non-destructively in life sciences. When labeling a self-emitting dye or a dye having light emission characteristics on proteins, nucleic acids, lipids, and small molecules, it is possible to perform optical detection or analysis. By analyzing simple light emission characteristics, or changes in light emission characteristics according to imaging using change in light emission, energy transfer, change in surrounding environment, and changes in various chemical and optical properties such as changes in light emission characteristic by structural changes according to chemical reactions or changes in pH, etc., it is possible to obtain useful information in the life science field.

Equipment for the phenomenon analysis includes equipment for diagnosis and treatment such as fluorescence microscope and confocal microscope for cell observation, flow cytometer, microarray, real-time in-vivo imaging equipment, diagnostic kit and diagnostic equipment, and endoscopic equipment for medical imaging surgery, etc. In recent years, new application fields and more accurate and easily analyzable various equipment are being developed.

Measurement of intracellular pH or cytosol pH is very useful for determining cell function (Methods Mol Biol 637, 311 (2010); Nanotechnology 24,365 (2013)), and intracellular change in pH may achieve measurement cell activity such as ionic homeostasis, reactive oxygen species balance, apoptosis, cell cycle, cellular mobility, etc., (Circulation 124, 1806 (2011); Yonsei Med J 6, 473 (1995); J Bacteriol 185, 1190 (2003)). In addition, monitoring of intracellular pH plays an important role in identification of many metabolic pathways or in diagnosis or treatment of diseases.

The intracellular pH, etc., may be measured by using a pH marker, a pH detecting probe, or the like. Here, as a dye included in the pH marker or in the pH detecting probe, there is a need for a dye exhibiting high sensitivity and having stability with respect to small changes in neutral and physiological related pH of a biological system.

In addition, a pH detection film or microtiter plate may be used to measure the change in pH within a small amount of sample and a large number of samples. Here, there is a need for a dye which is easy to be manufactured into a film, has stability so that the dye is not eluted from the film upon pH detection, and has resistance to a buffer solution.

SUMMARY

It is an object of the present disclosure to provide a fluorogenic pH-sensitive dye with high sensitivity.

It is another object of the present disclosure to provide a film including the fluorogenic pH-sensitive dye with stability.

It is another object of the present disclosure to provide a method for stably coating a fluorogenic pH-sensitive dye on a plate.

It is another object of the present disclosure to provide a method for detecting pH in a sample and a method for detecting a disease in a sample therefrom.

Objects of the present disclosure are not limited to the above-described objects and other objects and advantages can be appreciated by those skilled in the art from the following descriptions. Further, it will be easily appreciated that the objects and advantages of the present disclosure can be practiced by means recited in the appended claims and a combination thereof.

In accordance with one aspect of the present disclosure, a fluorogenic pH-sensitive dye includes an aryl compound having a sulfonyl group ($-SO_2$); and an agarose compound covalently bonded to the sulfonyl group ($-SO_2$) of the aryl compound.

In accordance with another aspect of the present disclosure, there is provided as a film including the fluorogenic pH-sensitive dye as described above.

In accordance with still another aspect of the present disclosure, there is provided as a kit for detecting pH including the fluorogenic pH-sensitive dye as described above.

In accordance with still another aspect of the present disclosure, a method for coating a fluorogenic pH-sensitive dye includes: heating the fluorogenic pH-sensitive dye as described above to form a solution; and dropping the solution into each well of a plate, followed by gelling.

In accordance with still another aspect of the present disclosure, a method for detecting pH in a sample includes: contacting the sample with the fluorogenic pH-sensitive dye as described above; incubating the sample in contact with the fluorogenic pH-sensitive dye to form the cultured sample; irradiating the cultured sample with light to emit light; and detecting fluorescence emission from the sample.

DETAILED DESCRIPTION

Figure 1:
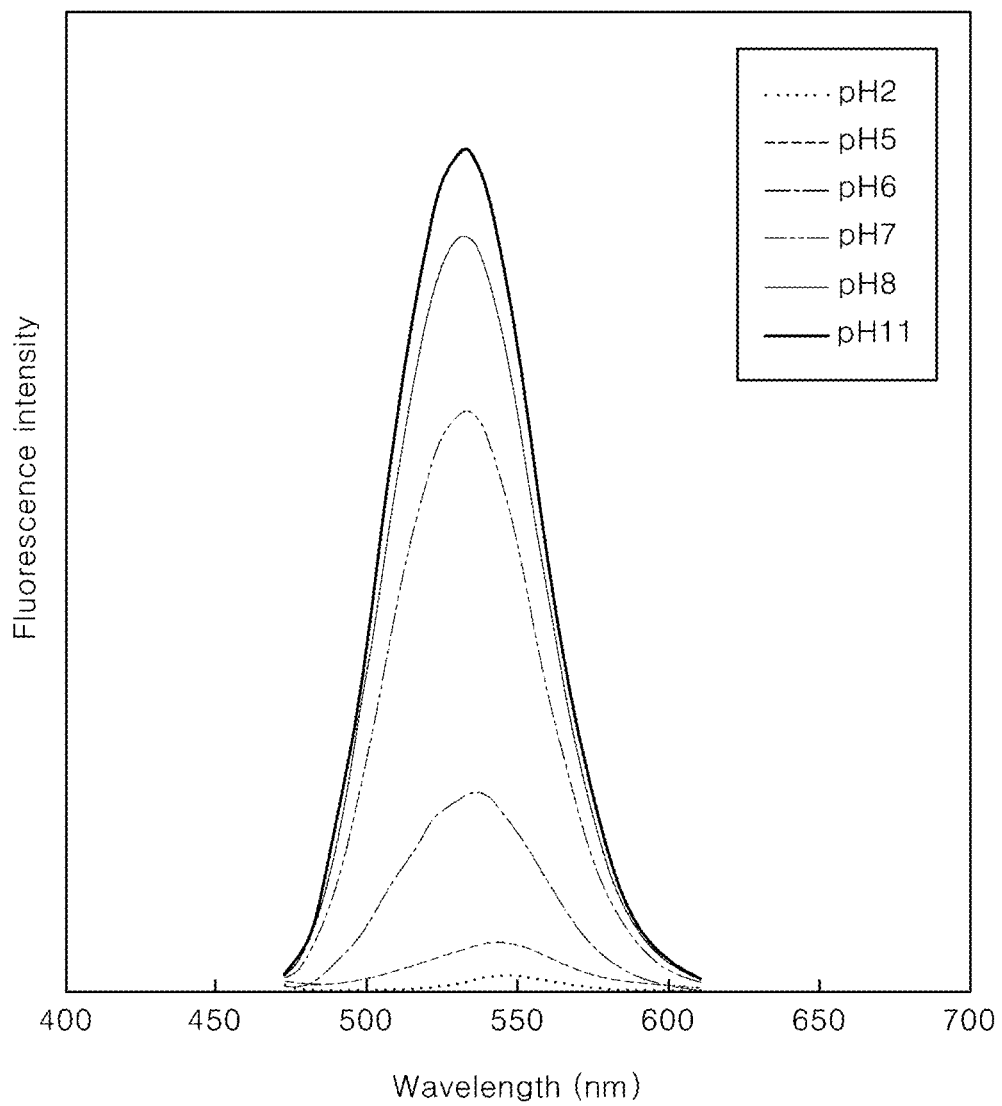
FIG. 1 shows emission spectrum results according to change in pH of a dye prepared by Preparation Example 12.

The above objects, features and advantages will become apparent from the detailed description with reference to the accompanying drawings. Embodiments are described in sufficient detail to enable those skilled in the art in the art to easily practice the technical idea of the present disclosure. Detailed descriptions of well known functions or configurations may be omitted in order not to unnecessarily obscure the gist of the present disclosure. Hereinafter, embodiments of the present disclosure will be described in detail with reference to the accompanying drawings. Throughout the drawings, like reference numerals refer to like elements.

Specific terms are defined herein so as to easily understand the present disclosure. Unless scientific and technical terms used herein are defined otherwise, they have meanings which are generally understood by those skilled in the art to which the present disclosure pertains.

In addition, the singular forms are intended to include the plural forms, unless the context specifically indicates otherwise, and it is further understood that the plural forms also include the singular forms thereof.

Dye

According to an aspect of the present disclosure, there is provided a fluorogenic pH-sensitive dye including an aryl compound having a sulfonyl group ($-SO_2$); and an agarose compound covalently bonded to the sulfonyl group ($-SO_2$) of the aryl compound.

The fluorogenic pH-sensitive dye is a dye in which sulfur of the aryl compound having a sulfonyl group ($-SO_2$) is formed by direct covalent bonding with oxygen of a hydroxy group or an alkoxy group of the agarose. In other words, the fluorogenic pH-sensitive dye is a compound in which the aryl compound and the agarose compound are directly covalently bonded using the sulfonate group ($-SO_3-$) as a linker, and may exhibit very high sensitivity to change in pH.

The aryl compound having the sulfonyl group ($-SO_2$) is derived from an aryl compound having a sulfonate ($-SO_3Ra$) group, and Ra may be an anion, hydrogen, or a substituent. Specifically, the substituent may be one selected from halogen, cyano, nitro, halogen, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, substituted alkyl, substituted aryl, and quaternary ammonium.

The aryl compound may have 1 to 3 sulfonyl groups ($-SO_2$), and each sulfonyl group ($-SO_2$) may be covalently bonded to the agarose.

The sulfonate group ($-SO_3-$) is an unstable functional group during the reaction, but may form a stable structure by forming a direct covalent bonding with the agarose of the dye. Accordingly, the dye may be efficiently utilized as a pH-sensitive sensor.

The agarose compound may be a linear polymer in which D-galactose and 3,6-anhydro-L-galactopyranose are alternately bonded to α-1,3- and β-1,4-glycoside, and may have a structure represented by Chemical Formula 1 below. In Chemical Formula 1 below, at least one R may be present at a position covalently bonded to the sulfonyl group ($-SO_2$) of the aryl compound:

[Chemical Formula 1]

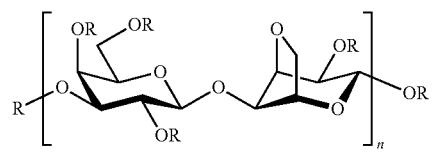

in Chemical Formula 1, n is an integer of 5 or more. The n may be 5 or more and one million or less, but is not limited thereto. Otherwise, the n may be 800,000 or less.

The agarose compound is chemically very stable, has no toxicity, is easy to handle, and does not cause cell transformation. In particular, the agarose compound is water-soluble and very stable with respect to an aqueous solution. The agarose compound is covalently bonded to the sulfonyl group ($-SO_2$) included in the aryl compound and is bonded to the aryl compound using the unstable sulfonate group ($-SO_3-$) as the linker in the dye. The dye may form a very stable structure by forming a direct covalent bonding between the stable agarose and the aryl compound in an aqueous environment.

In the fluorogenic pH-sensitive dye, the aryl compound having a sulfonate (—SO$_3$Ra) group may be a compound represented by Chemical Formula 2 below:

[Chemical Formula 2]

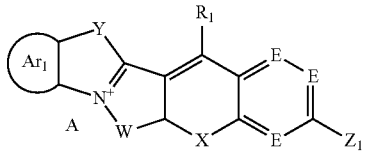

in Chemical Formula 2, at least one may have a sulfonate (—SO$_3$Ra) group. For example, at least one of Ar$_1$, Y, W, R$_1$, E, X, and Z$_1$ in Chemical Formula 2 may have a sulfonate (—SO$_3$Ra) group. The Ar$_1$ is substituted or unsubstituted aryl having 6 to 20 carbon atoms or substituted or unsubstituted heteroaryl having 2 to 20 carbon atoms.

The Ar$_1$ may be substituted with at least one substituent, respectively, and the at least one substituent is any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, In addition, the at least one substituent may be further substituted with at least one substituent when it is any one selected from alkyl, alkenyl, alkynyl, aryl, heteroaryl, arylalkyl, aryloxy, aryloxyalkyl, alkoxy and alkoxyalkyl, and the at least one substituent is selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

E is CR$_1$ or N, Z$_1$ is NR$_2$R$_3$, OR$_4$, SR$_5$, X is O, S, NR$_8$R$_9$, SiR$_{10}$R$_{11}$, CR$_{12}$R$_{13}$ or Se, Y is CR$_{14}$R$_{15}$, NR$_{16}$, O, S, Se, SiR$_{17}$R$_{18}$ or CR$_{19}$R$_{20}$=CR$_{21}$R$_{22}$, and W is CR$_{23}$R$_{24}$, CR$_{25}$R$_{26}$=CR5$_{27}$R$_{28}$, O, —[CR$_{29}$R$_{30}$—CR$_{31}$R$_{32}$]— or —[CR$_{33}$R$_{34}$—O]—.

R$_{23}$ to R$_{34}$ are the same as or different from each other and each independently hydrogen, deuterium, alkyl or acyloxy, and two adjacent to each other may be linked to form an alicyclic hydrocarbon.

Two of R$_1$ to R$_3$ and substituents adjacent thereto may be linked to each other to form an alicyclic hydrocarbon ring, a monocyclic aromatic hydrocarbon ring or a polycyclic aromatic hydrocarbon ring, and carbon atom of the formed alicyclic or aromatic hydrocarbon ring may be substituted with any one selected from N, S, O, Se, Te, Po, NR$_{35}$, SiR$_{36}$R$_{37}$, GeR$_{38}$R$_{39}$, PR$_{40}$, and BR$_{41}$.

R$_1$ to R$_{22}$ and R$_{29}$ to R$_{41}$ are the same as or different from each other, and each independently any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

R$_1$ to R$_{22}$ and R$_{29}$ to R$_{41}$ may be further substituted with at least one substituent when it is any one selected from alkyl, alkenyl, alkynyl, aryl, heteroaryl, arylalkyl, aryloxy, aryloxyalkyl, alkoxy and alkoxyalkyl, and the at least one substituent is selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

The substituent A is an organic ion or an inorganic ion, is not particularly limited, is appropriately selected in view of solubility of the dye according to the present disclosure or stability in an organic solvent depending on the use, and may be present as an anion or a cation or may be absent.

In general, the A may be an inorganic acid anion such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion, a tetrafluoro ion, or the like, may be an organic acid ion such as a thiocyanate ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkylsulfonic acid ion, a trihaloalkylsulfonic acid ion, a nicotinic acid ion, or the like, and may be a metal compound ion such as bisphenyl ditol, thiobisphenol chelate, bisdiol-α-diketone, or the like. Further, the A may be a metal ion such as sodium, potassium, or the like, and a quaternary ammonium ion.

According to an exemplary embodiment of the present disclosure, the A may be at least one selected from a halogen ion, —SO$_4^{2-}$, —S$_2$O$_3^{2-}$, —SO$^{3-}$, ClO$^{4-}$, —BF$^{4-}$, —PF$^{6-}$, —SbF$^{6-}$, —BiCl$^{5-}$, —AsF$^{6-}$, —SbCl$^{6-}$, —SnCl$^{6-}$, —COO$^-$, —HSO$^{4-}$, —SO$_3$CH$^{3-}$, Na$^+$, K$^+$, a quaternary ammonium ion, acetate, propionate and cyanate, and the A may be present or absent depending on the number of cations and substituted anions.

Further, in the fluorogenic pH-sensitive dye, the aryl compound having a sulfonate (—SO$_3$Ra) group may be a compound represented by Chemical Formula 3 below:

[Chemical Formula 3]

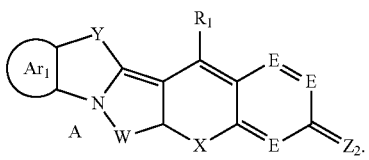

in Chemical Formula 3, at least one may have a sulfonate (—SO$_3$Ra) group. For example, at least one of Ar$_1$, Y, W, R$_1$, E, X, and Z$_2$ in Chemical Formula 3 may have a sulfonate (—SO$_3$Ra) group. The Ar$_1$ is substituted or unsubstituted aryl having 6 to 20 carbon atoms or substituted or unsubstituted heteroaryl having 2 to 20 carbon atoms.

The Ar$_1$ may be substituted with at least one substituent, respectively, and the at least one substituent is any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

Further, the at least one substituent may be further substituted with at least one substituent when it is any one selected from alkyl, alkenyl, alkynyl, aryl, heteroaryl, arylalkyl, aryloxy, aryloxyalkyl, alkoxy and alkoxyalkyl, and the at least one substituent is selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene glycol, and quaternary ammonium.

E is CR$_1$ or N, Z$_2$ is NR$_2$R$_3$, OR$_4$, SR$_5$, X is O, S, NR$_8$R$_9$, SiR$_{10}$R$_{11}$, CR$_{12}$R$_{13}$ or Se, Y is CR$_{14}$R$_{15}$, NR$_{16}$, O, S, Se, SiR$_{17}$R$_{18}$ or CR$_{19}$R$_{20}$=CR$_{21}$R$_{22}$, and W is CR$_{23}$R$_{24}$, CR$_{25}$R$_{26}$=CR5$_{27}$R$_{28}$, O, —[CR$_{29}$R$_{30}$—CR$_{31}$R$_{32}$]— or —[CR$_{33}$R$_{34}$—O]—.

R$_{23}$ to R$_{34}$ are the same as or different from each other and each independently hydrogen, deuterium, alkyl or acyloxy, and two adjacent to each other may be linked to form an alicyclic hydrocarbon.

Two of R$_1$ to R$_3$ and substituents adjacent thereto may be linked to each other to form an alicyclic hydrocarbon ring, a monocyclic aromatic hydrocarbon ring or a polycyclic aromatic hydrocarbon ring, and carbon atom of the formed alicyclic or aromatic hydrocarbon ring may be substituted with any one selected from N, S, O, Se, Te, Po, NR$_{35}$, SiR$_{36}$R$_{37}$, GeR$_{38}$R$_{39}$, PR$_{40}$, and BR$_{41}$.

R$_1$ to R$_{22}$ and R$_{29}$ to R$_{41}$ are the same as or different from each other, and each independently any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

R$_1$ to R$_{22}$ and R$_{29}$ to R$_{41}$ may be further substituted with at least one substituent when it is any one selected from alkyl, alkenyl, alkynyl, aryl, heteroaryl, arylalkyl, aryloxy, aryloxyalkyl, alkoxy and alkoxyalkyl, and the at least one substituent is selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

The substituent A is an organic ion or an inorganic ion, is not particularly limited, is appropriately selected in view of solubility of the dye according to the present disclosure or stability in an organic solvent depending on the use, and may be present as an anion or a cation or may be absent.

In general, the A may be an inorganic acid anion such as a phosphoric acid hexafluoride ion, a halogen ion, a phosphoric acid ion, a perchloric acid ion, a periodic acid ion, an antimony hexafluoride ion, a tartaric acid hexafluoride ion, a fluoroboric acid ion, a tetrafluoro ion, or the like, may be an organic acid ion such as a thiocyanate ion, a benzenesulfonic acid ion, a naphthalenesulfonic acid ion, a p-toluenesulfonic acid ion, an alkylsulfonic acid ion, a benzenecarboxylic acid ion, an alkylcarboxylic acid ion, a trihaloalkylcarboxylic acid ion, an alkylsulfonic acid ion, a trihaloalkylsulfonic acid ion, a nicotinic acid ion, or the like, and may be a metal compound ion such as bisphenyl ditol, thiobisphenol chelate, bisdiol-α-diketone, or the like. Further, the substituent A may be a metal ion such as sodium, potassium, or the like, and a quaternary ammonium ion.

According to an exemplary embodiment of the present disclosure, the substituent A may be at least one selected from a halogen ion, —SO$_4^{2-}$, —S$_2$O$_3^{2-}$, —SO$^{3-}$, ClO$^{4-}$, —BF$^{4-}$, —PF$^{6-}$, —SbF$^{6-}$, —BiCl$^{5-}$, —AsF$^{6-}$, —SbCl$^{6-}$, —SnCl$^{6-}$, —COO$^-$, —HSO$^{4-}$, —SO$_3$CH$^{3-}$, Na$^+$, K$^+$, a quaternary ammonium ion, acetate, propionate and cyanate, and the substituent A may be present or absent depending on the number of cations and substituted anions.

Meanwhile, the dye represented by Chemical Formulas 2 and 3 may include a reactive substituent so as to be able to bind to a labeling substance, and may include a substituent having polarity and charge to prevent interaction between dyes and undesired labeling occurrence between the dye and the various labeling factors.

According to a preferred embodiment of the present disclosure, at least one of the substituents may be conjugated with the labeling substance having a substituent such as an amine, a thiol, an alcohol, an aldehyde, a ketone, or the like.

The labeling substance may be a biomolecule, a nanoparticle, an organic compound, or the like, and is not particularly limited, but may be any one or more selected from the group consisting of antibody; antigen; lipid; protein; peptide; carbohydrate; dextran; fatty acid; phospholipid; lipopoly saccharide; nucleotide or oligonucleotide including or derived to include at least one of an amino group, a sulfhydryl group, a carbonyl group, a hydroxyl group, a carboxyl group, a thiol group, a phosphoric group and a thiophosphoric group; oxypolynucleotide or deoxypolynucleotide including or derived to include at least one of an amino group, a sulfhydryl group, a carbonyl group, a hydroxyl group, a carboxyl group, a thiol group, a phosphate group and a thiophosphate group; microorganism; drug; hormone; cell; cell membrane; and toxins.

Specifically, the reactive substituent according to the present disclosure may be activated ester, carboxyl, amide, acrylamide, azide, acyl azide, acyl halide, alkyne, amine, aldehyde, ketone, alkyl halide, alkyl sulfonate, aryl halide, aziridine, boronate, diazoalkane, epoxide, haloplatinate, halotriazines, imido ester, isocyanate, silyl halide, sulfonate ester, sulfonyl halide, succinimidyl ester, sulpho-succinimidyl ester, anhydride, acid halide, isothiocyanate, vinylsulphone, dichlorotriazine, haloacetamide, maleimide, carbodiimide, phosphoramidite, hydrazine, hydrazide, etc., and preferably, succinimidyl ester of carboxylic acid, isothiocyanate, maleimide, haloacetamide, etc.

The active ester has a structural formula —COR" having R' which is an excellent leaving group in the substitution reaction in the technical field to which the present disclosure pertains, wherein R" may be, for example, succinimidyloxy (—OC$_4$H$_4$O$_2$), sulfosuccinimidyloxy (—OC$_4$H$_3$O$_2$—SO$_3$H), or -1-oxybenzotriazolyl (—OC$_6$H$_4$N$_8$); or aryloxy or aryloxy including at least one of nitro, halogen, cyano, halogenalkyl, etc., belonging to an electron withdrawing group; or a carboxylic acid activated by carbodiimide constituting anhydride (OCOR$_a$ or —OCNR$_a$NHR$_b$) wherein R$_a$ or R$_b$ is alkyl having 1 to 6 carbon atoms, alkoxy having 1 to 6 carbon atoms, cyclohexyl, 3-dimethylaminopropyl, N-morpholinoethyl, etc.

In addition, the reactive substituent (RX) according to the present disclosure may be covalently bonded to various linkers (L) to form an RX-L- structure.

The linker may be a single bond or may be preferably a linear or branched chain having 1 to 20 atoms selected from the group consisting of carbon (C), nitrogen (N), oxygen (O) and sulfur (S), an aliphatic hydrocarbon ring, an aromatic hydrocarbon ring, an aliphatic heterocyclic ring, or an aromatic heterocyclic ring. In addition, the linker may have a positive (+) charge or a negative (−) charge.

According to the present disclosure, the dye represented by [Chemical Formulas 2] and [Chemical Formula 3] may be any one or more selected from compounds 1 to 51 below. For example, the compound 1 to the compound 34, the compound 47 and the compound 50 to the compound 51 are included in the dye represented by Chemical Formula 2, and the compounds 35 to 46 and the compounds 48 to 49 are included in the dye represented by Chemical Formula 3. Meanwhile, the range of [Chemical Formula 2] and [Chemical Formula 3] of the present disclosure is not limited thereto:

1

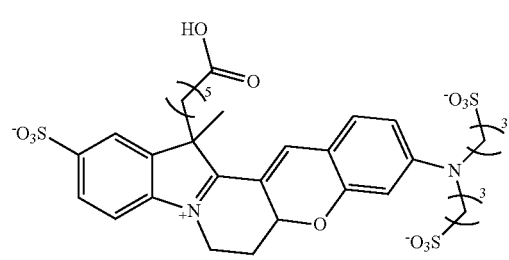

2

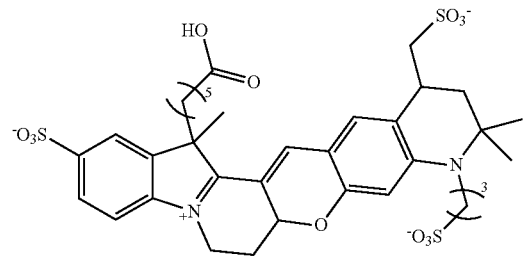

3

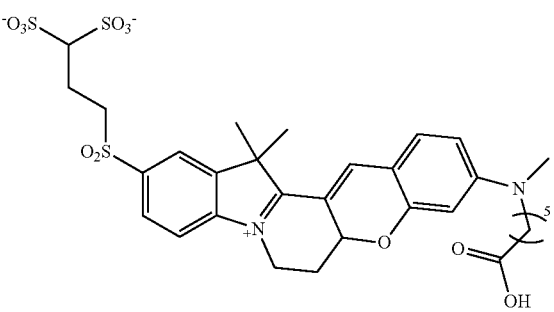

4

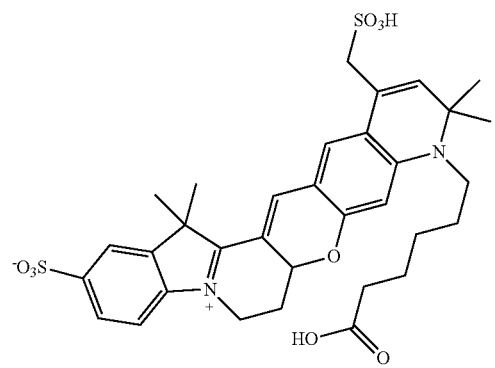

5

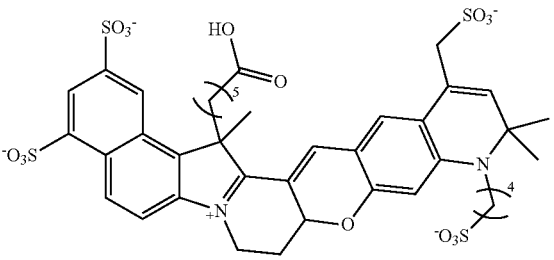

6

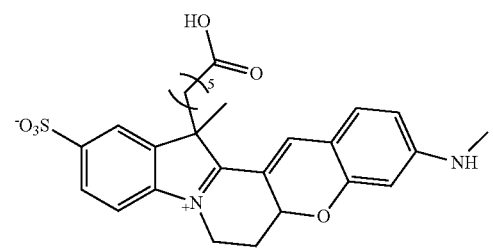

-continued
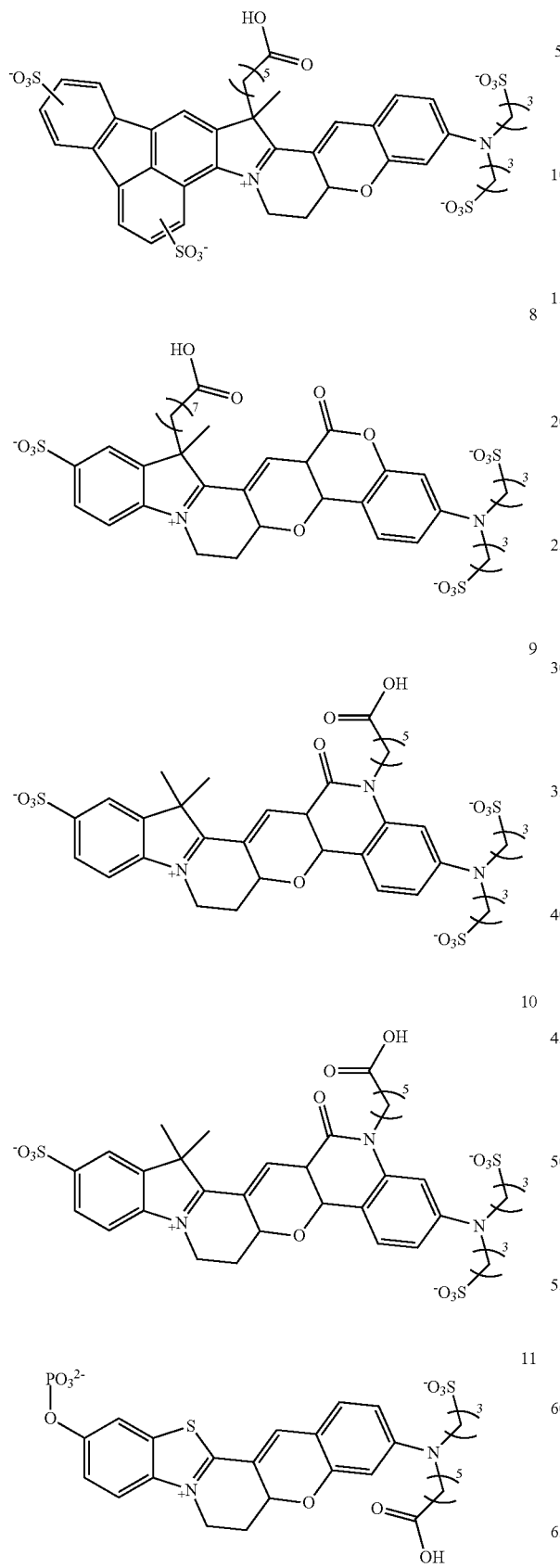
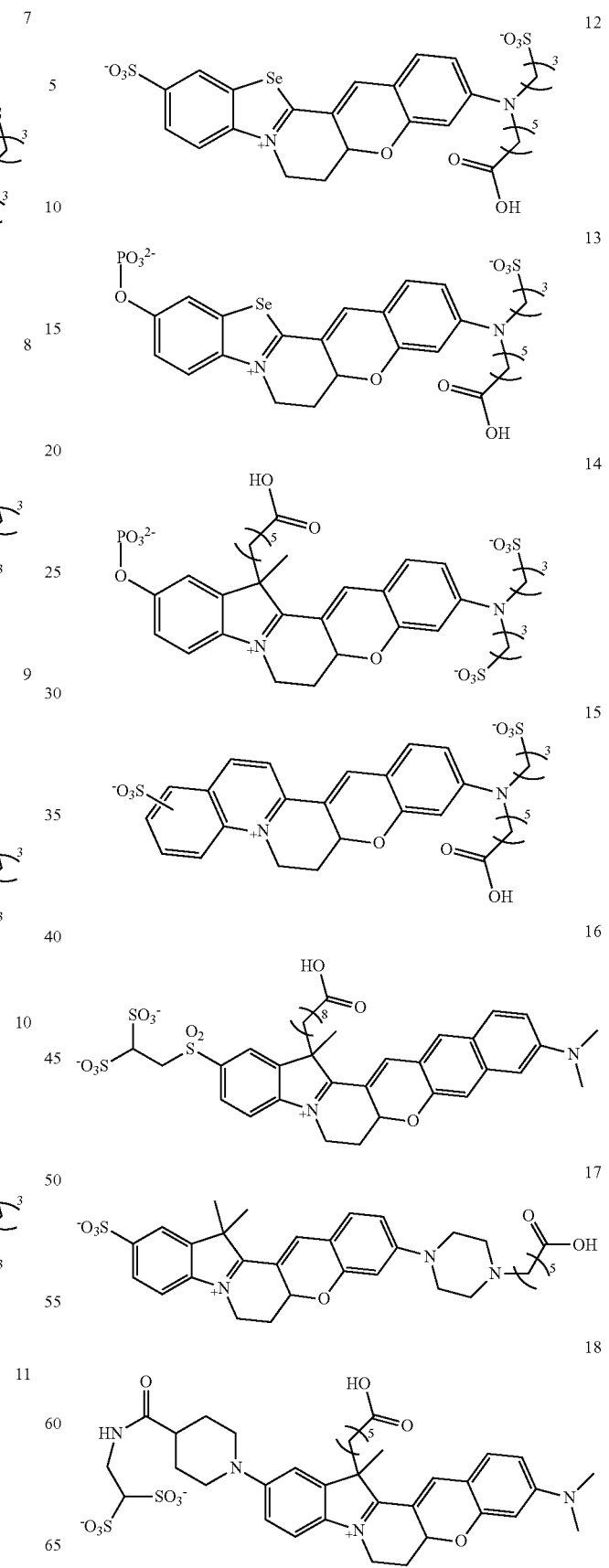

19
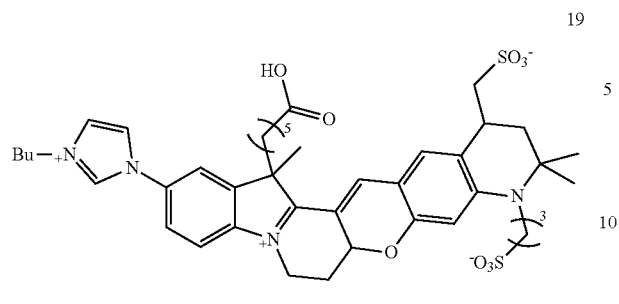
20
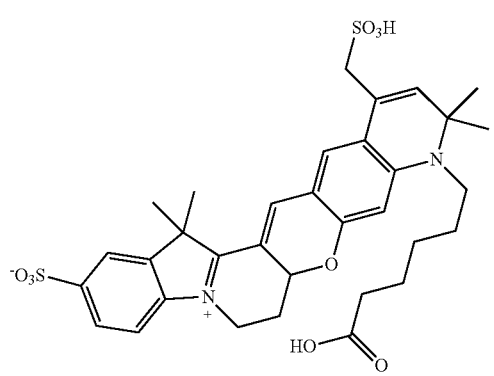
21
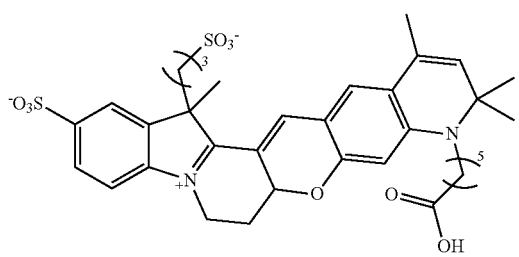
22
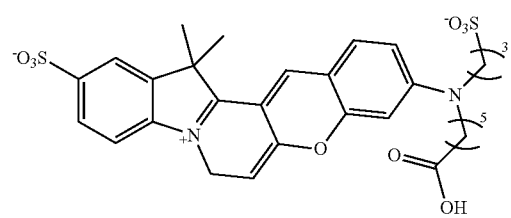
23
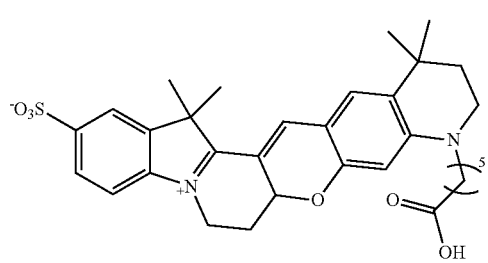
24
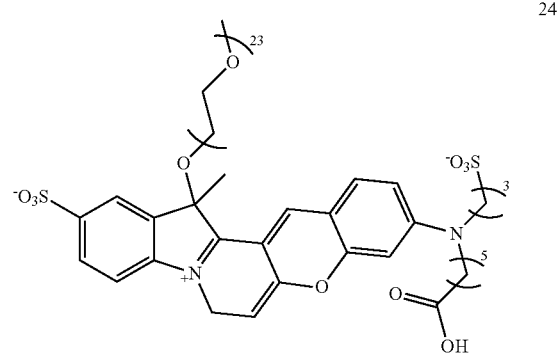
25
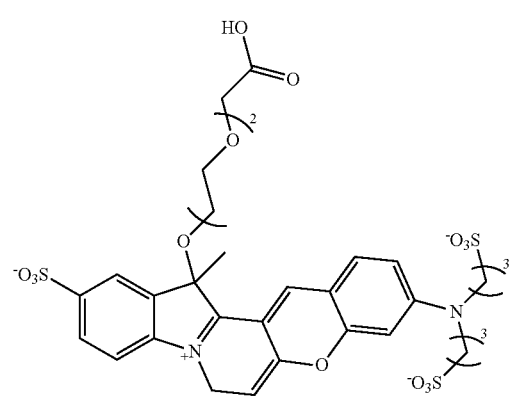
26
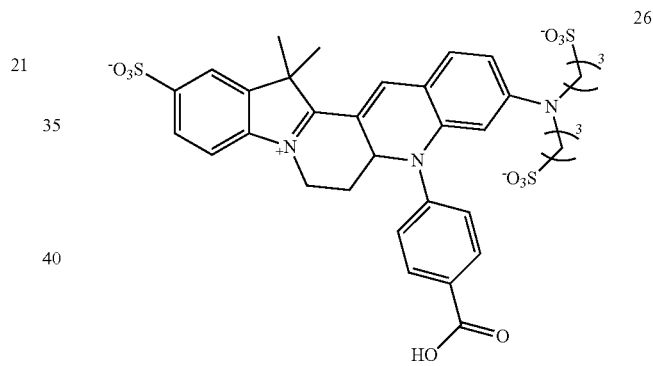
27
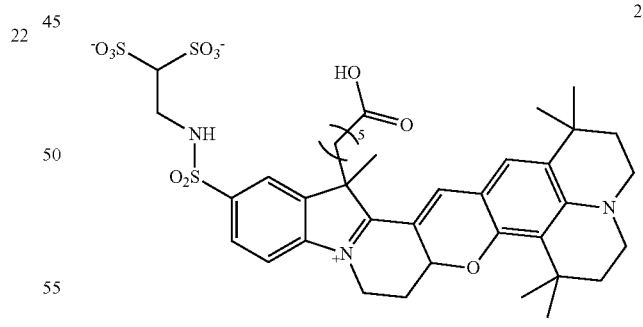
28
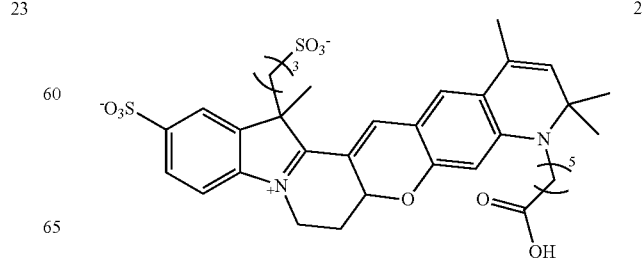

29
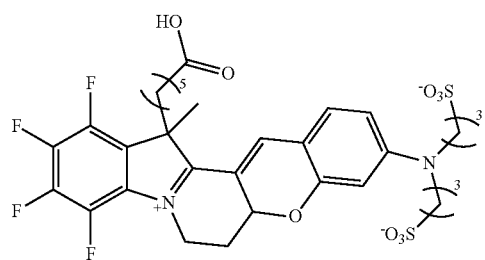
30
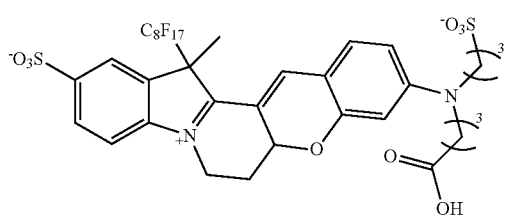
31
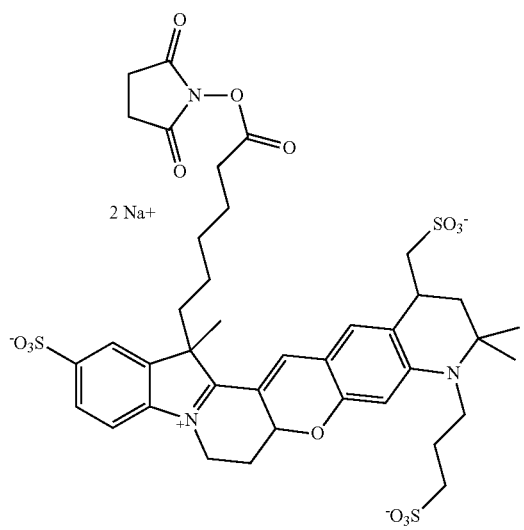
32
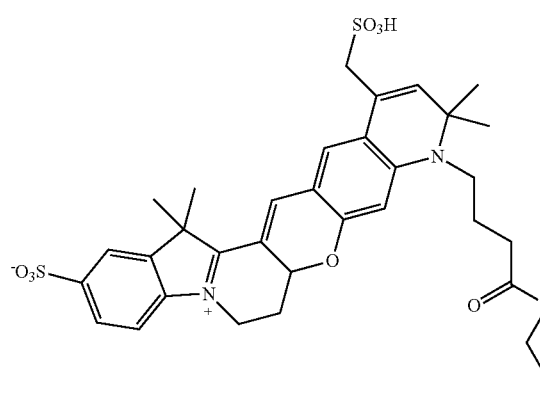
33
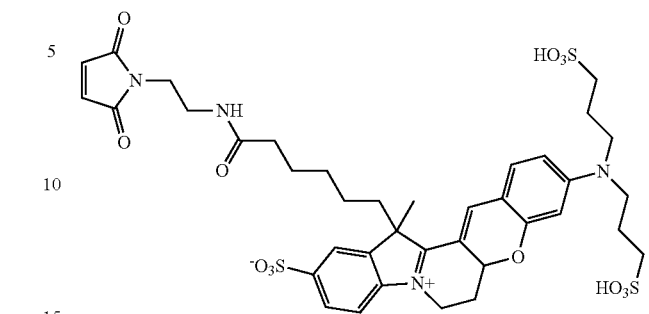
34
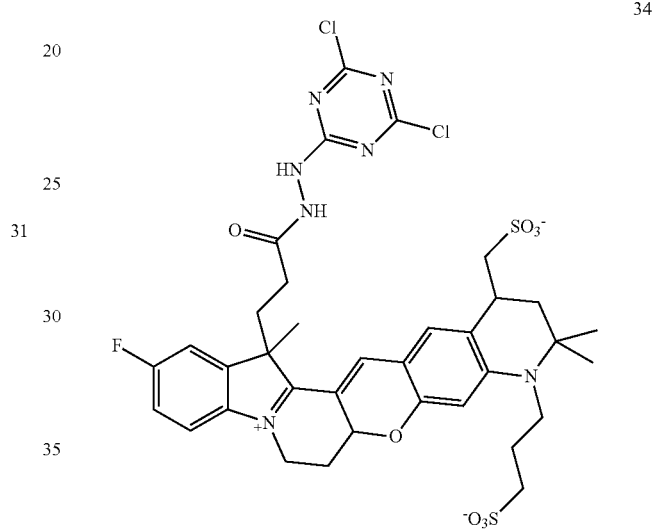
35
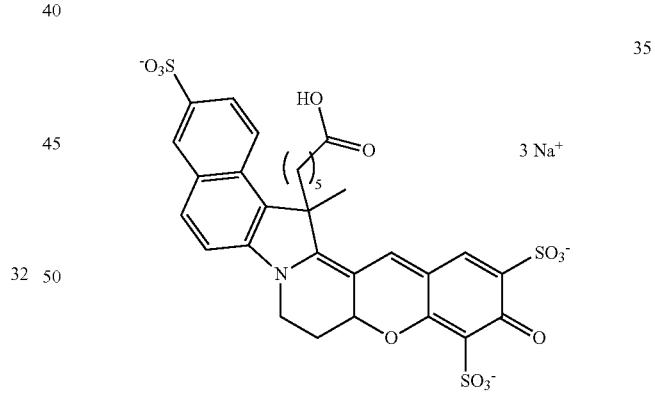
36
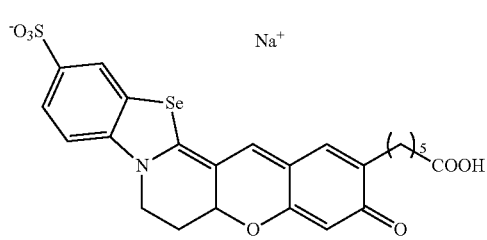

37
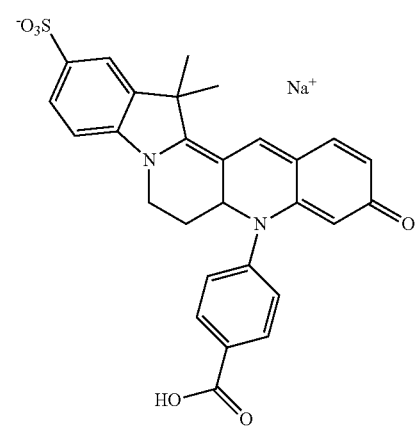
38
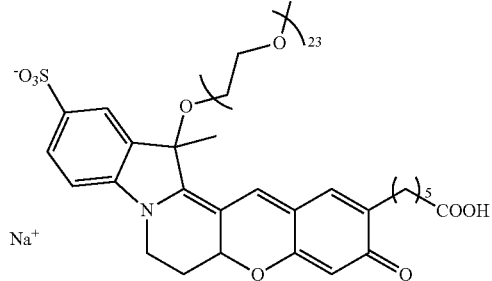
39
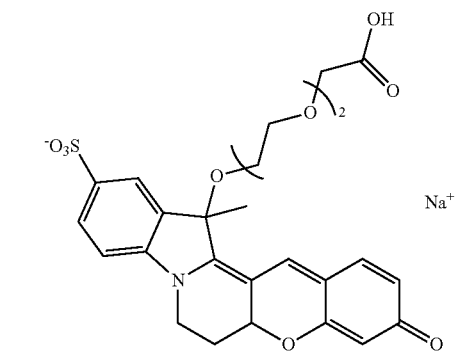
40
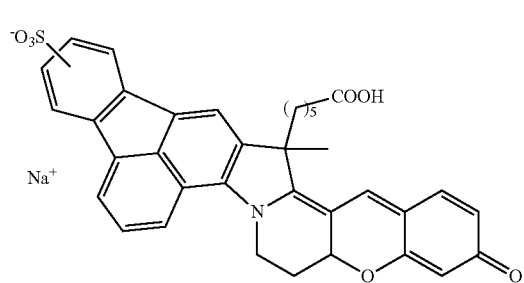
41
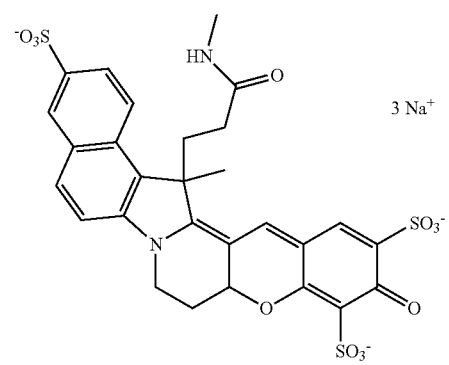
42
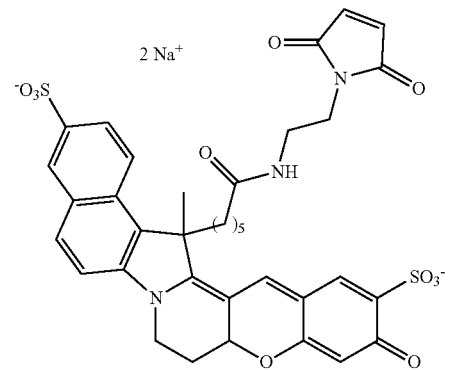
43
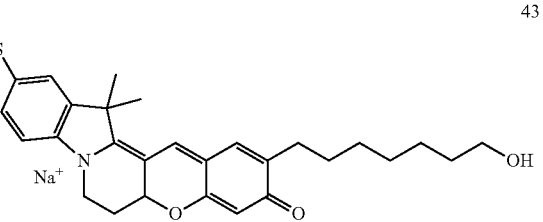
44
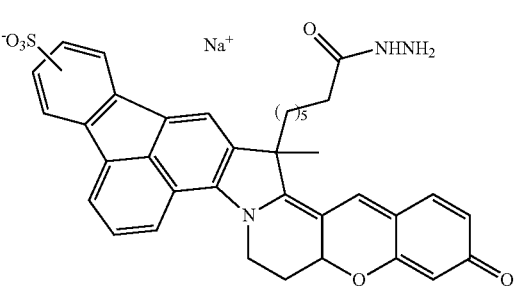
45
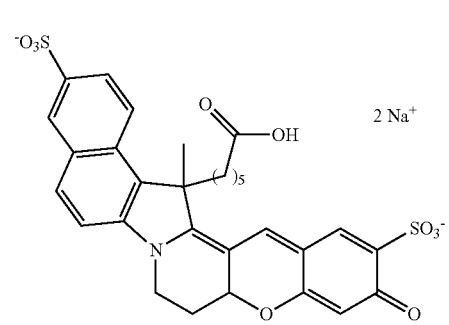

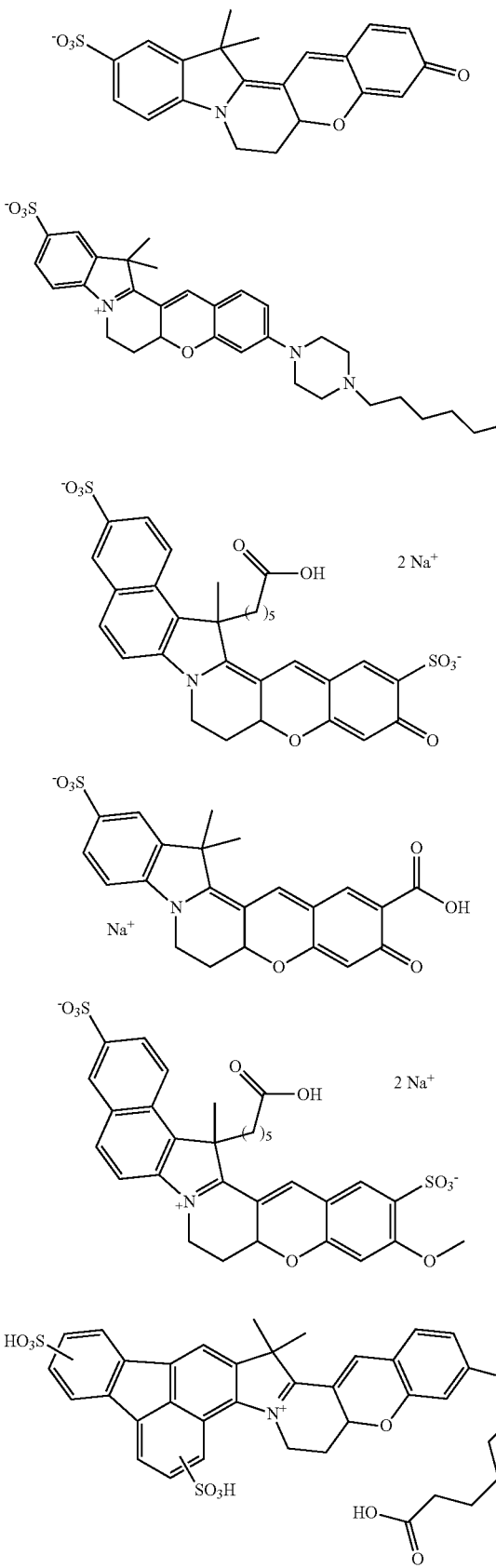

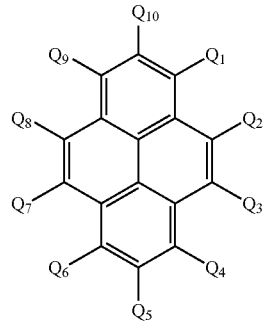

[Chemical Formula 4]

In addition, since the dye according to the present disclosure may be designed with various wavelengths of fluorescence, the user may select and use a desired wavelength. Accordingly, it is possible to selectively design various fluorescence wavelengths having a narrow band gap, and thus wavelengths of fluorescence with other probes may be prevented from overlapping. Therefore, a plurality of detections may be performed.

In addition, the dye according to the present disclosure is characterized in that the fluorescence intensity is changed according to a change in intracellular pH. Thus, the dye may be utilized for a pH probe capable of confirming the pH of a living cell, and further, an intracellular pH measurement sensor including the pH probe, etc.

In particular, the dye according to the present disclosure may be selected to emit strong fluorescence under an acidic condition between pH 2 and 6 or emit strong fluorescence under a basic condition between pH 8 to 12, and thus may be utilized more advantageously as the pH probe.

Further, in addition to the method for measuring pH through living cell staining, recently, a method for measuring pH of a cell through a plate reader is utilized. Thus, the dye according to the present disclosure may be applied to the method and may be used in various ways in various applications for measuring pH.

Further, in the fluorogenic pH-sensitive dye, the aryl compound having a sulfonate (—SO$_3$Ra) group may be a compound represented by Chemical Formula 4 below:

in Chemical Formula 4, at least one of Q1 to Q10 has a sulfonate (—SO$_3$Ra) group, at least one of Q1 to Q10 that do not have the sulfonate (—SO$_3$Ra) group has a hydroxyl group (—OH), and Q1 to Q10 that do not have the sulfonate (—SO$_3$Ra) group and the hydroxyl group (—OH) are hydrogen, deuterium or a substituent. Specifically, the substituent may be one selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

As an example, the compound represented by Chemical Formula 4 may have three sulfonate (—SO$_3$) groups, and the sulfur of the sulfonyl group (—SO$_2$) in the sulfonate (—SO$_3$) may be formed by direct covalent bonding with oxygen of a hydroxy group or an alkoxy group of the agarose, thereby forming the dye. In other words, the dye is a compound in which the aryl compound and the agarose compound are directly covalently bonded to each other using the sulfonate group (—SO$_3$—) as a linker, and may exhibit very high sensitivity to the change in pH.

The aryl compound may have 1 to 3 sulfonyl groups (—SO$_2$), and each sulfonyl group (—SO$_2$) may be covalently bonded to the agarose.

As a specific example, the Chemical Formula 4 may be a compound represented by Chemical Formula 5 below:

[Chemical Formula 5]

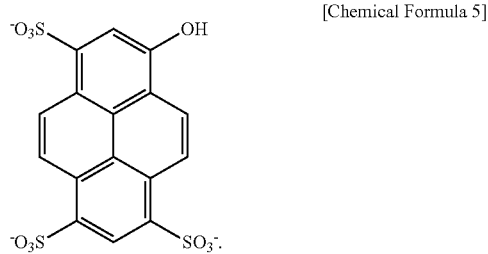

The compound represented by Chemical Formula 5 may be a compound derived from HPTS (8-hydroxypyrene-1,3, 6-trisulfonic acid trisodium salt).

The compound represented by Chemical Formula 5 is changed according to the change in pH as shown in Reaction Scheme 1 below, and thus the pH is able to be detected.

[Reaction Scheme 1]

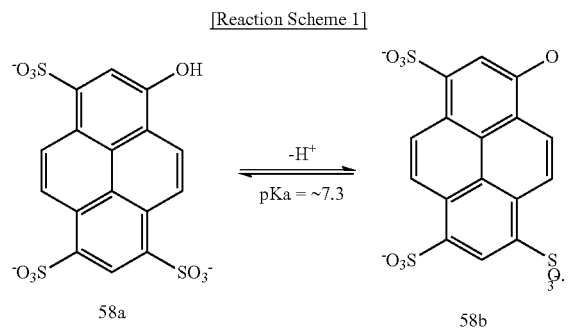

The compound represented by Chemical Formula 5 has various absorption and emission spectrum bands in the visible light region. The compound represented by Chemical Formula 5 may have a structure of 58a in which hydrogen is protonated under acidic conditions and 58b in which hydrogen is deprotonated under basic conditions. Here, the compounds having structures of 58a and 58b have characteristics in which absorbance increases with maximum absorption wavelength at two wavelengths, i.e., 405 nm and 465 nm, respectively, and then decreases, and fluorescence of 514 nm is emitted. Accordingly, the dye including the compound represented by Chemical Formula 5 is useful for pH detection.

In addition, three or four anionic dyes as shown in Chemical Formula 5 are well maintained in living cells having a physiological pH value, and thus may be more suitable for in-vivo cell pH detection.

When measuring intracellular pH or cytosol pH using the dye according to the present disclosure, cell activity such as ionic homeostasis, reactive oxygen species balance, apoptosis, cell cycle, cellular mobility, or the like, may be measured directly or indirectly.

Further, in addition to the method for measuring pH through living cell staining, recently, a method for measuring pH of a cell through a plate reader is utilized. Thus, the dye according to the present disclosure may be applied to the method, and may be used in various ways in various applications for measuring pH.

Film and Kit

According to another aspect of the present disclosure, there are provided a film and kit including at least one compound selected from fluorogenic pH-sensitive dyes according to various exemplary embodiments of the present disclosure.

First, the film of the present disclosure may be used as a sensor for detecting pH including at least one compound selected from the fluorogenic pH-sensitive dyes as described above.

Conventionally, a fluorogenic pH-sensitive dye has a problem in that the dye has a low solubility to water and thus, the dye is not able to be formed into a film. In addition, even if the fluorogenic pH-sensitive dye is conventionally manufactured in the form of a film, the film is put into a solution including the analyte, the dye included in the film is not stable in the film, but is eluted outside, and thus it is difficult to accurately measure the pH in the analyte.

The film of the present disclosure may include at least one compound selected from the above-described fluorogenic pH-sensitive dyes. Specifically, the film may include a compound including an aryl compound having a sulfonyl group (—SO$_2$); and an agarose compound covalently bonded to the sulfonyl group (—SO$_2$) of the aryl compound.

The aryl compound having the sulfonyl group (—SO$_2$) is derived from an aryl compound having a sulfonate (—SO$_3$Ra) group, and Ra may be an anion, hydrogen, or a substituent. The aryl compound may have 1 to 3 sulfonyl groups (—SO$_2$), and each sulfonyl group (—SO$_2$) may be covalently bonded to the agarose.

The sulfonate group (—SO$_3^-$) is an unstable functional group during the reaction, but may form a stable structure by forming a direct covalent bonding with the agarose of the dye. Accordingly, the dye may be efficiently utilized as a sensor for detecting pH.

Specifically, the agarose compound is chemically very stable, has no toxicity, is easy to handle, and does not cause cell transformation. In particular, the agarose compound is water-soluble and very stable with respect to an aqueous solution. The agarose compound is covalently bonded to the sulfonyl group (—SO$_2$) included in the aryl compound and is bonded to the aryl compound using the unstable sulfonate group (—SO$_3$—) as the linker in the dye. The dye may form a very stable structure by forming a direct covalent bonding between the stable agarose and the aryl compound in an aqueous environment.

Accordingly, during measuring pH in the solution including the analyte, the dye does not elute outside the film, and the high sensitivity property to the pH of the compound may be maintained as it is. In other words, the pH of the sample may be measured with high sensitivity using the film.

The film may be manufactured by making the fluorogenic pH-sensitive dye in the form of a powder to form a solution, followed by gelling, and compressing the gel on a polymer film.

Specifically, in the film, the fluorogenic pH-sensitive dye in the form of a powder may be added to distilled water, followed by heating at 80 to 100° C., and stirring until the dye is completely dissolved, thereby forming a solution. In addition, the solution may be placed in a desired frame and allowed to stand at room temperature to perform gelation. The gel may be pressed on a polymer film and dried to manufacture the film. The film may have a form of, for example, a patch or the like.

In addition, the polymer film may be impregnated into the solution in which the dye is dissolved, washed with distilled water to remove the dye that is not coated on the polymer film, and dried to manufacture the film.

The polymer film may be any film conventionally used in the field to which the disclosure belongs. For example, the polymer film may be a support on which cellulose, nitrocellulose, cellulose acetate, nylon, polyethersulfone, polyethylene terephthalate, polyfluorinated vinylidene, polypropylene film or polystyrene is supported.

Further, the film according to the present disclosure may be provided in an attached form with the $TiO_2$ layer. Here, the $TiO_2$ layer may serve as a reflective film, thereby contributing to enhancement of fluorescence intensity, brightness, and the like. The $TiO_2$ layer may be, for example, provided in a form attached on the polymer film coated with the dye by the above-described method.

In addition, the $TiO_2$ layer may be provided as a $TiO_2$ sol-gel type film and may be attached to the polymer film. The $TiO_2$ sol-gel type film means a film formed by coating a polymer in which a $TiO_2$ particle is dispersed on a transparent polymer film. A transparent adhesive layer may be interposed between the polymer film and the $TiO_2$ layer in order to attach the $TiO_2$ layer on the polymer film.

In addition, the film according to the present disclosure may be provided in a form attached to a polymer film (reference film) coated with the dye (reference dye) exhibiting light emission characteristic that is different from the dye according to the present disclosure. To this end, a transparent adhesive layer may be interposed between the polymer film coated with the dye according to the present disclosure and the reference film.

Here, the reference dye exhibiting light emission characteristic that is different from the dye according to the present disclosure is preferably a substance which exhibits light emission characteristic at different wavelength at the same pH as the dye according to the present disclosure or has no sensitivity to the change in pH. In other words, the reference dye is preferably a substance which does not react to pH and exhibits constant fluorescence intensity. In addition, the reference dye needs to have a small overlap of the absorption wavelength with the dye according to the present disclosure, and to have the same emission wavelength as the dye according to the present disclosure, and thus the reference dye is preferably a substance having a large stock shift.

The reference dye may be the following materials, but is not necessarily limited thereto:

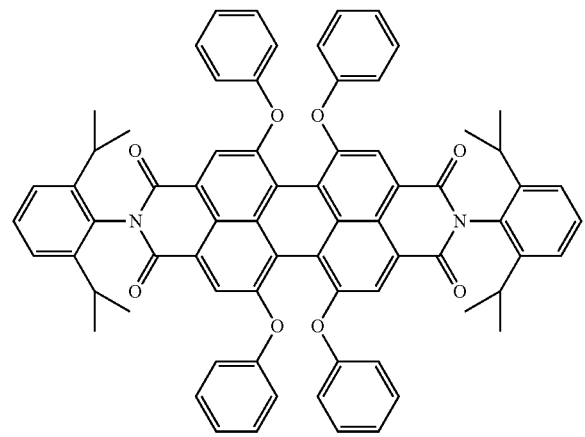

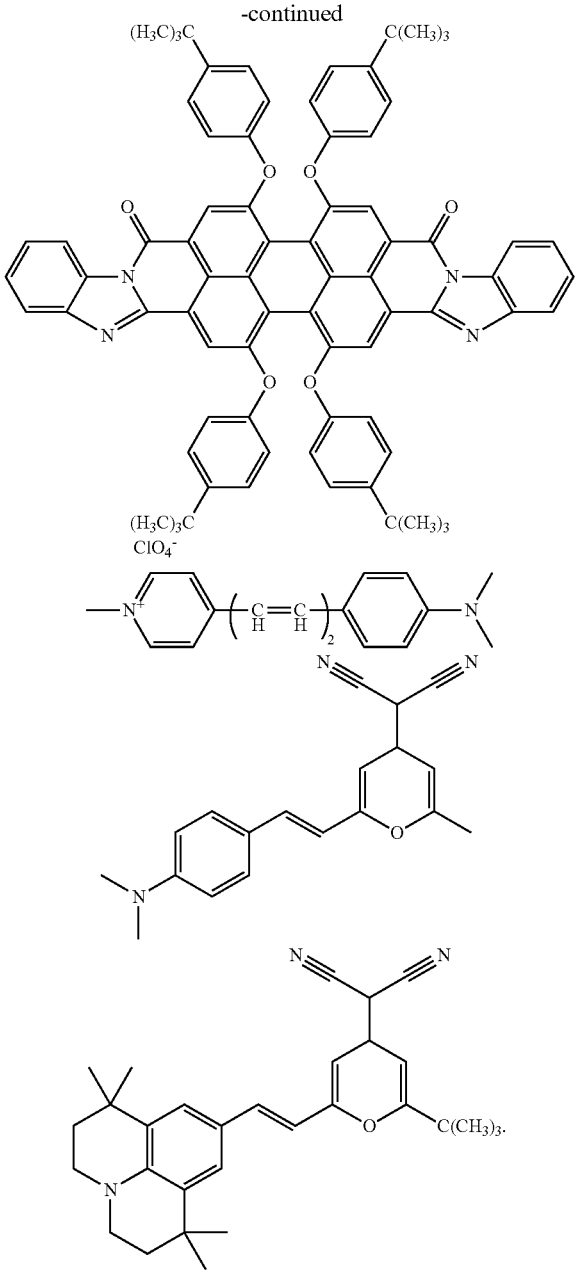

The film according to the present disclosure may be provided in an attached form with the reference film, and thus it is possible to accurately read the fluorescence intensity according to the pH by measuring the fluorescence intensity relative to the reference film, without performing a calibration operation.

Further, the present disclosure also provides a kit for detecting pH including the fluorogenic pH-sensitive dye.

Here, the kit may further include a biomolecule, a solvent (buffer solution, etc.), and other reagents, etc., if necessary. As the solvent, a buffer solution selected from the group consisting of a phosphate buffer solution, a carbonate buffer solution, and a tris buffer solution, an organic solvent selected from dimethylsulfoxide, dimethylformamide, dichloromethane, methanol, ethanol and acetonitrile, water, or the like, may be used, and it is possible to control the solubility by introducing various functional groups into a cyanine-based compound depending on the kind of the solvent.

Further, the kit may further include instructions.

Method for Coating on Plate

In addition to the method for measuring pH through living cell staining, recently, a method for measuring pH of a cell through a plate reader is utilized.

As an example, a microtiter plate has been widely used in high-throughput screening (HTS), enzyme-immunoassay analysis and toxicity testing. The microtiter plate has an advantage of being capable of simultaneously measuring a small amount of sample and a large number of samples. Since the large number of samples are measured at the same time, a microplate reader capable of rapidly detecting changes in absorbance or fluorescence has been widely used in many fields. Moreover, the microplate reader has been applied to other functions such as biochemical and chemical light emission complicated quantitative measurement as well as enzymatic activity measurement or cell respiration measurement. In the microtiter plate, an analyte such as enzyme, metabolite, and protein may be combined with some indicators in a thin layer of liquid medium or well bottoms. These bindings on the selected target enables quantitative evaluation of the emitted light associated with the substance and concentration of the analyte.

Conventionally, in order to coat a dye on a plate, first, a coating film is attached to the plate, and a film including the dye is attached on the coating film. Here, during the measurement of the pH of the analyte supported on the plate, the coating film and the film including the dye may be separated from each other, and thus it is difficult to measure the pH accurately.

The present disclosure may stably coat the dye according to various exemplary embodiments on the plate to prevent the film including the dye from being separated from the coating film during the pH measurement. Thus, the pH of the analyte supported on the plate may be measured with high sensitivity.

Specifically, the present disclosure provides a method for coating a fluorogenic pH-sensitive dye including: heating the fluorogenic pH-sensitive dye as described above to form a solution; and dropping the solution into each well of a plate, followed by gelling.

More specifically, the method of the present disclosure includes adding the fluorogenic pH-sensitive dye in the form of a powder to distilled water, followed by heating at 80 to 100° C., and stirring until the dye is completely dissolved, thereby forming a solution.

In addition, the coating method of the present disclosure includes maintaining the solution at 60° C. to 80° C. to prevent gelation before the solution is coated on the plate, and dropping the solution into each well of the plate, followed by gelling and drying at room temperature.

The solution of the fluorogenic pH-sensitive dye is gelled and dried in the well of the plate to thereby be gelled while stably bonding with the surface of the well. That is, the coating of the present disclosure may be attached well to the plate, and simultaneously may not be separated without a separate coating film. Thus, it is possible to prevent the phenomenon that the coating is separated from the plate during the detection of the pH of the analyte.

The fluorogenic pH-sensitive dye has a high-sensitivity characteristic with respect to the change in pH and is chemically stable to generate a fluorescent signal according to the change in pH in vivo, and thus the change in pH in vivo may be easily determined.

The fluorescence signal may be detected through various devices such as a plate reader, a microscope, a fluorometer, a quantum counter and a flow cell sorter, or through the naked eye.

Method for Detecting pH

The dye of the present disclosure may be used to not only directly or indirectly detect a specific cell change in relation to a change in pH but also to determine the change in pH in the environment caused by the cell and pH of a living cell or of a cell compartment. The cell compartment refers to one of cell organs suspended in the cell cytoplasm.

Another exemplary embodiment of the present disclosure provides a method for detecting pH in a sample including: contacting the sample with the fluorogenic pH-sensitive dye as described above; incubating the sample in contact with the fluorogenic pH-sensitive dye to form the cultured sample; irradiating the cultured sample with light to emit light; and detecting fluorescence emission from the sample.

Specifically, the fluorogenic pH-sensitive dye may be loaded into a living cell through methods such as microinjection, electroporation, and scrape loading, etc. Thus, the compound may be in contact with the sample.

The sample may be living cells, intracellular fluids, extracellular fluids, biological fluids, sera, biological fermentation media, buffer solutions, blood cells, immune cells, muscle tissue, neurons, extracellular vesicles, vascular tissue, blood fluids, urine, pharmaceuticals, etc.

The method for detecting pH in a sample of the present disclosure may include incubating the sample in contact with the fluorogenic pH-sensitive dye to form the cultured sample. Through the above-described incubating, the dye may be penetrated into cells.

As described above, the dye emits fluorescence according to pH such as pH in cells, or the like, and thus the intensity of fluorescence emitted from the sample may be detected to detect the pH in the sample.

Specifically, the pH may be determined from the fluorescence intensity measured by methods commonly known in the art to which the present disclosure pertains. For example, the pH may be determined by performing comparison with the standard known from the measured fluorescence intensity, for example, a calibration curve of fluorescence intensity with respect to pH. Alternatively, a normal device for measuring a fluorescence reaction may be used.

In addition, through the above-described method, etc., it is possible to monitor the change in pH in the cell, etc., and thus it is possible to find out matters directly or indirectly related to the change in pH. For example, intracellular processes may be appreciated by monitoring the change in pH in the cell.

Further, the present disclosure provides a method for detecting a disease in a sample including: contacting the sample which is obtained from an object with the fluorogenic pH-sensitive dye as described above; incubating the sample in contact with the fluorogenic pH-sensitive dye to form the cultured sample; irradiating the cultured sample with light to emit light; and detecting fluorescence emission from the sample.

For example, when the disease is a central nervous system disease such as Alzheimer's disease (AD), the fluorogenic pH-sensitive dye may be bonded to a carrier molecule related to the disease to thereby detect disease in the sample.

As another example, the fluorogenic pH-sensitive dye of the present disclosure may be used to detect diseases related to oxidative stress. Specifically, the oxidative stress may induce intracellular changes such as $Na^+/H^+$ and $Cl^-/$ $HCO_3^-$, etc. Accordingly, as the pH in the cell changes, the disease in the sample may be detected through the pH detection.

In addition, by using the fluorogenic pH-sensitive dye of the present disclosure, it is possible to detect a drug effective for the disease as well as the disease in the sample. For example, in the case of a drug effective for a particular disease, the drug may be administered to a cell having the disease to change the intracellular pH. Accordingly, a novel drug having an effect on a specific disease may be detected.

Hereinafter, specific examples of the present disclosure are provided. Meanwhile, Examples to be described below are just provided for specifically exemplifying or explaining the present disclosure, and accordingly, the present disclosure is not limited to the following Examples.

Preparation Example

Preparation Example 1: Synthesis of Compound 1

Synthesis of Compound Represented by [Chemical Formula 1-a]

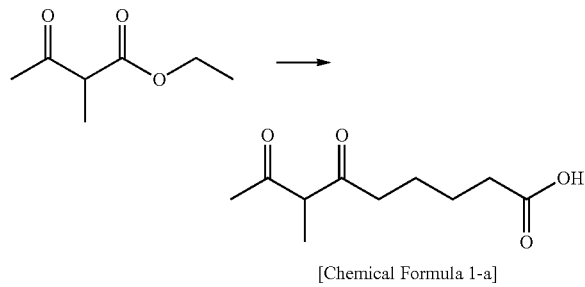

[Chemical Formula 1-a]

Ethyl 2-methylacetoactate (23.5 g, 163 mmol) and ethyl 6-bromohexanoate (40.0 g, 179 mmol) were added to ethanol (200 ml) and stirred. Liquid sodium ethoxide was added dropwise. The mixture was stirred at 80° C. for 10 hours. After the reaction was completed, the solid was filtered, and the filtered solution was distilled under reduced pressure. The reaction mixture was extracted with dichloromethane and 2N aqueous hydrochloric acid solution. The organic layer was treated with dried sodium sulfate, filtered and distilled under reduced pressure (47.7 g). When the solvent was removed, 300 ml of an aqueous solution was added, and the mixture was stirred under reflux for 10 hours. After the reaction was completed, the reaction mixture was extracted with dichloromethane, treated with sodium sulfate, filtered and distilled under reduced pressure to obtain a compound represented by [Chemical Formula 1-a] (25 g, 71%). LC-MS: m/z=185.84[M+]

(2) Synthesis of Compounds Represented by [Chemical Formula 1-b] and [Chemical Formula 1-c]

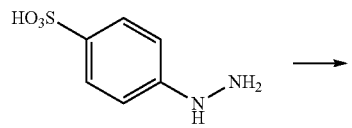

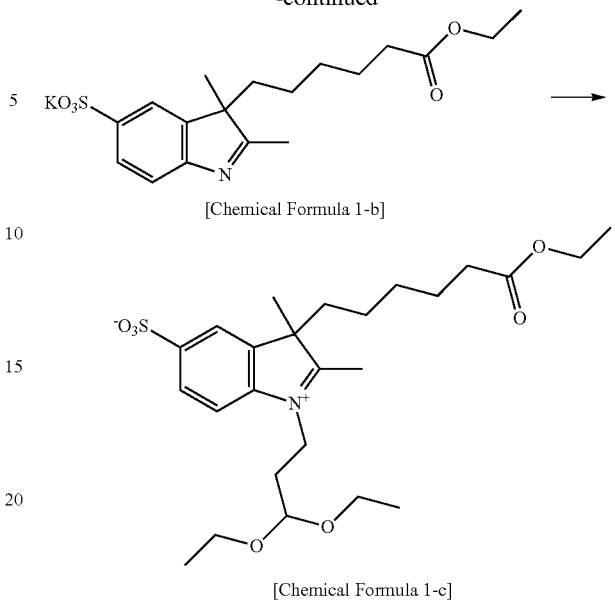

[Chemical Formula 1-b]

[Chemical Formula 1-c]

p-Hydrazinobenzenesulfonic acid (20 g, 106 mmol) and the compound represented by [Chemical Formula 1-a] (59.4 g, 319 mmol) were added to a 6N aqueous hydrochloric acid solution (30 ml)/ethanol (60 ml), and stirred under reflux for 12 hours. The mixture was cooled to room temperature, and the resulting solid was filtered. The filtrate was washed with ethyl acetate and dried under reduced pressure. Potassium hydroxide (1.4 g, 25.4 mmol) was dissolved in 35 ml of propanol and the filtered solid (5.1 g, 21.2 mmol) was dissolved in 35 ml of methanol and added dropwise. The mixture was stirred at room temperature for 12 hours. The solid was filtered and dried. Subsequently, the product was purified with water/methanol by C18 reverse phase chromatography to obtain a compound represented by [Chemical Formula 1-b] (11.1 g, 30%). LC-MS: m/z=404.86[M+]

The compound (3.0 g, 7.4 mmol) represented by [Chemical Formula 1-b] was stirred together with ethanol under a nitrogen atmosphere at room temperature, and a 48% aqueous hydrochloric acid solution (10.0 ml) was added dropwise. After 1 hour, the reaction solution was distilled under reduced pressure. Acetonitrile (120.0 ml), acetic acid (3.0 ml) and acrolein diethyl acetal (17.3 g, 133.0 mmol) were added to a reactor distilled under reduced pressure. The reaction solution was reacted at 70° C. for 2 hours. The reaction solution was subjected to distillation under reduced pressure and purified with a water/acetonitrile (0.1% trifluoroacetic acid) developing solution (20 ml/min, 10 to 100%) of by HPLC Rainin Dynamax C18, 8 μm column for 60 minutes, thereby obtaining a compound represented by [Chemical Formula 1-c] (1.2 g, 30%). LC-MS: m/z=496.96 [M+]

(3) Synthesis of Compounds Represented by [Chemical Formula 1-d] and [Chemical Formula 1-g]

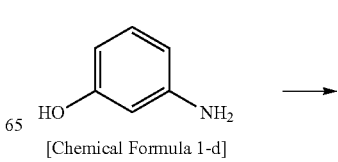

[Chemical Formula 1-d]

-continued

[Chemical Formula 1-e]

[Chemical Formula 1-f]

[Chemical Formula 1-g]

3-Aminophenol (5.0 g, 4.5 mmol) and 1,3-propanesultone (0.56 g, 4.6 mmol) were added to n-butanol and stirred under reflux for 30 minutes. The reaction solution was cooled to room temperature and stirred night and day. The reaction solution was filtered to separate a gray solid, and the solid was washed with methanol to obtain a compound represented by [Chemical Formula 1-d] (0.8 g, 80%). LC-MS: m/z=231.30[M+]

The compound (1 g, 4.3 mmol) represented by [Chemical Formula 1-d] and 1,3-propane sultone (0.54 g, 4.4 mmol) were added to 5 ml of N, N-dimethylformamide and stirred at 130° C. for 2 hours. The reaction solution was cooled to room temperature, distilled under reduced pressure, and purified by reverse phase chromatography to obtain a compound represented by [Chemical Formula 1-e] (1.48 g, 95%). LC-MS: m/z=353.19[M+]

The compound (3.0 g, 8.0 mmol) represented by [Chemical Formula 1-e] was placed in a reactor containing N, N-dimethylformamide (1.3 g, 8.0 mmol). The reaction solution was reacted at 50° C. for 12 hours. After the reaction was completed, the reaction solution was diluted with water and neutralized. The solvent was removed, and the obtained product was purified by reverse phase chromatography to obtain a compound represented by [Chemical Formula 1-f] (0.8 g, 25%). LC-MS: m/z=380.84[M+]

(4) Synthesis of Compound 1

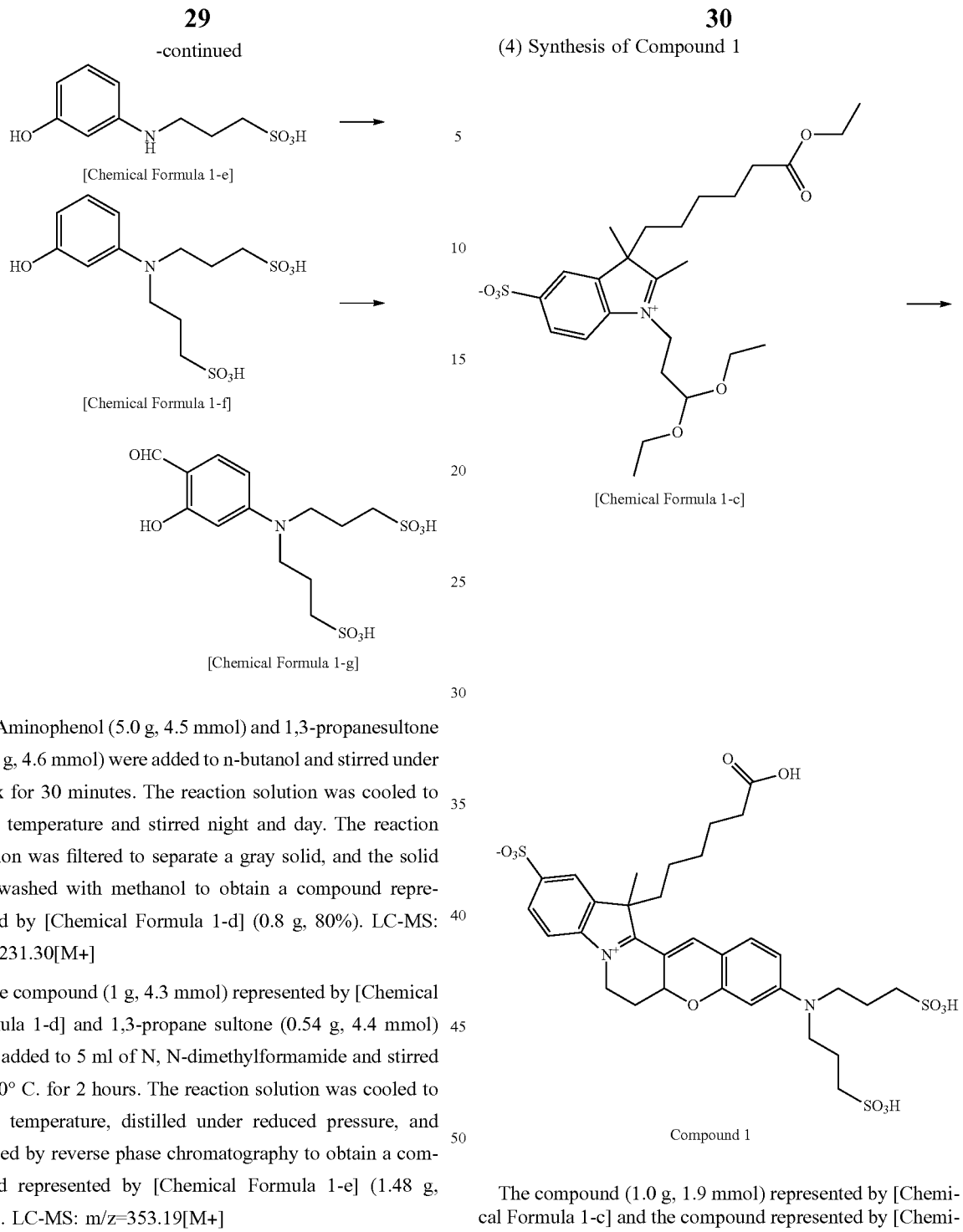

[Chemical Formula 1-c]

Compound 1

The compound (1.0 g, 1.9 mmol) represented by [Chemical Formula 1-c] and the compound represented by [Chemical Formula 1-f] (0.8 g, 1.9 mmol) were dissolved in 20 ml of ethanol and stirred at 80° C. for 8 hours. After the reaction was completed, the solvent was removed by concentration under reduced pressure. The concentrated reaction product was dissolved in 50 ml of chloroform, and 1 ml of 50% sulfuric acid was added dropwise. The reaction solution was diluted with dichloromethane and extracted with water. The organic layer was concentrated under reduced pressure and purified with a water/acetonitrile (0.1% trifluoroacetic acid) developing solution (20 ml/min, 10 to 100%) of by HPLC Rainin Dynamax C18, 8 μm column for 60 minutes, thereby synthesizing a compound 1 (0.4 g, 51%). LC-MS: m/z=739.79[M+]

Preparation Example 2. Synthesis of Compound 2

(1) Synthesis of Compound Represented by [Chemical Formula 2-a]

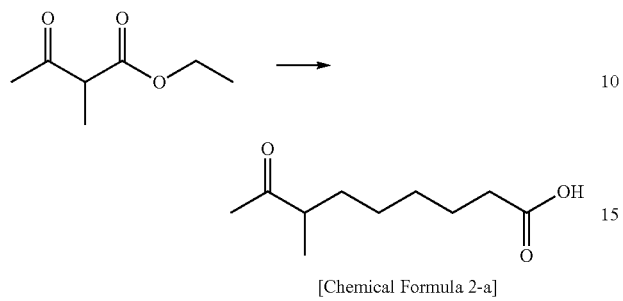

[Chemical Formula 2-a]

Ethyl 2-methylacetoactate (23.5 g, 163 mmol) and ethyl 6-bromohexanoate (40.0 g, 179 mmol) were added to ethanol (200 ml) and stirred. Liquid sodium ethoxide was added dropwise. The mixture was stirred at 80° C. for 10 hours. After the reaction was completed, the solid was filtered, and the filtered solution was distilled under reduced pressure. The resultant product was extracted with dichloromethane and 2N aqueous hydrochloric acid solution. The organic layer was treated with dried sodium sulfate, filtered and distilled under reduced pressure (47.7 g). When the solvent was removed, 300 ml of an aqueous solution was added, and the mixture was stirred under reflux for 10 hours. After the reaction was completed, the reaction mixture was extracted with dichloromethane, treated with sodium sulfate, filtered and distilled under reduced pressure to obtain a compound represented by [Chemical Formula 2-a] (25 g, 71%). LC-MS: m/z=185.84[M+]

(2) Synthesis of Compounds Represented by [Chemical Formula 2-b] and [Chemical Formula 2-c]

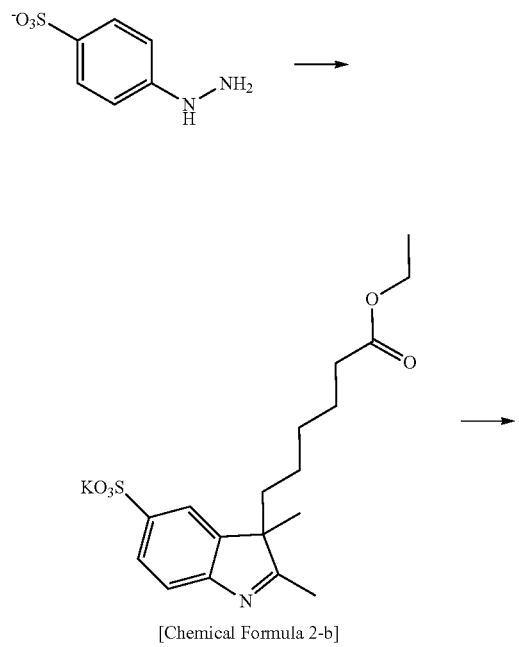

[Chemical Formula 2-b]

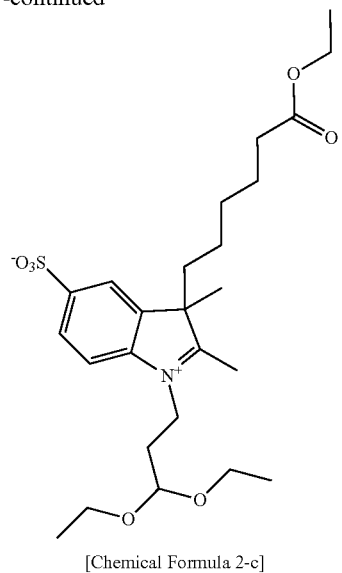

[Chemical Formula 2-c]

p-Hydrazinobenzenesulfonic acid (20 g, 106 mmol) and the compound represented by [Chemical Formula 2-a] (59.4 g, 319 mmol) were added to a 6N aqueous hydrochloric acid solution (30 ml)/ethanol (60 ml), and stirred under reflux for 12 hours. The mixture was cooled to room temperature, and the resulting solid was filtered, washed with ethyl acetate, and dried under reduced pressure. Potassium hydroxide (1.4 g, 25.4 mmol) was dissolved in 35 ml of propanol and the filtered solid (5.1 g, 21.2 mmol) was dissolved in 35 ml of methanol and added dropwise. The mixture was stirred at room temperature for 12 hours. The solid was filtered and dried. The product was purified with water/methanol by C18 reverse phase chromatography to obtain a compound represented by [Chemical Formula 2-b] (11.1 g, 30%). LC-MS: m/z=404.86[M+]

The compound (3.0 g, 7.4 mmol) represented by [Chemical Formula 2-b] was stirred together with ethanol under a nitrogen atmosphere at room temperature, and a 48% aqueous hydrochloric acid solution (10.0 ml) was added dropwise. After 1 hour, the reaction solution was distilled under reduced pressure. Acetonitrile (120.0 ml), acetic acid (3.0 ml) and acrolein diethyl acetal (17.3 g, 133.0 mmol) were added to a reactor distilled under reduced pressure. The reaction solution was reacted at 70° C. for 2 hours. The reaction solution was subjected to distillation under reduced pressure and purified with a water/acetonitrile (0.1% trifluoroacetic acid) developing solution (20 ml/min, 10 to 100%) of by HPLC Rainin Dynamax C18, 8 μm column for 60 minutes, thereby obtaining a compound represented by [Chemical Formula 2-c] (1.2 g, 30%). LC-MS: m/z=496.96 [M+]

(3) Synthesis of Compounds Represented by [Chemical Formula 2-d] and [Chemical Formula 2-h]

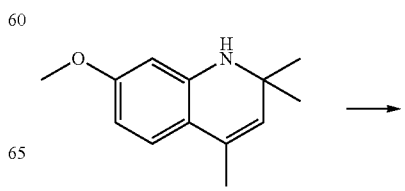

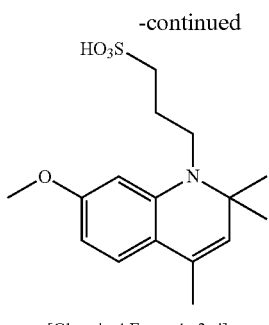

[Chemical Formula 2-d]

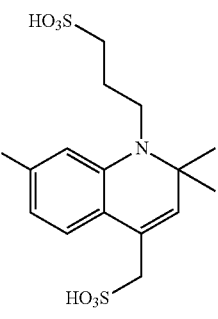

[Chemical Formula 2-e]

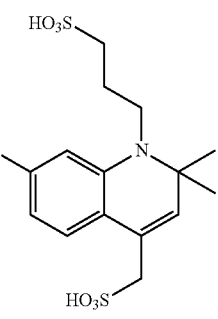

[Chemical Formula 2-d]

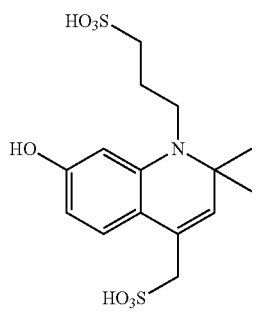

[Chemical Formula 2-g]

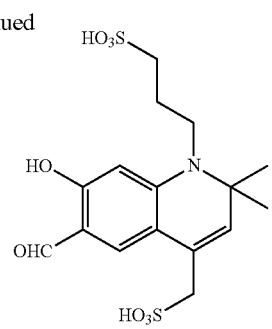

[Chemical Formula 2-h]

7-Methoxy-2,2,4-trimethyl-1,2-hydroquinoline (10.0 g, 49 mmol) and 1,3-propanesulfone (6.6 g, 54 mmol) were stirred at 145° C. for 3 hours. After the reaction was completed, the obtained product was purified by column chromatography to obtain a compound represented by [Chemical Formula 2-d] (10.0 g, 63%). LC-MS: m/z=325.01[M+]

A sulfonic acid (9.8 ml) was added dropwise to the reactor containing the compound represented by [Chemical Formula 2-d] (10.0 g, 31 mmol). After stirring for 30 minutes, 3.9 ml of 20.0% oleum was added dropwise at 0° C. and reacted for 48 hours. After the reaction was completed, the reaction mixture was added to water in a low temperature state. The reaction mixture was neutralized with NaOH and recrystallized with ethanol to obtain a compound represented by [Chemical Formula 2-e] (11.0 g, 88%). LC-MS: m/z=404.88[M+]

The compound represented by [Chemical Formula 2-e] (12.0 g, 30.0 mmol), 10% Pd/C (0.9 g) and 120 ml of methanol were added, and stirred at room temperature under a hydrogen atmosphere. The reaction mixture was stirred for 12 hours, and the solid was filtered. The filtered solution was distilled under reduced pressure and recrystallized with ethanol to obtain a compound represented by [Chemical Formula 2-f] (11.5 g, 95%). LC-MS: m/z=406.78[M+]

The compound represented by [Chemical Formula 2-f], NaI (11.0 g, 74.0 mmol), and HBr (72.0 g, 174.0 mmol) were placed in a reactor, and stirred at 105° C. for 12 hours. After the reaction was completed, the reaction solution was neutralized with an aqueous sodium bicarbonate solution. The solvent was removed and crystals were produced by using water/acetone/ethanol. The crystals were subjected to recrystallization using methanol/acetone, followed by washing with acetone to obtain a compound represented by [Chemical Formula 2-g] (3.0 g, 27%). LC-MS: m/z=392.93 [M+]

The compound (3.0 g, 8.0 mmol) represented by [Chemical Formula 2-e] was placed in a reactor containing N,N-dimethylformamide (1.3 g, 8.0 mmol). The reaction solution was reacted at 50° C. for 12 hours. After the reaction was completed, the reaction solution was diluted with water and neutralized. The solvent was removed, and then crystals were produced by using methanol/acetone. The crystals were subjected to recrystallization using ethanol to obtain a compound represented by [Chemical Formula 2-h] (0.8 g, 25%). LC-MS: m/z=420.74 [M+]

(4) Synthesis of Compound 2

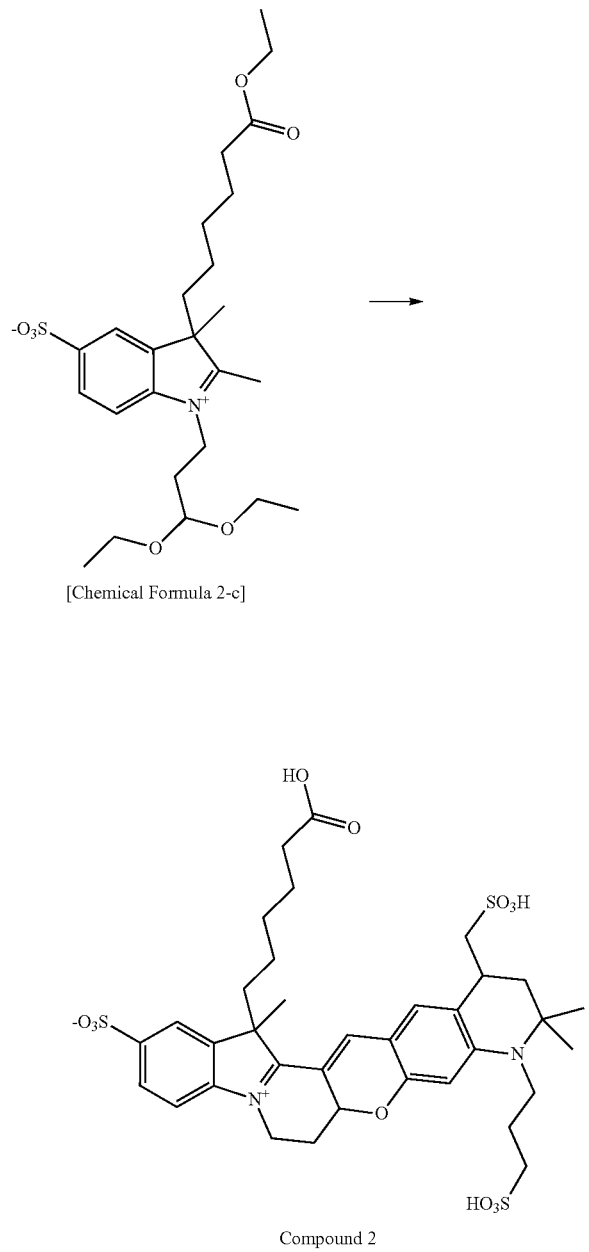

[Chemical Formula 2-c]

Compound 2

The compound (1.0 g, 1.9 mmol) represented by [Chemical Formula 2-c] and the compound represented by [Chemical Formula 2-h] (0.8 g, 1.9 mmol) were dissolved in 20 ml of ethanol and stirred at 80° C. for 8 hours. After the reaction was completed, the solvent was removed by concentration under reduced pressure. The concentrated reaction product was dissolved in 50 ml of chloroform, and 1 ml of 50% sulfuric acid was added dropwise. The obtained product was diluted with dichloromethane and extracted with water. The organic layer was concentrated under reduced pressure and purified with a water/acetonitrile (0.1% trifluoroacetic acid) developing solution (20 ml/min, 10 to 100%) of by HPLC Rainin Dynamax C18, 8 μm column for 60 minutes, thereby synthesizing a compound 2 (0.4 g, 51%). LC-MS: m/z=780.01[M+]

(5) Synthesis of Compound 36

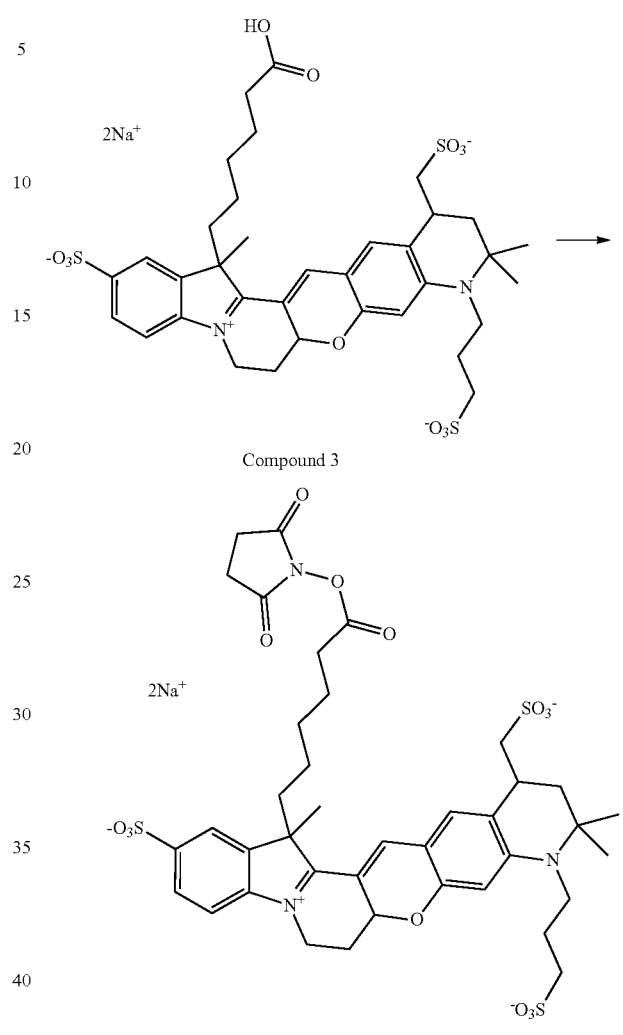

Compound 3

Compound 36

The compound 2 (0.24 g, 0.5 mmol), N-hydroxysuccinimide (0.03 g, 0.03 mmol), N,N-dicyclohexyl carbodiimide (0.054 g, 0.03 mmol) were dissolved in 1 ml of N,N-dimethyl formamide, and stirred at room temperature for 1 hour. The reaction was completed, and the obtained product was purified with a water/acetonitrile (0.1% trifluoroacetic acid) developing solution (20 ml/min, 10 to 100%) of by HPLC Rainin Dynamax C18, 8 μm column for 60 minutes, thereby synthesizing a compound 36 (0.15 g, 56.6%).

Preparation Example 3. Synthesis of Compound 3

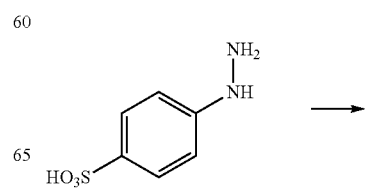

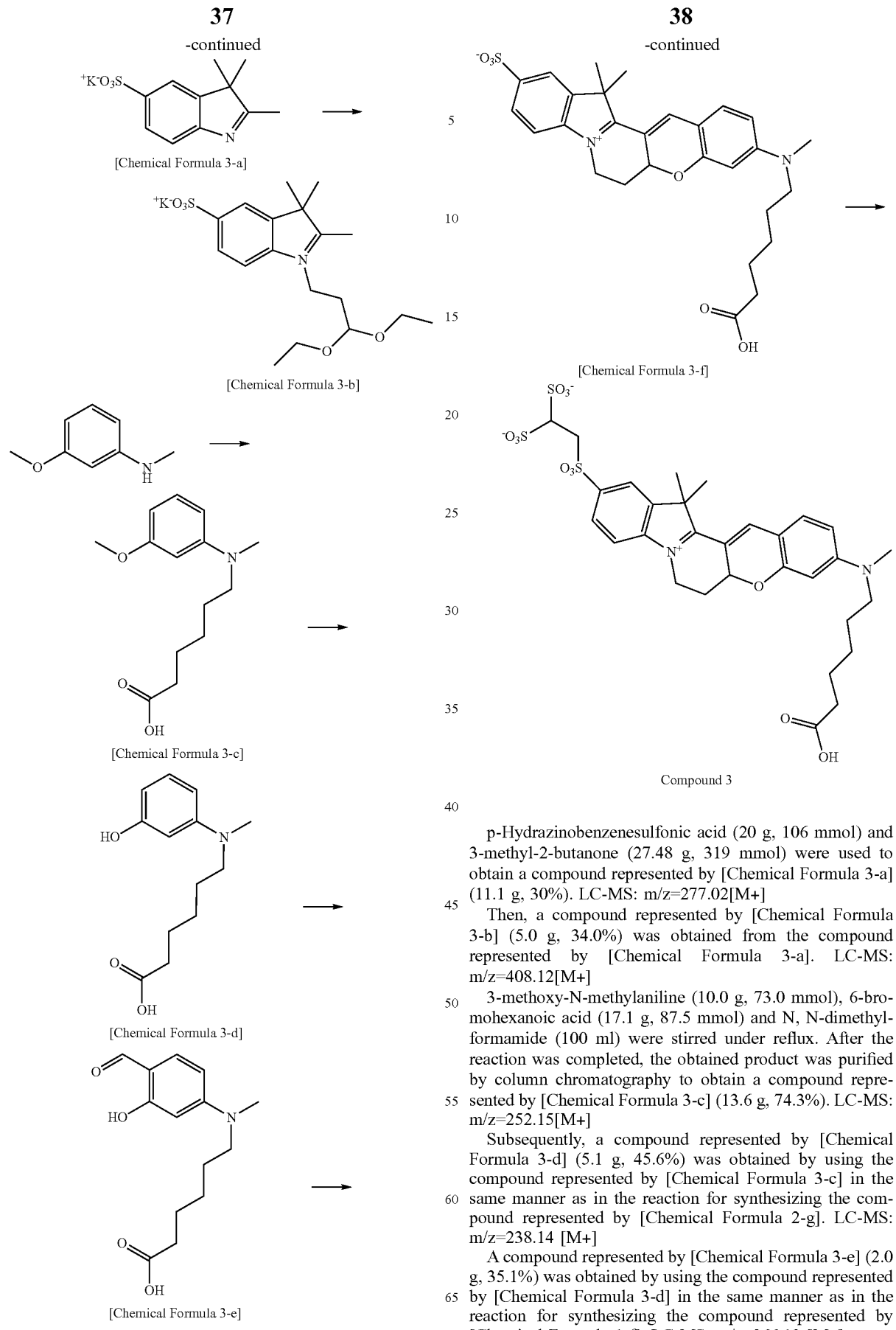

p-Hydrazinobenzenesulfonic acid (20 g, 106 mmol) and 3-methyl-2-butanone (27.48 g, 319 mmol) were used to obtain a compound represented by [Chemical Formula 3-a] (11.1 g, 30%). LC-MS: m/z=277.02[M+]

Then, a compound represented by [Chemical Formula 3-b] (5.0 g, 34.0%) was obtained from the compound represented by [Chemical Formula 3-a]. LC-MS: m/z=408.12[M+]

3-methoxy-N-methylaniline (10.0 g, 73.0 mmol), 6-bromohexanoic acid (17.1 g, 87.5 mmol) and N, N-dimethylformamide (100 ml) were stirred under reflux. After the reaction was completed, the obtained product was purified by column chromatography to obtain a compound represented by [Chemical Formula 3-c] (13.6 g, 74.3%). LC-MS: m/z=252.15[M+]

Subsequently, a compound represented by [Chemical Formula 3-d] (5.1 g, 45.6%) was obtained by using the compound represented by [Chemical Formula 3-c] in the same manner as in the reaction for synthesizing the compound represented by [Chemical Formula 2-g]. LC-MS: m/z=238.14 [M+]

A compound represented by [Chemical Formula 3-e] (2.0 g, 35.1%) was obtained by using the compound represented by [Chemical Formula 3-d] in the same manner as in the reaction for synthesizing the compound represented by [Chemical Formula 1-f]. LC-MS: m/z=266.13 [M+]

A compound (0.46 g, 23.5%) was synthesized by using the compound represented by [Chemical Formula 3-b] and the compound represented by [Chemical Formula 3-e] in the same manner as in the reaction for synthesizing the compound 1. LC-MS: m/z=525.20[M+]

The compound represented by [Chemical Formula 3-b] (1.0 g, 1.9 mmol) was dissolved in 1.0 ml of N,N-dimethylformamide, 0.5 ml of phosphonyl chloride was added, and the mixture was heated. 2-Aminoethane-1,1-disulfonic acid was added thereto, followed by stirring at room temperature. Subsequently, column purification was performed to synthesize a compound 3 (0.2 g, 15.2%). LC-MS: m/z=696.14 [M+]

Preparation Example 4. Synthesis of Compound 4

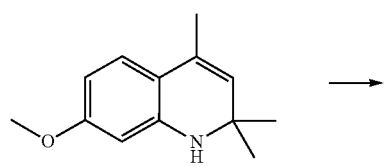

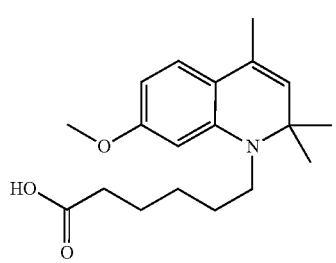

[Chemical Formula 4-a]

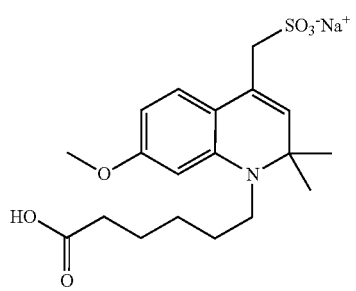

[Chemical Formula 4-b]

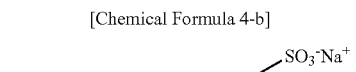

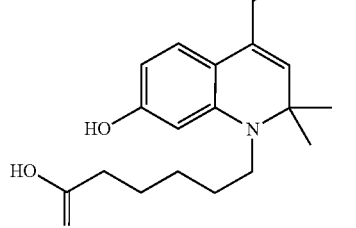

[Chemical Formula 4-c]

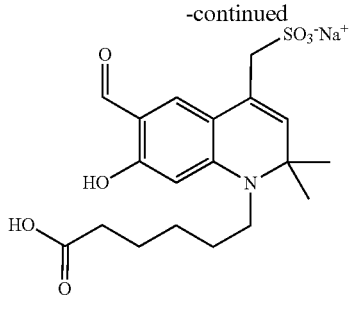

[Chemical Formula 4-d]

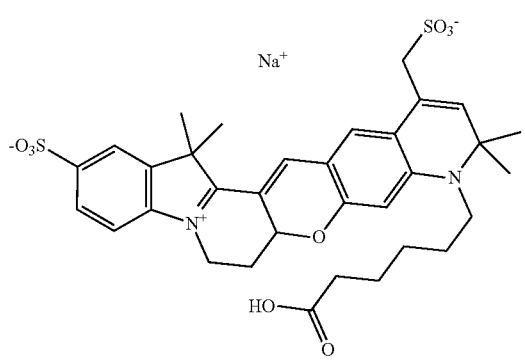

Compound 4

A compound represented by [Chemical Formula 4-a] (15.0 g, 52.6%) was obtained by using 7-methoxy-2,2-4-trimethyl-1,2-dihydroquinoline in the same manner as in the reaction for synthesizing the compound represented by [Chemical Formula 3-c]. LC-MS: m/z=318.20[M+]

A compound represented by [Chemical Formula 4-b] (13.0 g, 65.0%) was obtained by using the compound represented by [Chemical Formula 4-a] in the same manner as in the reaction for synthesizing the compound represented by [Chemical Formula 2-e]. LC-MS: m/z=420.14 [M+]

A compound represented by [Chemical Formula 4-c] (7.2 g, 56.0%) was obtained by using the compound represented by [Chemical Formula 4-b] in the same manner as in the reaction for synthesizing the compound represented by [Chemical Formula 2-g]. LC-MS: m/z=406.12[M+]

A compound represented by [Chemical Formula 4-d] (2.5 g, 30%) was obtained by using the compound represented by [Chemical Formula 4-c] in the same manner as in the reaction for synthesizing the compound represented by [Chemical Formula 2-h]. LC-MS: m/z=434.12[M+]

A compound 4 (0.51 g, 32.0%) was synthesized by using the compound represented by [Chemical Formula 3-b] and the compound represented by [Chemical Formula 4-d] in the same manner as in the reaction for synthesizing the compound represented by [Chemical Formula 3-f]. LC-MS: m/z=693.18[M+]

41

Preparation Example 5. Synthesis of Compound 35

(1) Synthesis of Compound Represented by [Chemical Formula 35-a]

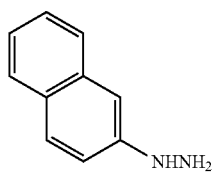

Reactant 1

+

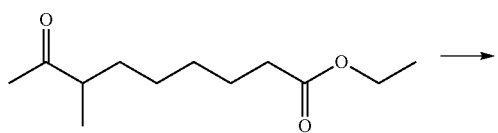

Reactant 2

→

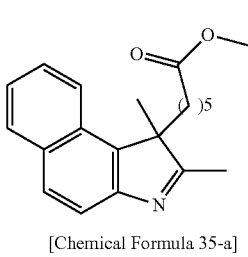

[Chemical Formula 35-a]

A reactant 1 and a reactant 2 were added to 86 ml of ethanol, 21.5 ml of hydrochloric acid was added, and the mixture was stirred under reflux for 12 hours. The reaction mixture was cooled to room temperature, 50 ml of ethyl acetate was added, and the resulting solid was filtered, washed with ethyl acetate, and dried under reduced pressure. The reaction mixture was extracted with dichloromethane and 2N aqueous sodium hydroxide solution, the organic layer was dried under reduced pressure and purified by silica column to obtain a compound represented by [Chemical Formula 35-a] (8.5 g, 40%).

H NMR (400 MHz, CDCl3): δ=7.92 (2H, dd), 7.81 (1H, d), 7.76 (1H, d), 7.49 (1H, t), 7.39 (1H, t), 4.01 (2H, q), 2.38 (1H, m) 2.32 (3H, s), 2.04 (2H, t), 1.97 (1H, m), 1.47 (3H, s), 1.35 (2H, m), 1.16 (3H, t), 1.07 (2H, m), 0.58 (1H, m), 0.39 (1H, m)

(2) Synthesis of Compound Represented by [Chemical Formula 35-b]

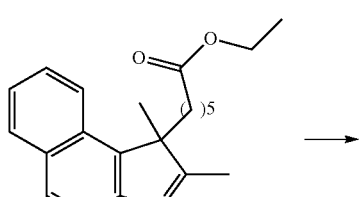

[Chemical Formula 35-a]

→

42

-continued

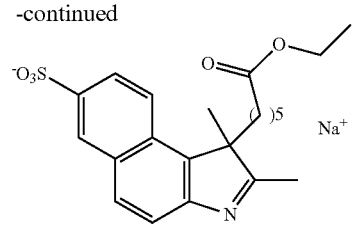

[Chemical Formula 35-b]

10 g (30 mmol) of the compound represented by [Chemical Formula 35-a] and 5 ml of the sulfuric acid solution were added, and the obtained mixture was heated and stirred at 180° C. After 2 hours, the reaction mixture was cooled to room temperature, and the reaction solution was poured into ice. 5 ml of a 50% sodium hydroxide solution was slowly added dropwise. After stirring at room temperature for 24 hours, the resulting precipitate was filtered and 5 ml of a saturated aqueous sodium sulfate solution was added to the filtrate. The resulting precipitate was filtered and the solid was recrystallized twice with water. The obtained solid was vacuum dried to obtain a compound represented by [Chemical Formula 35-b] (8 g, 60%).

(3) Synthesis of Compound Represented by [Chemical Formula 35-c]

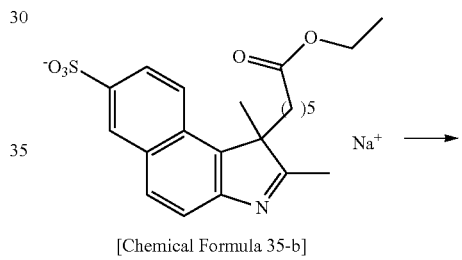

[Chemical Formula 35-b]

→

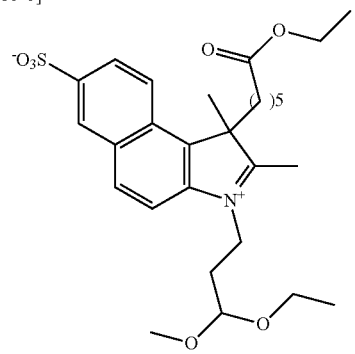

[Chemical Formula 35-c]

The compound (8 g, 28 mmol) represented by [Chemical Formula 35-b] was stirred together with 400 ml of ethanol under a nitrogen atmosphere at room temperature, and a 48% aqueous hydrochloric acid solution (80 ml) was added dropwise. After 1 hour, the reaction solution was distilled under reduced pressure. Acetonitrile (320 ml), acetic acid (8 ml) and acrolein diethyl acetal (65.72 g, 505 mmol) were added to a reactor distilled under reduced pressure, and reacted at 70° C. for 2 hours. The reaction solution was subjected to distillation under reduced pressure, and purified with a water/acetonitrile (0.1% trifluoroacetic acid) developing solution (20 ml/min, 10 to 100%) of by HPLC Rainin Dynamax C18, 8 μm column for 60 minutes, thereby obtaining a compound represented by [Chemical Formula 35-c].

(4) Synthesis of Compound Represented by [Chemical Formula 35-d]

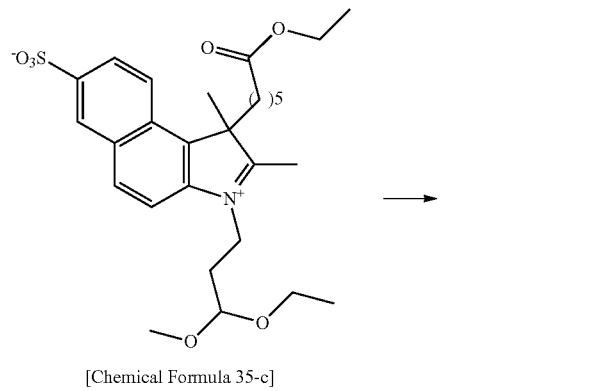

[Chemical Formula 35-c]

[Chemical Formula 35-d]

2 g (4.7 mmol) of the compound represented by [Chemical Formula 35-c] and 0.58 g (4.7 mmol) of 2,4-dihydroxy benzaldehyde were added to 20 ml of ethanol, refluxed and stirred for 3 hours. The reaction mixture was cooled to room temperature, distilled under reduced pressure, and purified by silica column. 10 ml of chloroform and 1 ml of 50% aqueous sulfuric acid solution were added to the purified material, and the mixture was stirred at room temperature for 20 minutes. The pH of the mixture was adjusted to 7 to 8 using a normal sodium hydroxide solution, and the mixture was extracted with methylene chloride. After distillation under reduced pressure, the obtained product was purified by silica column to obtain a compound represented by [Chemical Formula 35-d] (0.3 g, 15%).

(5) Synthesis of Compound 35

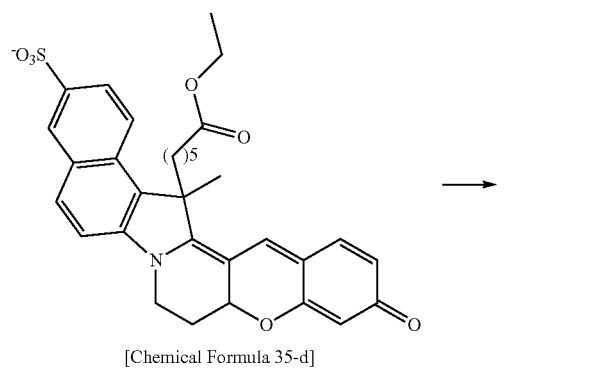

[Chemical Formula 35-d]

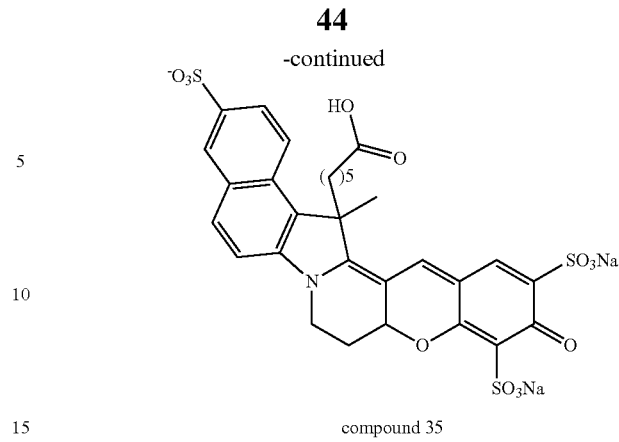

compound 35

0.3 g (30 mmol) of the compound represented by [Chemical Formula 35-d] and 1 ml of the sulfuric acid solution were added, and the obtained mixture was heated and stirred at 40° C. After 2 hours, the reaction mixture was cooled to room temperature, and the reaction solution was poured into ice. 50% sodium hydroxide solution was slowly added dropwise to neutralize the mixture. The neutralized product was purified with a water/acetonitrile (0.1% trifluoroacetic acid) developing solution (20 ml/min, 10 to 100%) of by HPLC Rainin Dynamax C18, 8 μm column for 60 minutes, thereby synthesizing a compound 35.

1H NMR (400 MHz, MeOD): δ=8.13 (2H, m), 7.97 (3h, m), 7.72 (2H, m), 5.48 (1H, m), 4.65 (1H, m) 4.43 (1H, m), 2.98 (1H, m), 2.61 (1H, m), 2.44 (1H, m), 2.24 (1H, m), 1.77 (3H, d), 1.70 (2H, m), 0.85 (4H, m) 0.46 (1H, m), −0.01 (1H, m)

Preparation Example 6. Synthesis of Compound 48

A compound 48 was synthesized in the same manner as in the synthesis of Compound 35.

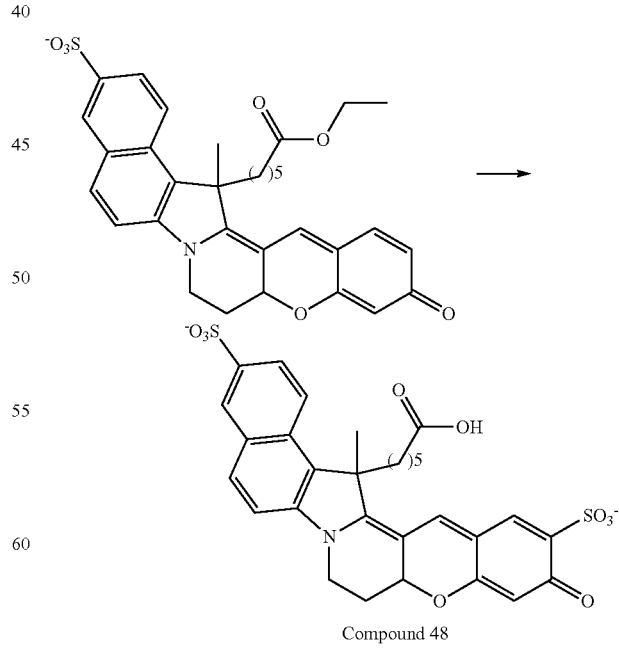

Compound 48

1H NMR (400 MHz, DMSO): δ=8.62 (1H, s), 8.40 (1H, m), 8.31 (1H, m), 8.37 (1H, d), 7.99 (1H, dd), 7.92 (1H, d), 8.05 (1H, s), 6.43 (1H, s), 5.48 (1H, m), 4.84 (1H, m), 4.42 (1H, m), 2.80 (5H, m), 2.58 (1H, m), 1.98 (3H, s), 1.95 (2H, t), 1.20 (1H, m), 1.04 (1H, m), 0.76 (1H, m), 0.25 (1H, m)

Preparation Example 7. Synthesis of Compound 49

(1) Synthesis of Compound Represented by [Chemical Formula 49-a]

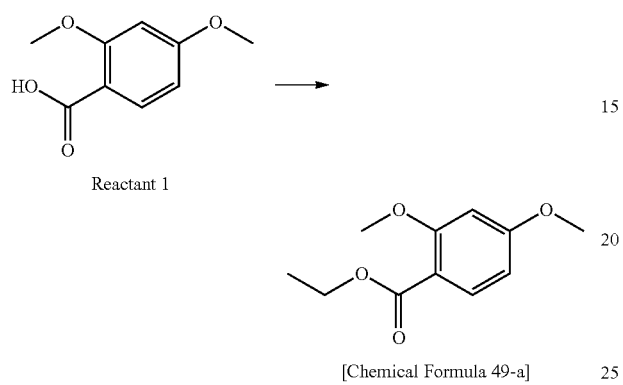

[Chemical Formula 49-a]

100 ml of ethanol was cooled to 0° C., 7 ml of thionyl chloride was slowly added dropwise, and the mixture was stirred for 10 minutes. 10 g (0.05 mole) of the compound represented by reactant 1 was dissolved in ethanol, and the mixture was slowly added dropwise and stirred at room temperature. The product was concentrated under reduced pressure and then dried to obtain a compound represented by [Chemical Formula 49-a].

(2) Synthesis of Compound Represented by [Chemical Formula 49-b]

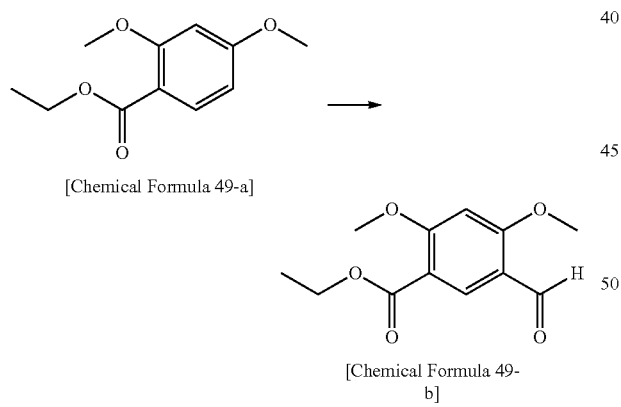

[Chemical Formula 49-b]

4.78 ml (65.4 mmole) of dimethoxyformamide was slowly added dropwise to 4.01 ml (26 mmole) of phosphoryl chloride, and the mixture was stirred at room temperature for 2 hours. 5 g (24 mmole) of the compound represented by [Chemical Formula 49-a] was dissolved in 12.5 ml of dimethoxyformamide, slowly dropped into the reaction solution, and stirred for 24 hours. The reaction solution was slowly added dropwise to excess water. The precipitated solid was filtered under reduced pressure and purified by silica column to obtain a compound represented by [Chemical Formula 49-b].

(3) Synthesis of Compound Represented by [Chemical Formula 49-c]

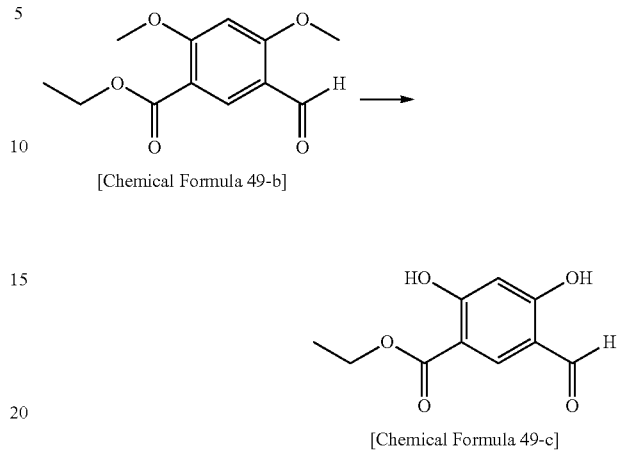

[Chemical Formula 49-c]

8 g (34 mmole) of the compound represented by [Chemical Formula 49-b] was added to 200 ml of dichloromethane and stirred. 13.44 g (101 mmole) of aluminum chloride was slowly added dropwise, and the mixture was heated and stirred at 40° C. for 24 hours. After cooling to room temperature, 100 ml of a 6N aqueous hydrochloric acid solution was added dropwise, and the mixture was extracted and purified by silica column to obtain a compound represented by [Chemical Formula 49-c] (4.3 g, 59%).

(4) Synthesis of Compound Represented by [Chemical Formula 49-d]

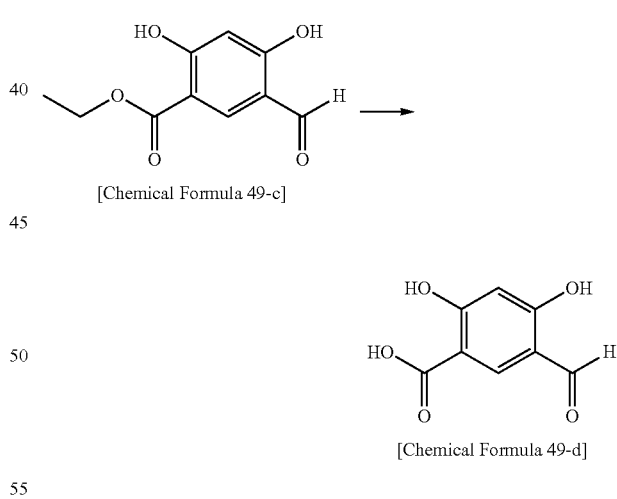

[Chemical Formula 49-d]

0.6 g (34 mmole) of the compound represented by [Chemical Formula 49-c] was added to a solvent in which methanol, tetrahydrofuran and water each having an amount of 11 ml, were mixed, and stirred. 3.8 g (9 mmole) of lithium hydroxide monohydrate was added and stirred for 24 hours. The pH was lowered to 4 or less using a 1N aqueous hydrochloric acid solution, and the reaction mixture was extracted with methylene chloride. After distillation under reduced pressure, the obtained product was purified by silica column to obtain a compound represented by [Chemical Formula 49-d].

47

(5) Synthesis of Compound Represented by [Chemical Formula 49-e]

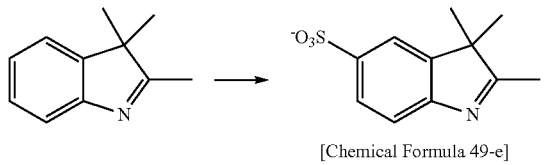

[Chemical Formula 49-e]

The compound represented by [Chemical Formula 49-e] was synthesized in the same manner as in the reaction for synthesizing the compound represented by [Chemical Formula 35-c].

(6) Synthesis of Compound Represented by [Chemical Formula 49-f]

The compound represented by [Chemical Formula 49-f] was synthesized in the same manner as in the reaction for synthesizing the compound represented by [Chemical Formula 35-d].

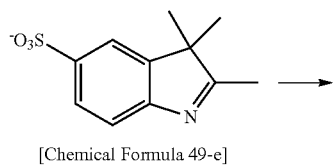

[Chemical Formula 49-e]

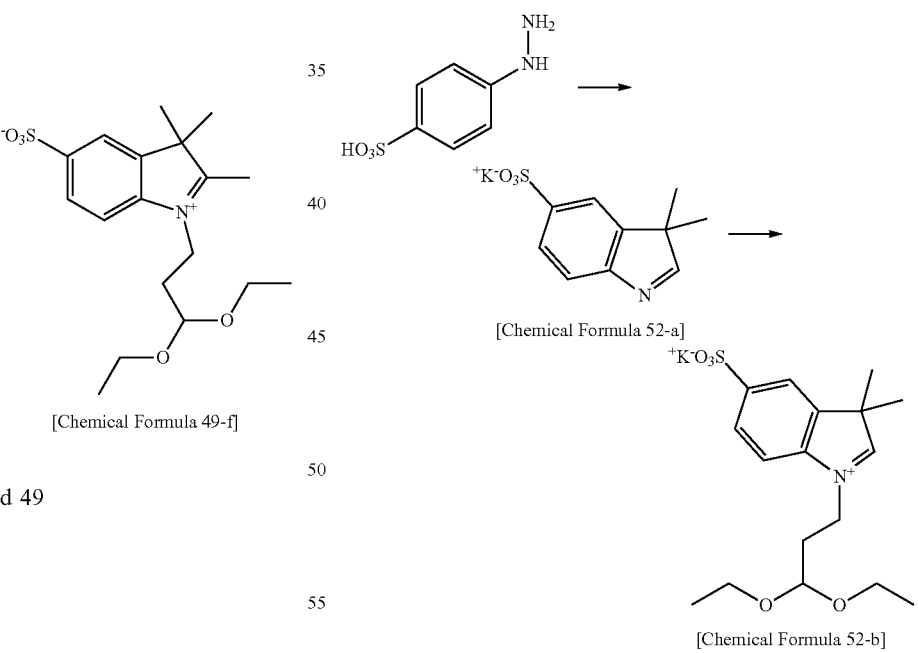

[Chemical Formula 49-f]

(7) Synthesis of Compound 49

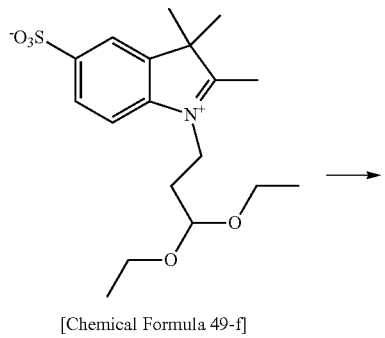

[Chemical Formula 49-f]

48

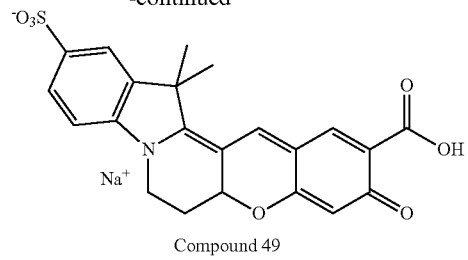

Compound 49

2 g (4.7 mmol) of the compound represented by [Chemical Formula 49-f] and 0.58 g (4.7 mmol) of 2,4-dihydroxy benzaldehyde were added to 20 ml of ethanol, refluxed and stirred for 3 hours. The reaction mixture was cooled to room temperature, distilled under reduced pressure, and purified by silica column. 10 ml of chloroform and 1 ml of 50% aqueous sulfuric acid solution were added to the purified material, and the mixture was stirred at room temperature for 20 minutes. The pH of the mixture was adjusted to 7 to 8 using a normal sodium hydroxide solution, and the mixture was extracted with methylene chloride. After distillation under reduced pressure, the obtained product was purified by silica column to synthesize a compound 49.

Preparation Example 8. Synthesis of Compound 52

(1) Synthesis of Compound Represented by [Chemical Formula 52-b]

[Chemical Formula 52-a]

[Chemical Formula 52-b]

p-Hydrazinobenzenesulfonic acid (20 g, 106 mmol) and 3-methyl-2-butanone (27.48 g, 319 mmol) were added to 30 ml of 6N aqueous hydrochloric acid solution/60 ml of ethanol, and stirred under reflux for 12 hours. The mixture was cooled to room temperature, and the resulting solid was filtered. The filtrate was washed with ethyl acetate and dried under reduced pressure. Potassium hydroxide (1.4 g, 25.4 mmol) was dissolved in 35 ml of propanol and the filtered solid (5.1 g, 21.2 mmol) was dissolved in 35 ml of methanol and added dropwise. The mixture was stirred at room temperature for 12 hours. The solid was filtered and dried. The product was purified by C18 reverse phase chromatography to obtain a compound represented by [Chemical Formula 52-a] (11.1 g, 30%).

The compound (2.0 g, 7.4 mmol) represented by [Chemical Formula 52-a] was stirred together with ethanol under a nitrogen atmosphere at room temperature, and a 48% aqueous hydrochloric acid solution (10.0 ml) was added dropwise. After 1 hour, the reaction solution was distilled under reduced pressure. Acetonitrile (120.0 ml), acetic acid (3.0 ml) and acrolein diethyl acetal (17.3 g, 133.0 mmol) were added to a reactor distilled under reduced pressure, and reacted at 70° C. for 2 hours. The reaction solution was subjected to distillation under reduced pressure and purified with a water/acetonitrile (0.1% trifluoroacetic acid) developing solution (20 ml/min, 10 to 100%) of by HPLC Rainin Dynamax C18, 8 µm column for 60 minutes, thereby obtaining a compound represented by [Chemical Formula 52-b] (0.9 g, 30%).

(2) Synthesis of Compound Represented by [Chemical Formula 52-c]

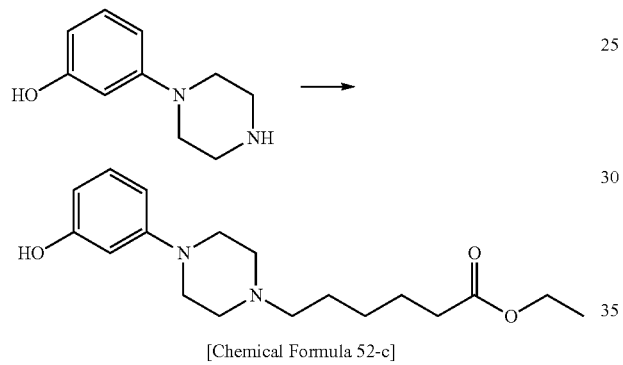

[Chemical Formula 52-c]

3-(1-Piperazinyl)phenol (10 g, 0.056 mol), 6-bromohexanoate (12.5 g, 0.056 mol) and diisopropylethylamine (14.5 g, 0.112 mol) were added to 100 ml of acetonitrile and stirred at 60° C. The mixture was reacted for 24 hours, and cooled at room temperature. The reaction product was poured into water and extracted with methylene chloride. The moisture was removed with magnesium sulfate, the solid was filtered, and the filtrate was concentrated and purified by column (13 g, 72%).

(3) Synthesis of Compound Represented by [Chemical Formula 52-d]

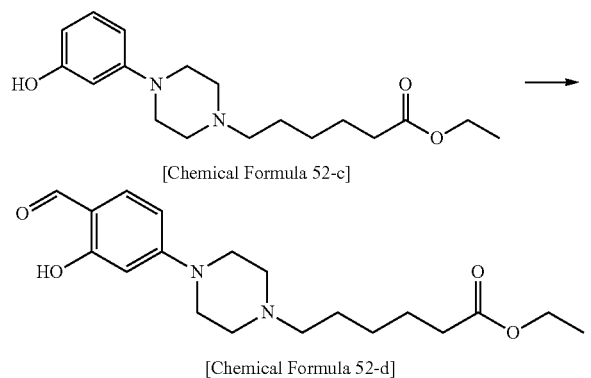

[Chemical Formula 52-c]

[Chemical Formula 52-d]

The reactor was charged with 50 ml of n-dimethylformamide and cooled to 0° C., and phosphorus oxychloride (2.6 g, 0.017 mol) was added dropwise. The mixture was stirred for 10 minutes, and a compound represented by [Chemical Formula 1] (5 g, 0.016 mol) was diluted in n-dimethylformamide and added dropwise. The reaction was performed at 50° C. for 12 hours, and the obtained reaction product was cooled to room temperature. The reaction product was poured into ice water, neutralized with 1M aqueous sodium hydroxide solution and extracted with ethyl acetate. The solution was concentrated under reduced pressure and purified by silica column (4.59 g, 85%).

(4) Synthesis of Compound Represented by [Chemical Formula 52-e]

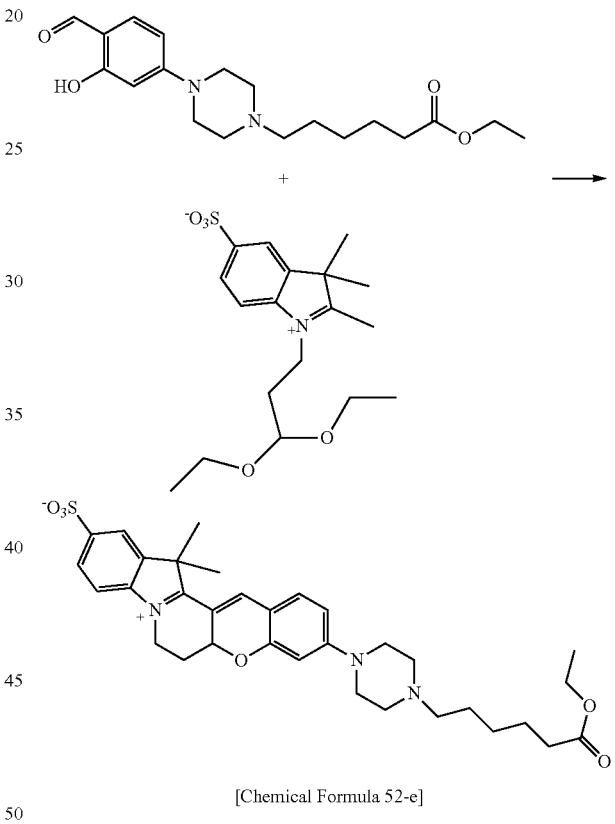

[Chemical Formula 52-e]

The compound (0.8 g, 1.9 mmol) represented by [Chemical Formula 52-b] and the compound represented by [Chemical Formula 52-d] (0.7 g, 1.9 mmol) were dissolved in 20 ml of ethanol and stirred at 80° C. for 8 hours. After the reaction was completed, the solvent was removed by concentration under reduced pressure. The concentrated reaction product was dissolved in 50 ml of chloroform, and 1 ml of 50% sulfuric acid was added dropwise. The obtained product was diluted with dichloromethane and extracted with water. The organic layer was concentrated under reduced pressure and purified with a water/acetonitrile (0.1% trifluoroacetic acid) developing solution (20 ml/min, 10 to 100%) of by HPLC Rainin Dynamax C18, 8 µm column for 60 minutes (0.4 g, 51%). LC-MS: m/z=579.24 [M+]

(5) Synthesis of Compound 52

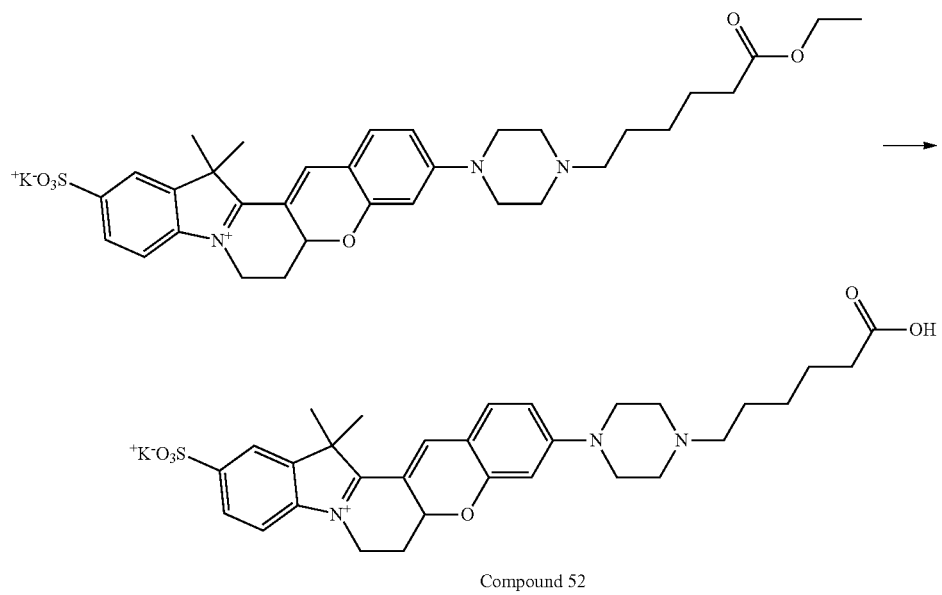

Compound 52

The compound (0.5 g, 0.0008 mol) represented by [Chemical Formula 52-e] and methanol (10 ml) were placed in a reactor and stirred at room temperature. Potassium hydroxide (0.09 g, 0.0016 mol) and 5 ml of water were mixed to prepare a solution. The solution was injected into the reactor, reacted at 55° C. for 2 hours, and then cooled at room temperature. The reaction mixture was neutralized to pH 6-7 with 2N HCl aqueous solution, and extracted with methylene chloride. The solvent was removed and the product was purified by column (0.45 g, 98%). LC-MS: m/z=618.20[M+]

Preparation Examples 9 and 10. Synthesis of Compound 53 and Compound 54

(1) Synthesis of Compound Represented by [Chemical Formula 53-a]

The compound represented by [Chemical Formula 53-a] was obtained in the same manner as in the reaction for synthesizing the compound represented by [Chemical Formula 35-a].

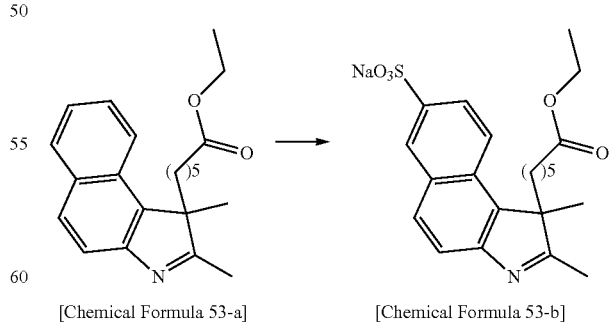

-continued

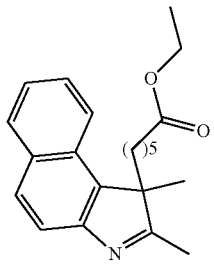

[Chemical Formula 53-a]

H NMR (400 MHz, CDCl3): δ=7.92 (2H, dd), 7.81 (1H, d), 7.76 (1H, d), 7.49 (1H, t), 7.39 (1H, t), 4.01 (2H, q), 2.38 (1H, m) 2.32 (3H, s), 2.04 (2H, t), 1.97 (1H, m), 1.47 (3H, s), 1.35 (2H, m), 1.16 (3H, t), 1.07 (2H, m), 0.58 (1H, m), 0.39 (1H, m)

(2) Synthesis of Compound Represented by [Chemical Formula 53-b]

[Chemical Formula 53-a]   [Chemical Formula 53-b]

10 g (30 mmol) of the compound represented by [Chemical Formula 53-a] and 5 ml of the sulfuric acid solution were added, and the obtained mixture was heated and stirred at 180° C. After 2 hours, the reaction mixture was cooled to room temperature, and the reaction solution was poured into ice. 5 ml of a 50% sodium hydroxide solution was slowly added dropwise. After stirring at room temperature for 24 hours, the resulting precipitate was filtered and 5 ml of a saturated aqueous sodium sulfate solution was added to the filtrate. The resulting precipitate was filtered, the solid was recrystallized twice with water, and the obtained solid was vacuum dried (8 g, 60%).

(3) Synthesis of Compound Represented by [Chemical Formula 53-c]

The compound represented by [Chemical Formula 53-c] was obtained in the same manner as in the reaction for synthesizing the compound represented by [Chemical Formula 35-c].

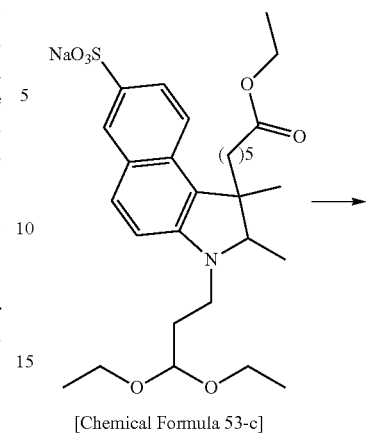

[Chemical Formula 53-c]

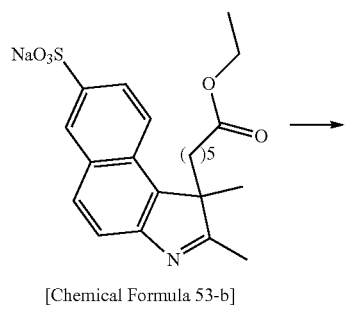

[Chemical Formula 53-b]

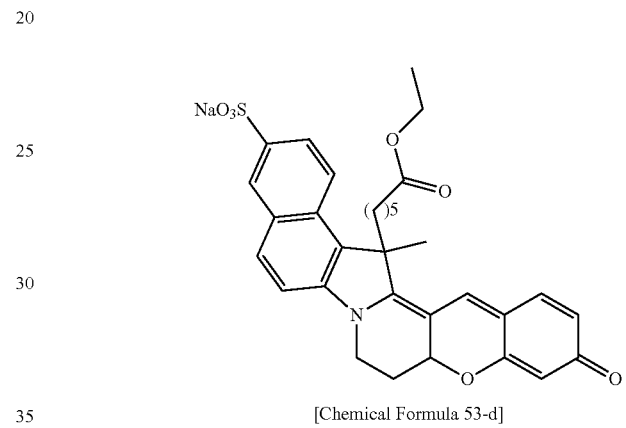

[Chemical Formula 53-d]

(5) Synthesis of Compound 53 and Compound 54

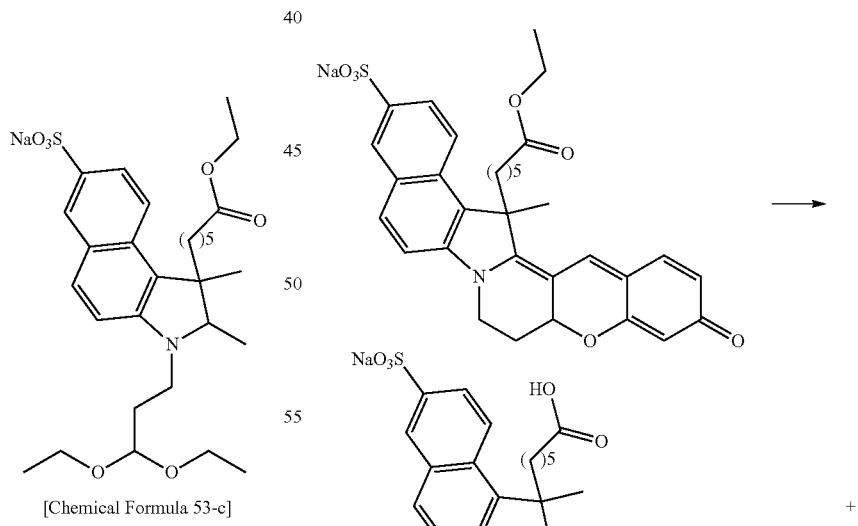

Compound 53

(4) Synthesis of Compound Represented by [Chemical Formula 53-d]

The compound represented by [Chemical Formula 53-d] was obtained in the same manner as in the reaction for synthesizing the compound represented by [Chemical Formula 35-d].

[Chemical Formula 53-c]

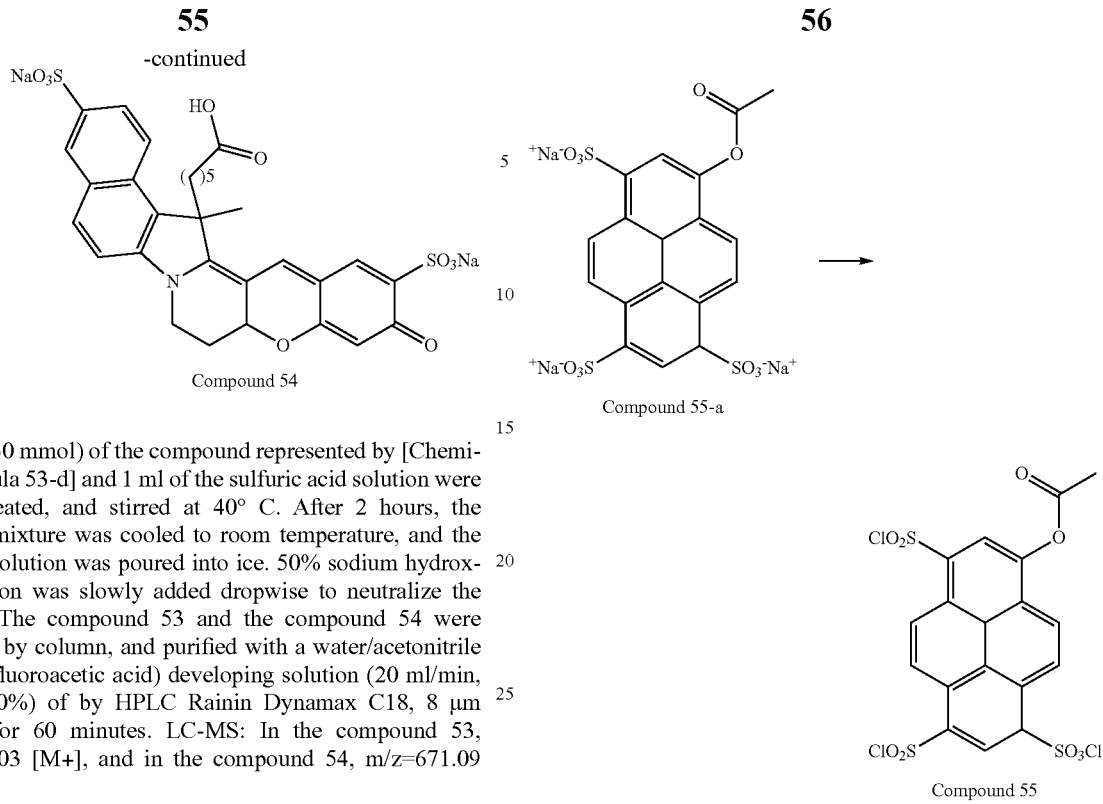

Compound 54

0.3 g (30 mmol) of the compound represented by [Chemical Formula 53-d] and 1 ml of the sulfuric acid solution were added, heated, and stirred at 40° C. After 2 hours, the reaction mixture was cooled to room temperature, and the reaction solution was poured into ice. 50% sodium hydroxide solution was slowly added dropwise to neutralize the mixture. The compound 53 and the compound 54 were separated by column, and purified with a water/acetonitrile (0.1% trifluoroacetic acid) developing solution (20 ml/min, 10 to 100%) of by HPLC Rainin Dynamax C18, 8 μm column for 60 minutes. LC-MS: In the compound 53, m/z=773.03 [M+], and in the compound 54, m/z=671.09 [M+]

Preparation Example 11. Method for Preparing Compound 55

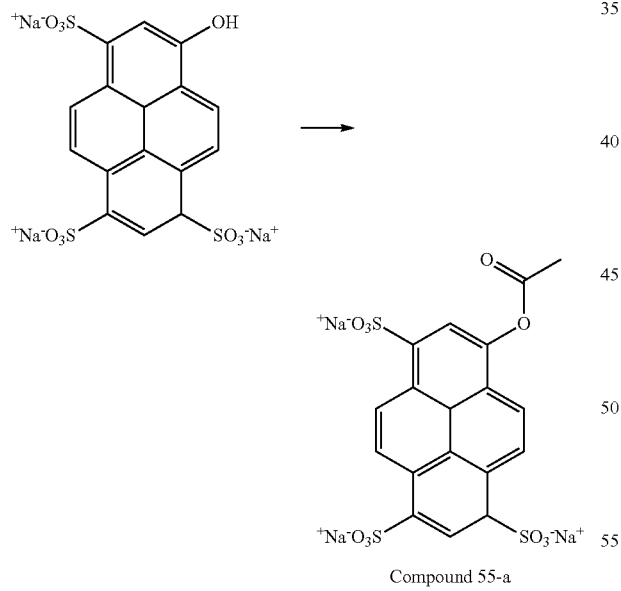

HPTS (8-Hydroxypyrene-1,3,6-trisulfonic acid trisodium salt) (10 g, 0.019 mol), sodium acetate (1.64 g, 0.02 mol), and 100 ml of acetic anhydride were placed in a reactor and stirred at room temperature. After complete dispersion, the mixture was heated and stirred under reflux for 35 hours. After the reaction was confirmed, the reaction product was cooled to room temperature, diluted with tetrahydrofuran, and filtered, and the solid was washed. The solid was washed once with acetone and dried. Gray powder (8.2 g, 76%)

Compound 55-a (8 g, 0.014 mol) and thionyl chloride (80 ml) were placed in a reactor and stirred at room temperature. The reactor was charged with dimethylformamide (0.216 g, 0.003 mol) and refluxed for 5 hours. After the reaction was confirmed, the reaction product was cooled at room temperature, and slowly poured into ice water. The resulting solid was filtered and washed several times with water. The solid in which the washing was completed was dried to obtain a compound 55 (7 g, 90%).

Preparation Example 12. Fluorogenic pH-Sensitive Dye

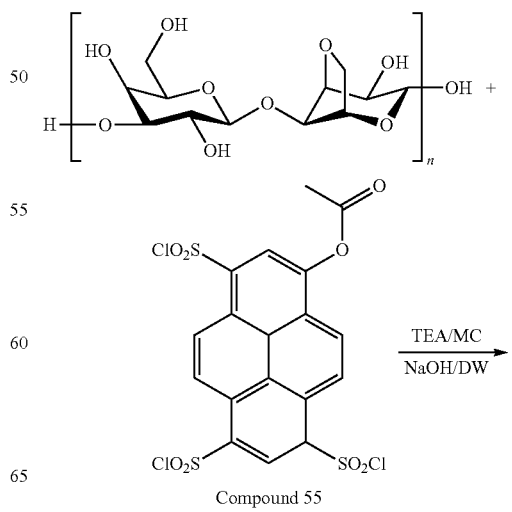

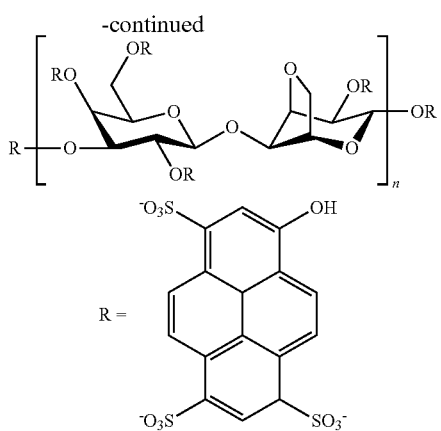

1 g of agarose was dispersed in 5 ml of methylene chloride (MC), 1 g of triethylamine (TEA) was added, and the mixture was stirred at room temperature for 30 minutes. Then, the temperature was lowered to 0° C., and 0.5 g of the compound 55 was added thereto. Here, the solution turned from orange to brown. The solution was reacted at room temperature for 2 hours, and then the reaction product was filtered, washed sufficiently with methylene chloride, and dried to obtain a brown powder.

The brown powder was placed in a reaction vessel and dispersed in water, and the solution was made into a basic solution of about pH 8 to 10 with aqueous NaOH solution. The solution was reacted at room temperature for 2 hours to obtain fluorescent orange powder. The powder solid was filtered, washed thoroughly with water, and dried, and then the solid was dissolved in a small amount of water to form a gel.

Preparation Example 13. Fluorogenic pH-Sensitive Dye

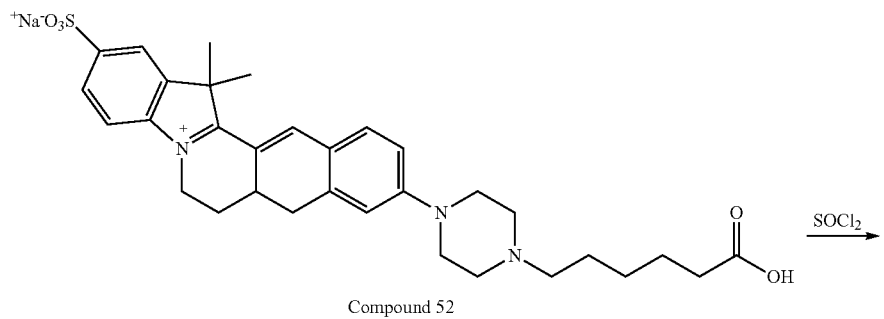

Compound 52

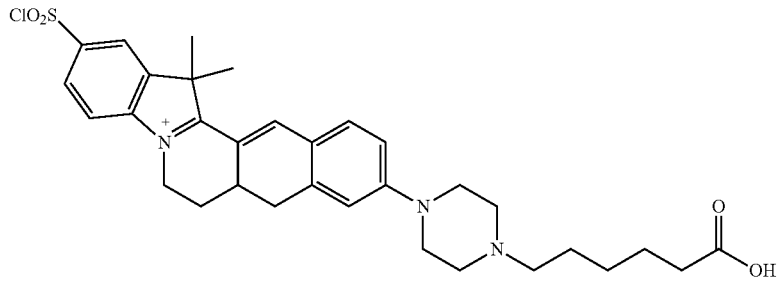

The compound 52 (2 g, 0.003 mol) was dispersed in 10 ml of thionyl chloride. DMF (0.05 g, 0.0007 mol) was added thereto, followed by refluxing and stirring for 5 hours. The reaction was confirmed by TLC and cooled to room temperature. The reaction product was slowly poured into ice and stirred. The solid was filtered after waiting until there was no temperature change. The filtrate was washed with water sufficiently and dried (1.4 g, yield: 70%).

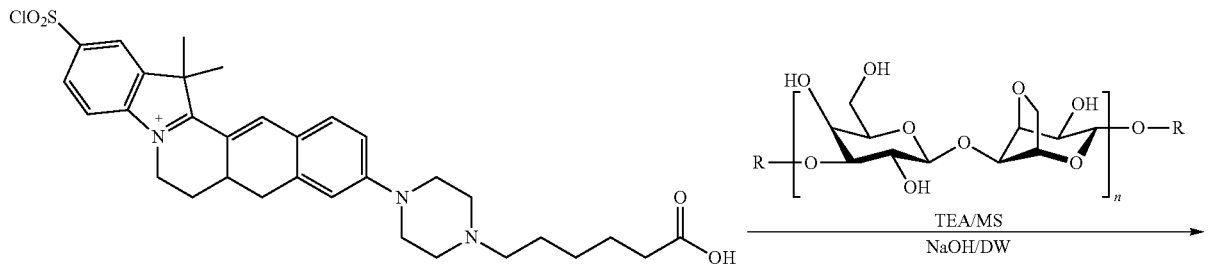

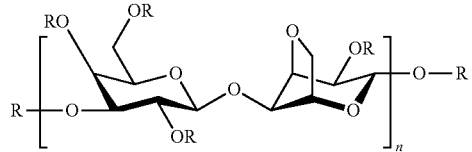

R =

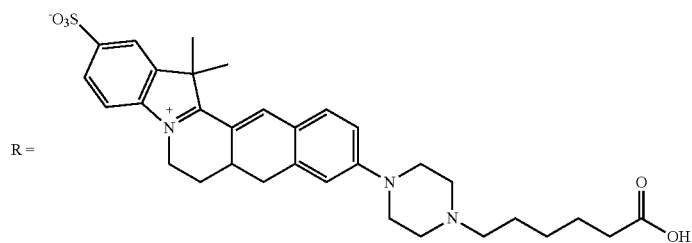

1 g of agarose was dispersed in 5 ml of methylene chloride (MC), 1 g of triethylamine (TEA) was added, and the mixture was stirred at room temperature for 30 minutes. Then, the temperature was lowered to 0° C., and 0.5 g of the compound 12-a was added thereto. The solution was reacted at room temperature for 2 hours, and then the reaction product was filtered, washed sufficiently with methylene chloride, and dried to obtain a brown powder.

The brown powder was placed in a reaction vessel and dispersed in water, and the solution was made into a basic solution of about pH 8 to 10 with aqueous NaOH solution. The solution was reacted at room temperature for 2 hours to obtain fluorescent red powder. The powder solid was filtered, washed thoroughly with water, and dried, and then the solid was dissolved in a small amount of water to form a gel.

Preparation Example 14. Fluorogenic pH-Sensitive Dye

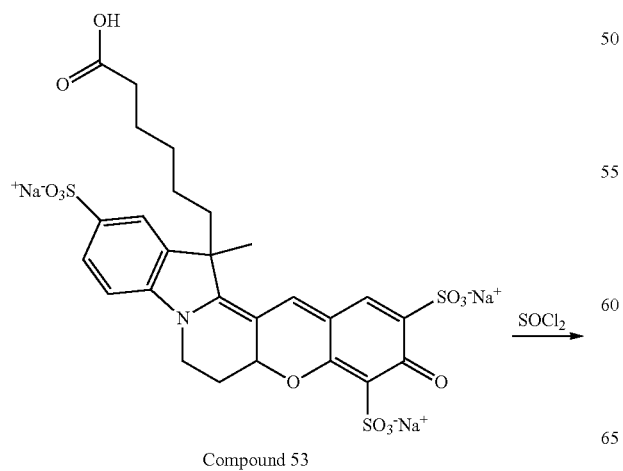

Compound 53

$\xrightarrow{SOCl_2}$

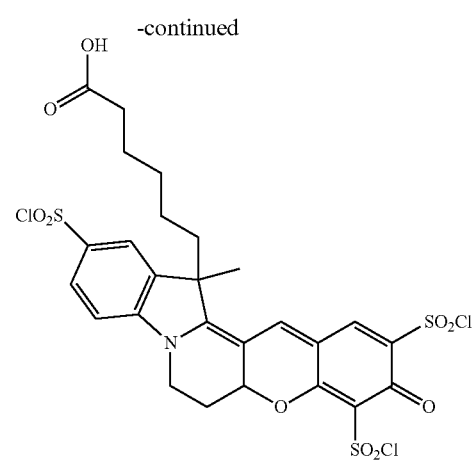

The compound 53 (1.8 g, 0.0025 mol) was dispersed in 9 ml of thionyl chloride. DMF (0.038 g, 0.0005 mol) was added thereto, followed by refluxing and stirring for 5 hours. The reaction was confirmed by TLC and cooled to room temperature. The reaction product was slowly poured into ice and stirred, and the solid was filtered after waiting until there was no temperature change. The filtrate was washed with water sufficiently and dried (1.2 g, yield: 67%).

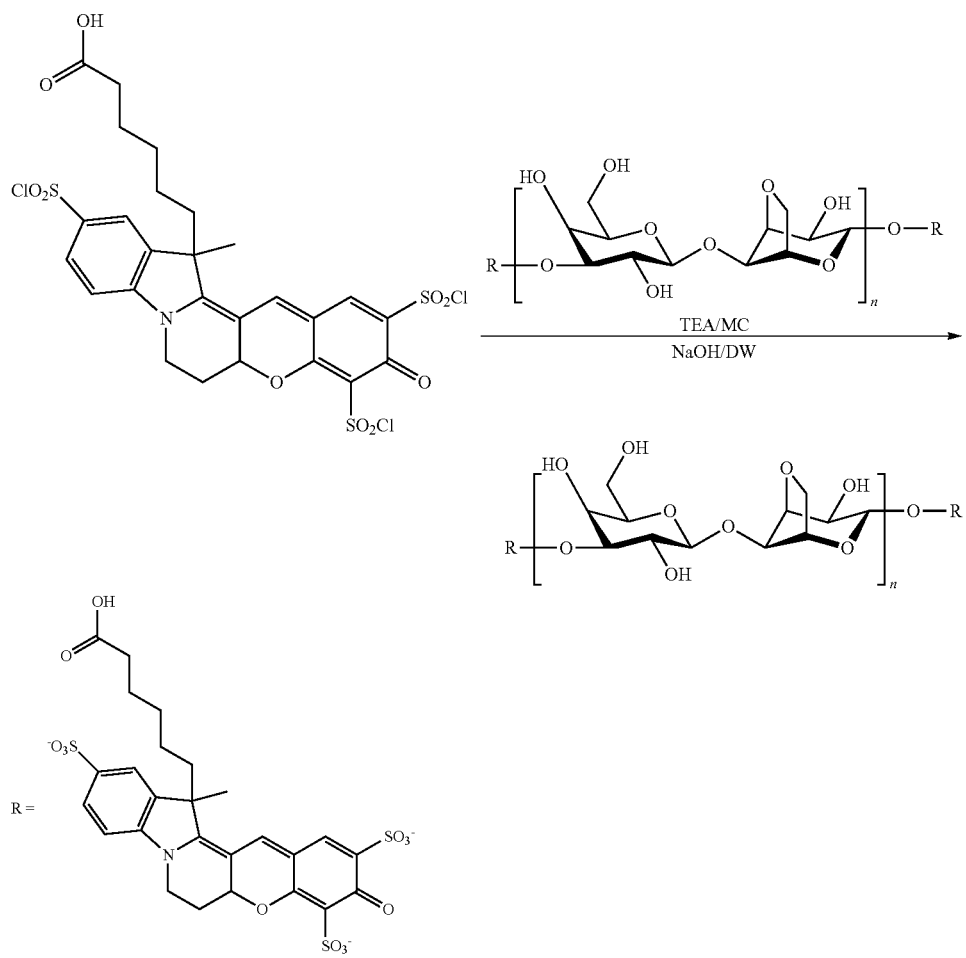

1 g of agarose was dispersed in 5 ml of methylene chloride (MC), 1 g of triethylamine (TEA) was added, and the mixture was stirred at room temperature for 30 minutes. Then, the temperature was lowered to 0° C., and 0.5 g of the compound 13-a was added thereto. The solution was reacted at room temperature for 2 hours, and then the reaction product was filtered, washed sufficiently with methylene chloride, and dried to obtain a brown powder.

The brown powder was placed in a reaction vessel and dispersed in water, and the solution was made into a basic solution of about pH 8 to 10 with aqueous NaOH solution. The solution was reacted at room temperature for 2 hours to obtain fluorescent pink powder. The powder solid was filtered, washed thoroughly with water, and dried, and then the solid was dissolved in a small amount of water to form a gel.

Example 1. Manufacture of Film Including Dye 0.2 g of the dye prepared by Preparation Example 12 was added to 9.8 g of distillation water (DW) to prepare a mixed solution. A reaction vessel including the mixed solution was placed on a hot plate, stirred at 200 rpm, heated at 100° C., and stirred until the dye prepared by Preparation Example 12 was completely dissolved. Then, the mixed solution was placed in a desired frame and allowed to stand at room temperature for about 30 minutes to perform gelation, thereby obtaining a yellow gel. The obtained gel was placed on a polyethylene phthalate film and pressed. Then, the film was dried in an oven at about 60° C. for 5 hours to manufacture a film.

Example 2. Manufacture of Film Including Dye

A mixed solution in which the dye prepared by Preparation Example 12 in 1 wt % of distilled water was coated on a nitrocellulose membrane and dried at room temperature for 12 hours, thereby manufacturing a film coated with the dye.

Example 3. Manufacture of Film Including Dye

A nitrocellulose membrane was immersed in a mixed solution in which the dye prepared by Preparation Example 12 was dissolved in 1 wt % of distilled water, and left at 60° C. for 12 hours. The nitrocellulose membrane immersed in the dye was taken out, the dye that was not immersed in the surface was washed with distilled water, and dried at room temperature for 12 hours to manufacture the film coated with the dye.

Example 4. Plate Coated with Dye 0.2 g of the dye prepared by Preparation Example 12 was added to 9.8 g of distillation water (DW) to prepare a mixed solution. A reaction vessel including the mixed solution was placed on a hot plate, stirred at 200 rpm, heated at 100° C., and stirred until the dye was completely dissolved. Subsequently, the mixed solution was kept at 80° C. so that the mixed solution was not gelled.

Then, the mixed solution was dropped at a desired position into each well of the plate in each amount of 5 μl, gelled at room temperature for 10 minutes, and dried in an oven at 60° C. for 5 hours to complete the coating on the plate.

Example 5. Plate Coated with Dye

The dye was coated on the plate in the same manner as in Example 2, except that the dye prepared by Preparation Example 13 was used.

Example 6. Plate Coated with Dye

The dye was coated on the plate in the same manner as in Example 2, except that the dye prepared by Preparation Example 14 was used.

Example 7. Film Including $TiO_2$ Reflective Layer Introduced Thereinto 3 ml of (3-glycidyloxypropyl)trimethoxysilane and 3 ml of methyltrimethoxysilane were added. Then, 1 ml of distilled water was added, and the mixture was stirred by sonication for 5 minutes to uniformly disperse $TiO_2$. 1 ml of 36% HCl was added dropwise, and the mixture was reacted at 50° C. for 1.5 hours, followed by bar coating on a polyethylene phthalate film. The film was dried at room temperature for 12 hours and then dried in an oven at 60° C. for 3 hours, thereby preparing a polymer film having a $TiO_2$ reflective layer.

A nitrocellulose membrane was immersed in a mixed solution in which the dye prepared by Preparation Example 12 was dissolved in 1 wt % of distilled water, and left at 60° C. for 12 hours. The nitrocellulose membrane immersed in the dye was taken out, the dye that was not immersed in the surface was washed with distilled water, and dried at room temperature for 12 hours to manufacture the film coated with the dye.

Subsequently, a transparent adhesive was applied on the film coated with the dye, and then a polymer film having the $TiO_2$ reflective layer was attached thereto, thereby manufacturing a film into which the $TiO_2$ reflective layer was introduced.

Example 8. Manufacture of Film Including Reference Dye

An acrylate resin (30% solid) and 0.1 to 1% of reference dye represented by Chemical Formula below were mixed for 24 hours, and the mixture was subjected to bar coating on a transparent polymer film (polyethylene phthalate, polystyrene, etc.) and dried to manufacture a film coated with the reference dye.

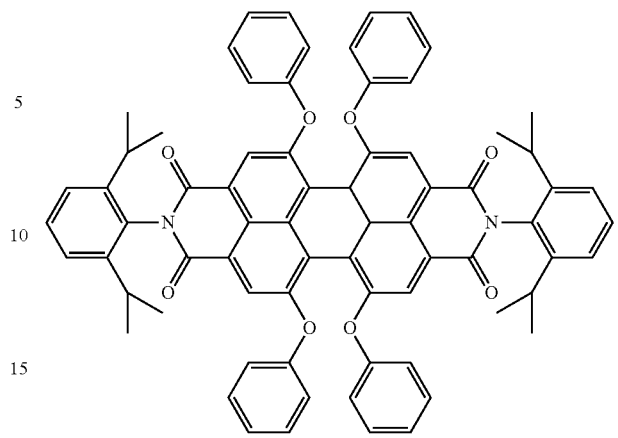

Subsequently, an adhesive was applied on the film coated with the reference dye, and the film manufactured by Example 3 was attached and dried for 12 hours, thereby manufacturing a film in which the film including the dye prepared by Preparation Example 12 and the film including the reference dye were stacked.

Experimental Example 1. Evaluation of Fluorescence Properties of Dye

The absorption spectrum (λabs), emission spectrum (λem), and quantum efficiency of the HPTS compound as a control group and the compounds 52 to 54 prepared by Preparation Examples 8 to 10 were measured and shown in Table 1 below.

TABLE 1

| Classification | Solvent | $\lambda_{abs}$(nm) | $\lambda_{em}$(nm) | Quantum efficiency |
|---|---|---|---|---|
| HPTS | Acid buffer | 411 | 533 | 1.0 |
|  | Base buffer | 466 | 533 | 1.0 |
| Compound 52 | Acid buffer | 549 | 596 | 0.53 |
|  | Base buffer | 562 | 596 | 0.53 |
| Compound 53 | Acid buffer | 475 | 585 | 0.72 |
|  | Base buffer | 564 | 585 | 0.72 |
| Compound 54 | Acid buffer | 474 | 583 | 0.68 |
|  | Base buffer | 563 | 583 | 0.68 |

Since the dye was also remarkably excellent in view of quantum efficiency, the dye exhibits stronger fluorescence to thereby be effectively utilized in a wide variety of fields such as probes for various biological systems requiring optical imaging.

Further, in order to confirm the sensitivity to the pH detection of the dye of Preparation Example 12, a phosphate buffer solution having a pH of 2 to 11 was prepared by adding 1N hydrochloric acid or sodium hydroxide solution to 0.1 M phosphoric acid buffer solution.

The fluorescence intensity of the dye in the phosphate buffer solution having a pH of 2 to 11 was measured, and the result is shown in FIG. 1.

Figure 2A:
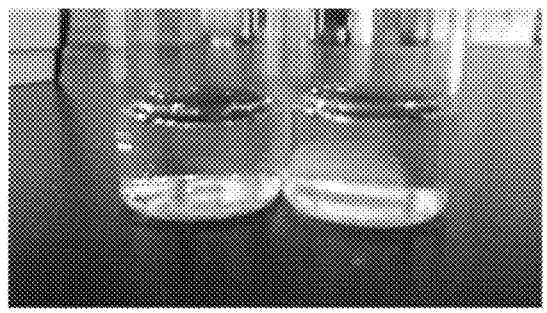
FIG. 2A shows fluorescence at pH 2 (left) and pH 10 (right) of the dye prepared by Preparation Example 12.
Figure 2B:
FIG. 2B shows fluorescence upon UV irradiation at pH 2 (left) and pH 10 (right) of the dye prepared by Preparation Example 12.

FIG. 2A shows fluorescence at pH 2 (left) and pH 10 (right) of the dye prepared by Preparation Example 12, and FIG. 2B shows fluorescence upon UV irradiation at pH 2 (left) and pH 10 (right) of the dye prepared by Preparation Example 12

Referring to FIG. 2, it could be confirmed that the intensity of fluorescence was changed with respect to the change in pH of the dye. In particular, it could be confirmed that stronger fluorescence intensity was provided under basic conditions.

In particular, it could be appreciated that the change in fluorescence intensity of the dye was significantly increased in the range of pH 4 to 9. This pH range was similar to the pH range of cells in the living body, etc. Accordingly, the dye may be efficiently used for confirming pH detection in vivo and confirming change in cells in the living body and processes.

Experimental Example 2. Evaluation of Fluorescence Properties of Film Including Dye In order to investigate the sensitivity to pH detection and the stability of the film manufactured by Example 1, a phosphate buffer solution having a pH of 4 to 8 was prepared by adding 1N hydrochloric acid or sodium hydroxide solution to 0.1 M phosphate buffer solution.

In addition, the film manufactured by Example 1 was supported on 96 wells of a plate, and fluorescence values generated at an excitation wavelength of 454 nm and an emission wavelength of 520 nm were measured using the phosphate buffer solution having a pH of 4 to 8 in the wells.

Figure 3:
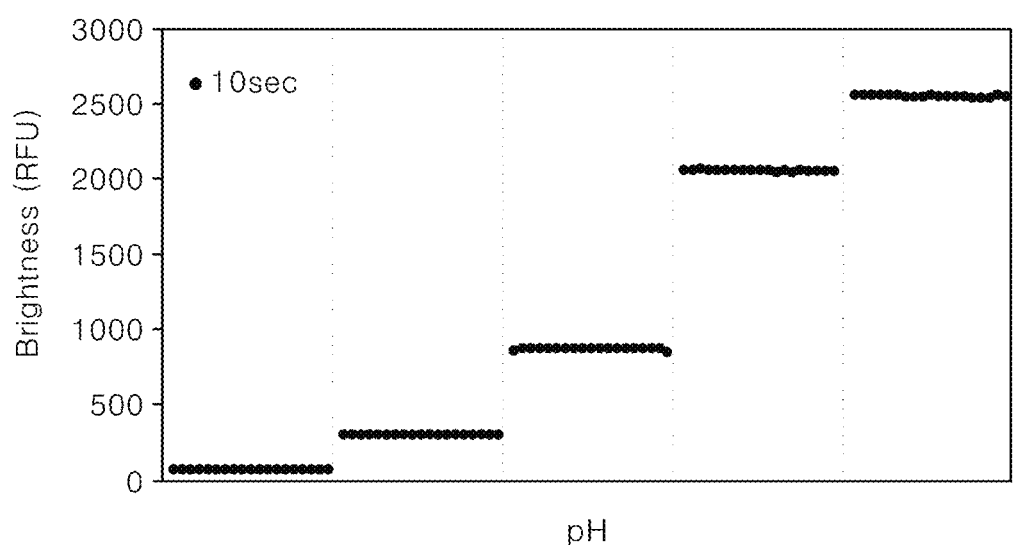
FIG. 3 is a graph showing pH sensitivity measured every 10 seconds of a film manufactured by Example 1.

Here, the fluorescence values were measured 20 times after 10 seconds using a Thermo Scientific VariosKan® Flash, and the results are shown in FIG. 3.

As could be appreciated from the results shown in the drawing, the film manufactured according to the present disclosure had a remarkable difference in fluorescence brightness in the range of pH. In other words, the film had a numerical value similar to the fluorescence brightness according to the pH range of the dye of the present disclosure, and thus it could be appreciated that the film including the dye also maintained high sensitivity to the change in pH as it was, and the film was also stable.

Further, it could be appreciated that since the fluorescence brightness of the film was remarkably different according to the change in pH even in 10 seconds, the sensitivity was very excellent. In addition, the film had the same fluorescence value every measurement for 20 times, and thus it could be confirmed that the dye in the film was kept very stable in the film.

Further, in order to investigate the sensitivity to pH detection and the stability of the films manufactured by Examples 2 and 3, a phosphate buffer solution having a pH of 4 to 9 was prepared by adding 1N hydrochloric acid or sodium hydroxide solution to 0.1 M phosphate buffer solution.

In addition, the films manufactured by Examples 2 and 3 were supported on 96 wells of a plate, and fluorescence values generated at an excitation wavelength of 454 nm and an emission wavelength of 520 nm were measured using the phosphate buffer solution having a pH of 4 to 8 in the wells. The results are shown in Table 2 (Example 2), Table 3 (Example 3), FIG. 4 (Example 2), and FIG. 5 (Example 3).

Figure 4:
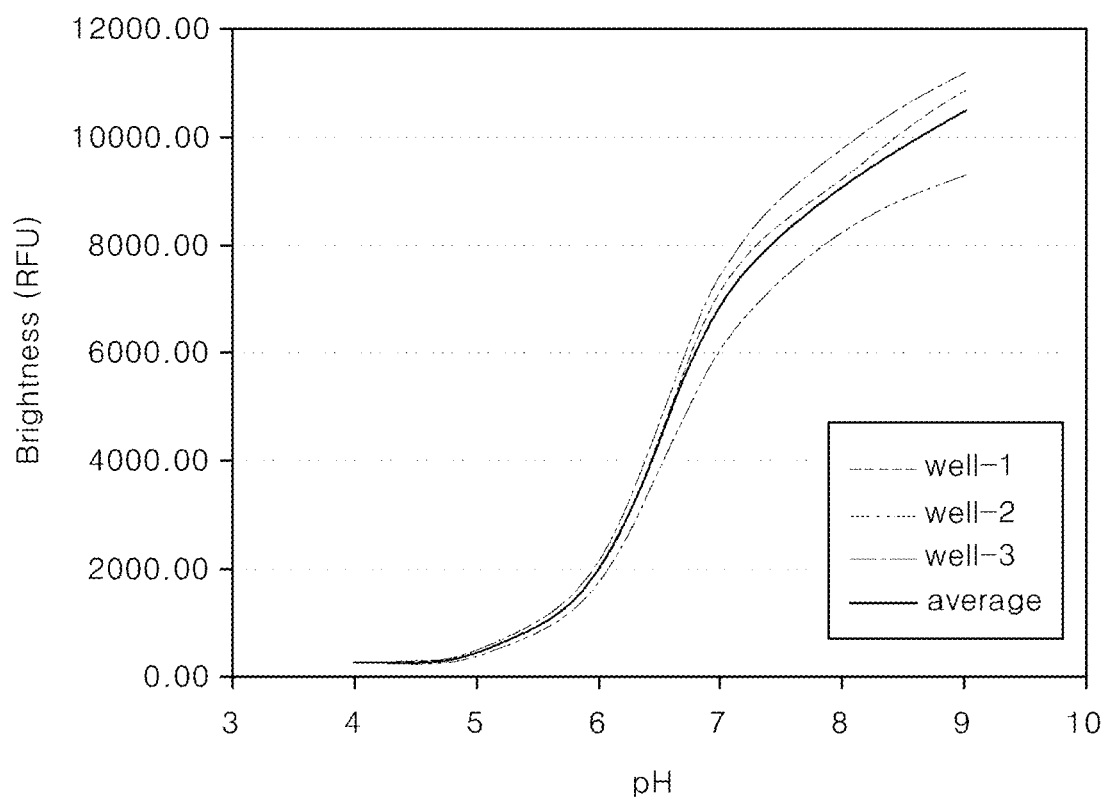
FIG. 4 shows sensitivity (brightness) according to the change in pH of a film manufactured by Example 2.
Figure 5:
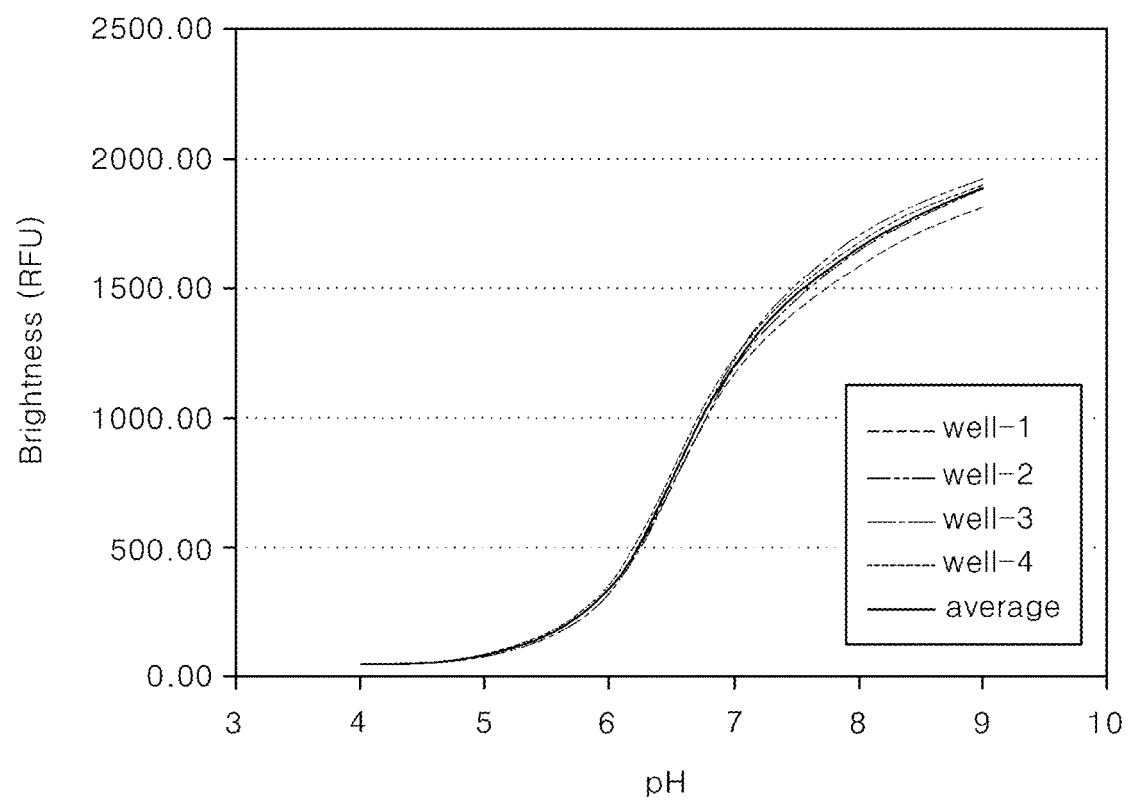
FIG. 5 shows sensitivity (brightness) according to the change in pH of a film manufactured by Example 3.

Referring to the results of Table 2, Table 3, FIG. 4 and FIG. 5, it could be confirmed that the fluorescence properties were slightly different depending on the manner of coating the dye on the surface of the nitrocellulose membrane. However, it was confirmed that a deviation of each well was ±15% or less in Example 2, and the deviation of each well was ±5% or less in Example 3.

TABLE 2

| Classi-fication | Fluorescence Intensity | | | | | |
|---|---|---|---|---|---|---|
| | pH 4 | pH 5 | pH 6 | pH 7 | pH 8 | pH 9 |
| well-1 | 263.17 | 483.78 | 2027.74 | 7097.48 | 9249.37 | 10873.00 |
| well-2 | 232.05 | 404.21 | 1781.65 | 6070.75 | 8237.87 | 9332.00 |
| well-3 | 288.98 | 516.51 | 2180.23 | 7449.86 | 9789.89 | 11212.00 |
| Average | 261.40 | 468.17 | 1996.54 | 6872.70 | 9092.38 | 10472.33 |
| Minimum Deviation | −9.54 | −9.36 | −8.43 | −7.75 | −7.12 | −6.60 |
| Maximum Deviation | 12.65 | 15.82 | 12.06 | 13.21 | 10.37 | 12.22 |

TABLE 3

| Classi-fication | Fluorescence Intensity | | | | | |
|---|---|---|---|---|---|---|
| | pH 4 | pH 5 | pH 6 | pH 7 | pH 8 | pH 9 |
| well-1 | 48.73 | 82.10 | 328.54 | 1170.17 | 1587.07 | 1824.70 |
| well-2 | 48.82 | 86.49 | 350.90 | 1243.18 | 1699.78 | 1927.92 |
| well-3 | 46.99 | 82.15 | 332.20 | 1196.20 | 1646.81 | 1887.39 |
| Well-4 | 48.14 | 88.81 | 355.40 | 1223.98 | 1676.56 | 1899.04 |
| Average | 48.17 | 84.89 | 341.76 | 1208.38 | 1652.56 | 1884.76 |
| Minimum Deviation | −1.33 | −4.41 | −3.84 | −2.80 | −2.78 | −2.24 |
| Maximum Deviation | 2.50 | 3.40 | 4.03 | 3.27 | 4.13 | 3.29 |

Therefore, the dye according to the present disclosure could be efficiently used to simultaneously measure the pH of a plurality of samples in the form of a film.

Experimental Example 3. Evaluation of Fluorescence Properties of Plate Coated with Dye In order to investigate the sensitivity to pH detection and the stability of the plate manufactured by Example 4, a phosphate buffer solution having a pH of 4 to 8 was prepared by adding 1N hydrochloric acid or sodium hydroxide solution to 0.1 M phosphate buffer solution.

Figure 6:
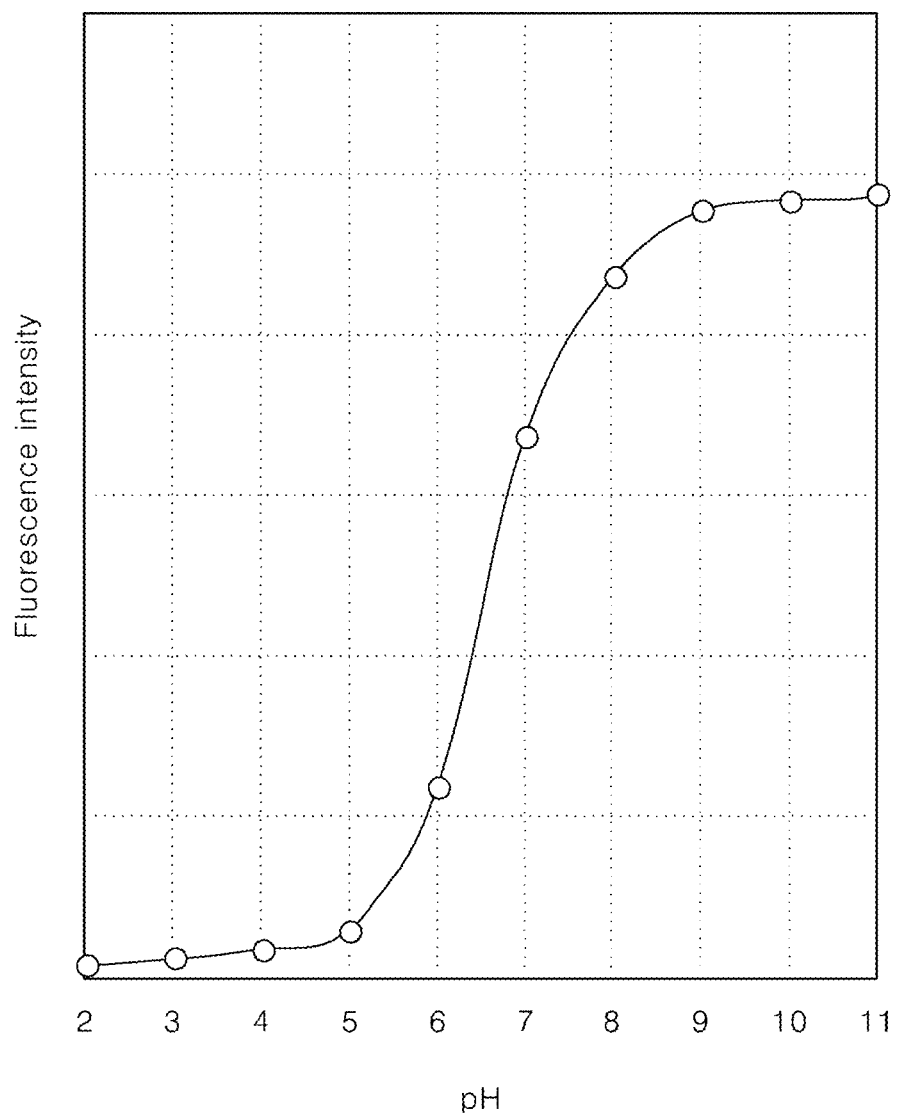
FIG. 6 is a graph showing fluorescence intensity according to the change in pH of a plate prepared by Example 4.
Figure 7:
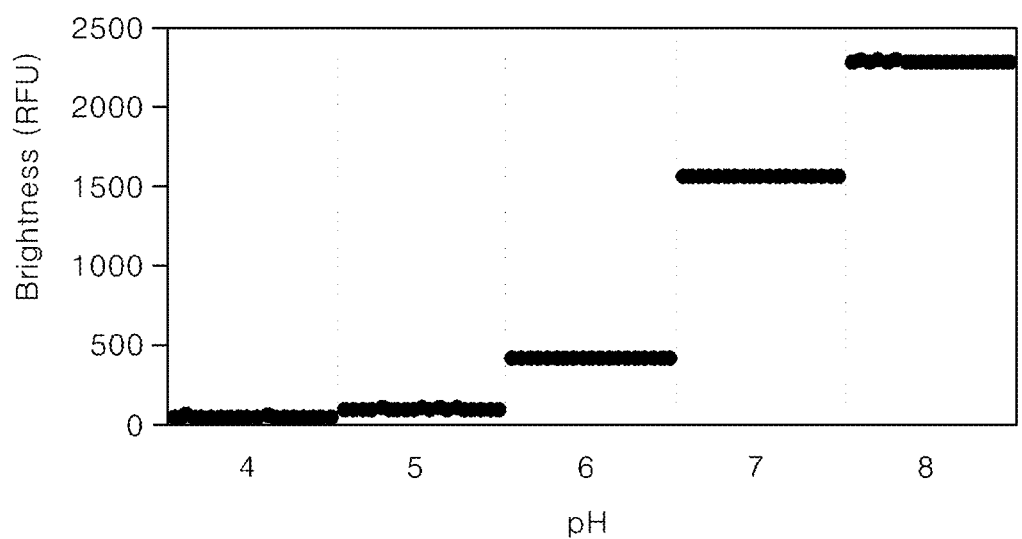
FIG. 7 shows sensitivity (brightness) according to the change in pH of the plate manufactured by Example 4.

In addition, the fluorescence values generated at an excitation wavelength of 454 nm and an emission wavelength of 520 nm were measured by a reader (Thermo Scientific VariosKan® Flash) in 96 wells of the plate manufactured by Example 4, using the phosphate buffer solution having a pH of 4 to 8. The results are shown in FIG. 6. The fluorescence values (brightness) were measured 20 times at intervals of 2 seconds, and the results are shown in FIG. 7.

Similar to the film, the measured fluorescence showed a significant difference in fluorescence brightness in the in vivo pH range. In addition, the fluorescence values were the same as or similar to each other every measurement for 20 times, and thus it could be confirmed that the dye was coated very stably.

In addition, it could be confirmed that the coating of the dye remained bonded to the plate without breaks even though a separate coating film was absent. Further, it could be confirmed that high sensitivity to the change in pH of the dye was maintained as it was.

Accordingly, the dye may be used not only to measure pH by penetration into living cells but also to measure pH of cells through a plate reader, and may be used in various application fields for measuring pH.

Further, fluorescence values generated at the excitation wavelength of 454 nm and the emission wavelength of 520 nm in the plates manufactured by Example 5 and Example 6 instead of the plate manufactured by Example 4 were measured by a reader (Thermo Scientific VariosKan® Flash) using the same method as described above.

Figure 8:
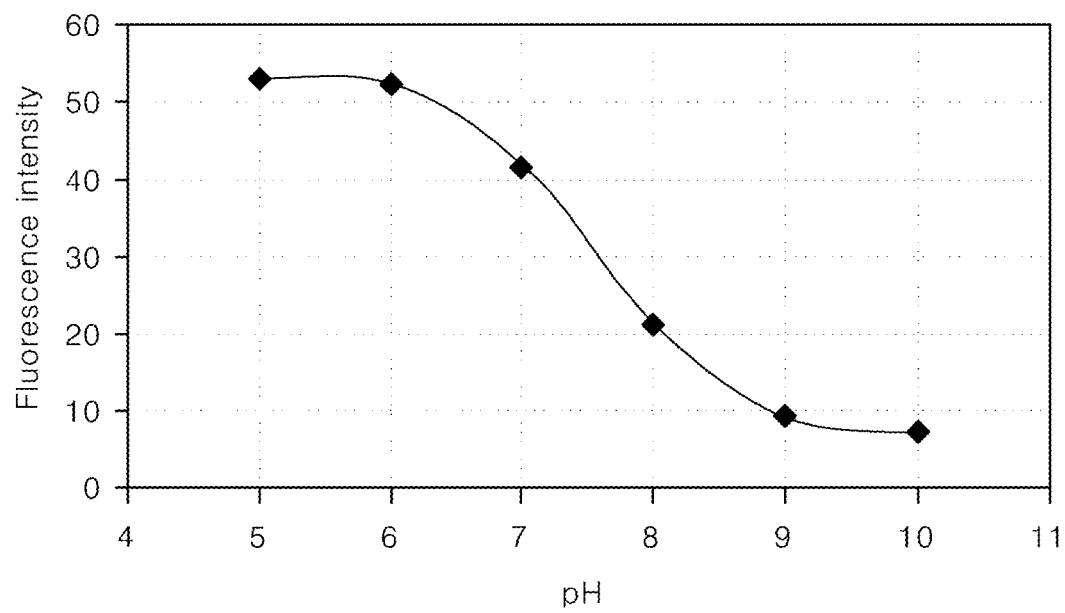
FIG. 8 is a graph showing fluorescence intensity according to the change in pH of a plate prepared by Example 5.
Figure 9:
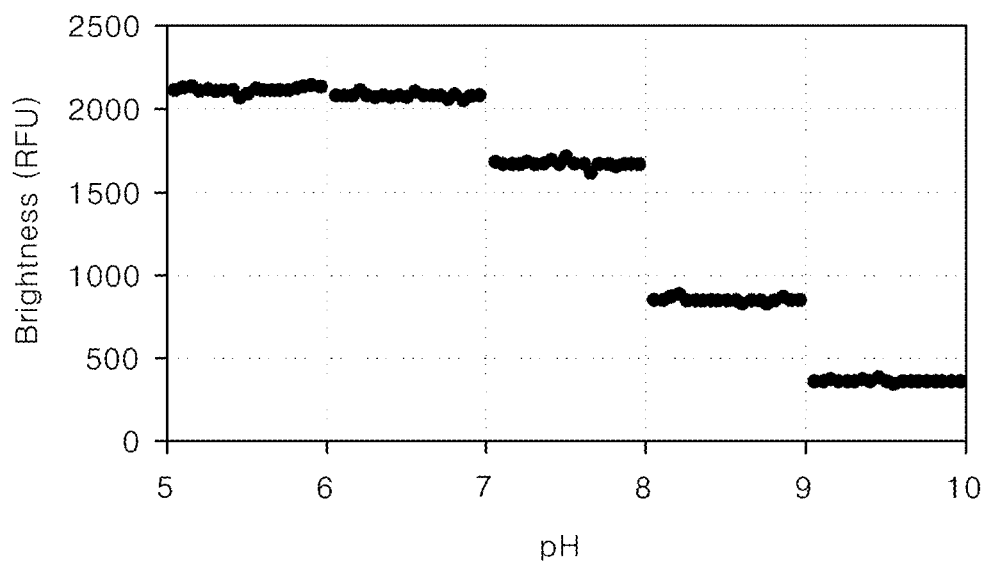
FIG. 9 shows sensitivity (brightness) according to the change in pH of the plate manufactured by Example 5.
Figure 10:
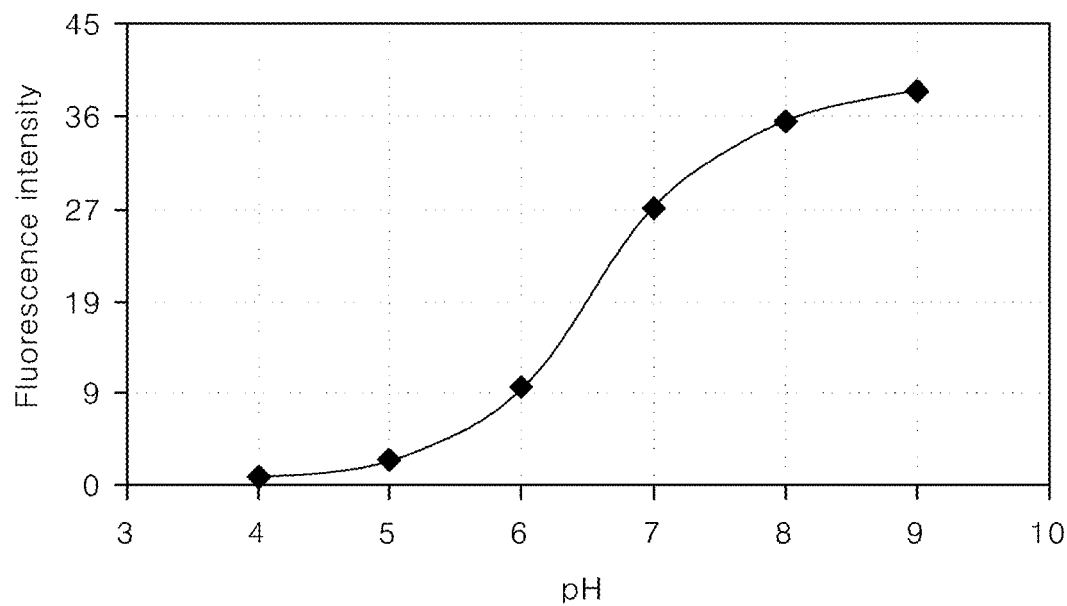
FIG. 10 is a graph showing fluorescence intensity according to the change in pH of a plate manufactured by Example 6.
Figure 11:
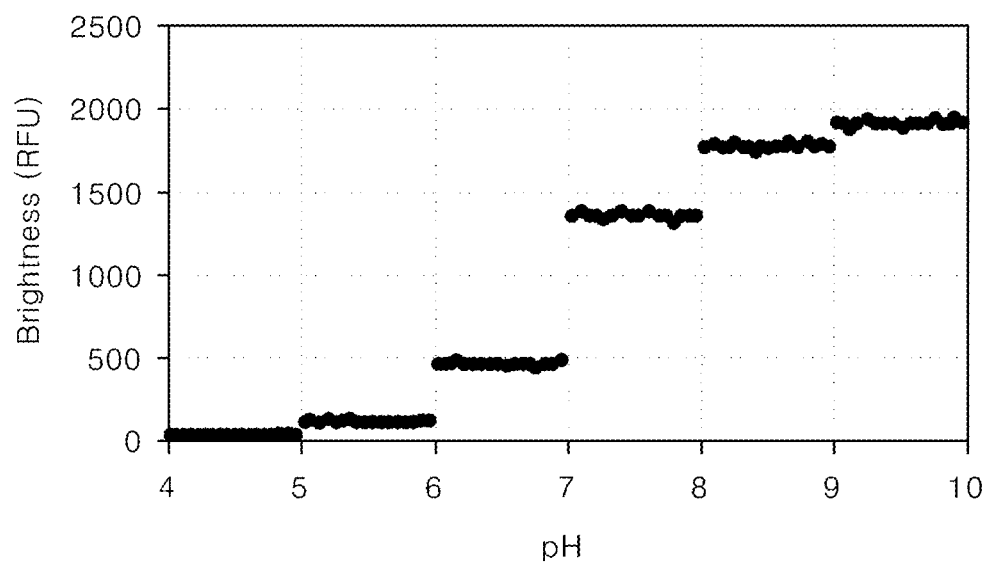
FIG. 11 shows sensitivity (brightness) according to the change in pH of the plate manufactured by Example 6.

The results for the plate manufactured by Example 5 are shown in FIGS. 8 and 9, and the results for the plate manufactured by Example 6 are shown in FIGS. 10 and 11.

Experimental Example 4. Evaluation of Resistance to Buffer Solution of Dye

In order to confirm the resistance to buffer solution of the dye prepared by Preparation Example 12, 5 µl of the dye was supported in one well of the plate and dried at 60° C.

In addition, the phosphate buffer solution having a pH of 4 to 8 was supported in the wells, and the fluorescence values generated at an excitation wavelength of 454 nm and an emission wavelength of 520 nm were measured by using the phosphate buffer solution. Here, the fluorescence values were measured 20 times at intervals of 2 seconds using a reader (Thermo Scientific VariosKan® Flash).

Here, the measurement was sequentially performed by supporting the phosphoric acid buffer solution of pH 4 in one well, performing the measurement, washing 5 times with distilled water, and supporting the phosphoric acid buffer solution of pH 5 again, performing the measurement, etc. The results are shown in FIG. 12.

Figure 12:
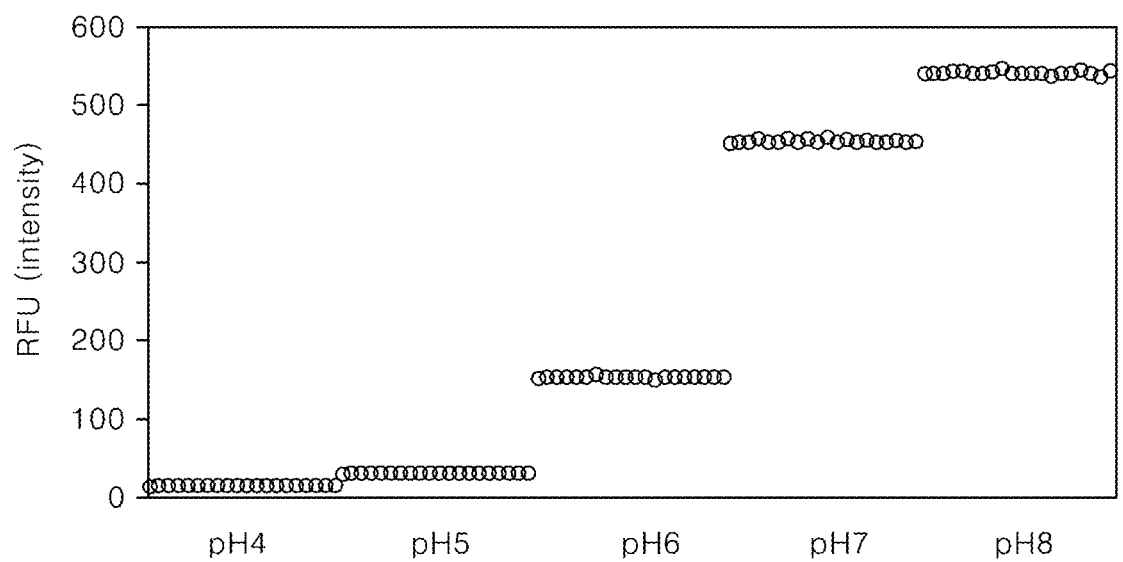
FIG. 12 is a graph showing pH sensitivity (brightness) measured with respect to a buffer solution of the dye of Preparation Example 12.

Referring to FIG. 12, it could be appreciated that the dye prepared according to the present disclosure showed a remarkable difference in fluorescence brightness in the above-described pH range. The above pH range corresponded to the in vivo pH range, and thus it could be appreciated that the dye prepared by Preparation Example 12 is suitable for detecting the change in pH in vivo.

In addition, the dye prepared by Preparation Example 12 showed predetermined fluorescence values according to each pH even though it was measured in one well, and thus it could be confirmed that the dye was very stable with respect to the buffer solution.

Figure 13:
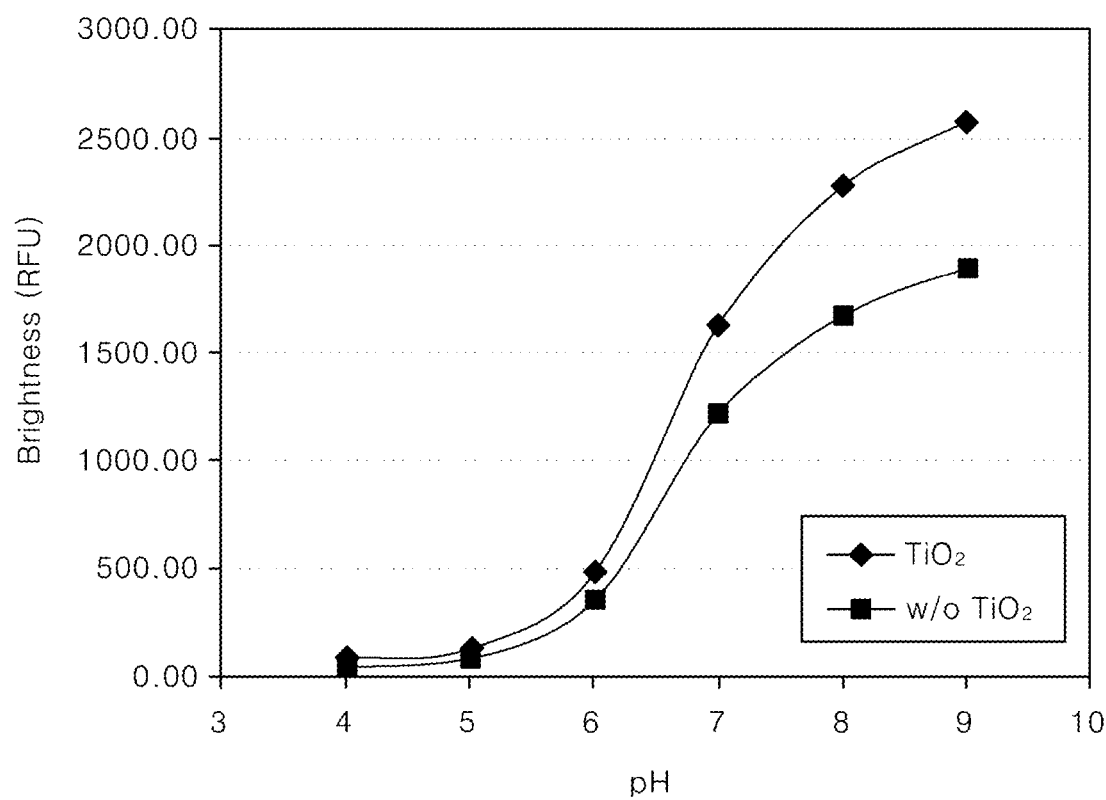
FIG. 13 shows sensitivity (brightness) according to the change in pH of a film manufactured by Example 3 and a film manufactured by Example 7.

Experimental Example 5. Evaluation of Fluorescence Properties of Film Including $TiO_2$ Reflective Layer Referring to Table 4 and FIG. 13 showing the results of evaluating the pH sensitivity of the film manufactured by Example 3 and the film manufactured by Example 7, it could be confirmed that when the $TiO_2$ reflective layer was included, the fluorescence intensity was improved by about 20 to 30%.

TABLE 4

| Classi-fication | Fluorescence Intensity | | | | | |
|---|---|---|---|---|---|---|
| | pH 4 | pH 5 | pH 6 | pH 7 | pH 8 | pH 9 |
| Example 6 | 79.41 | 131.31 | 485.73 | 1630.33 | 2279.26 | 2576.68 |
| Example 3 | 48.14 | 88.81 | 355.40 | 1223.98 | 1676.56 | 1899.04 |

Figure 14:
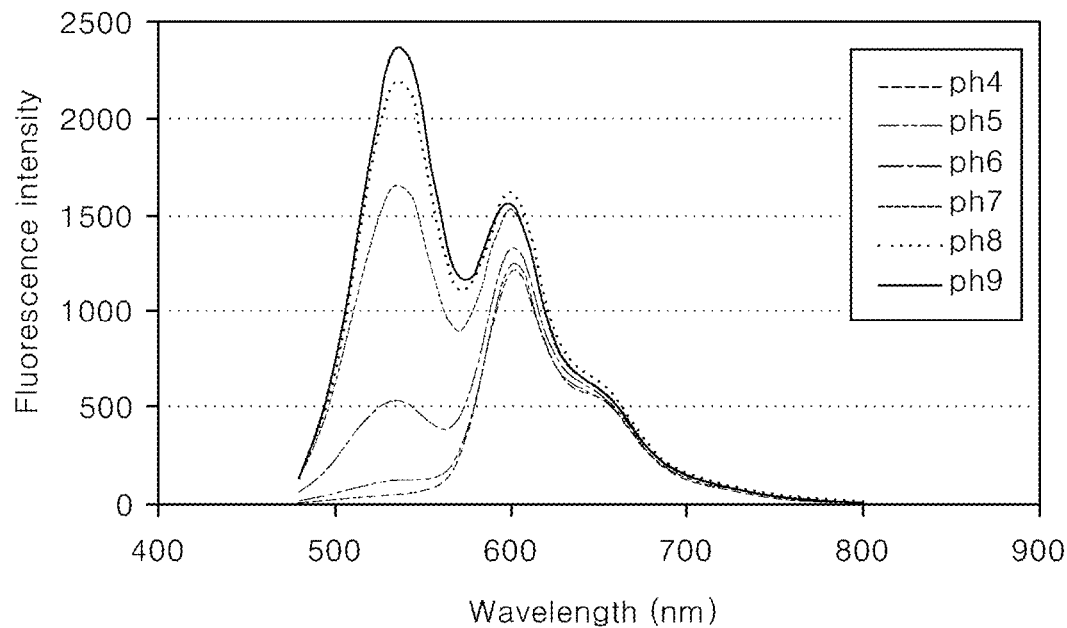
FIG. 14 shows emission spectrum results according to the change in pH of a film manufactured by Example 8.
Figure 15:
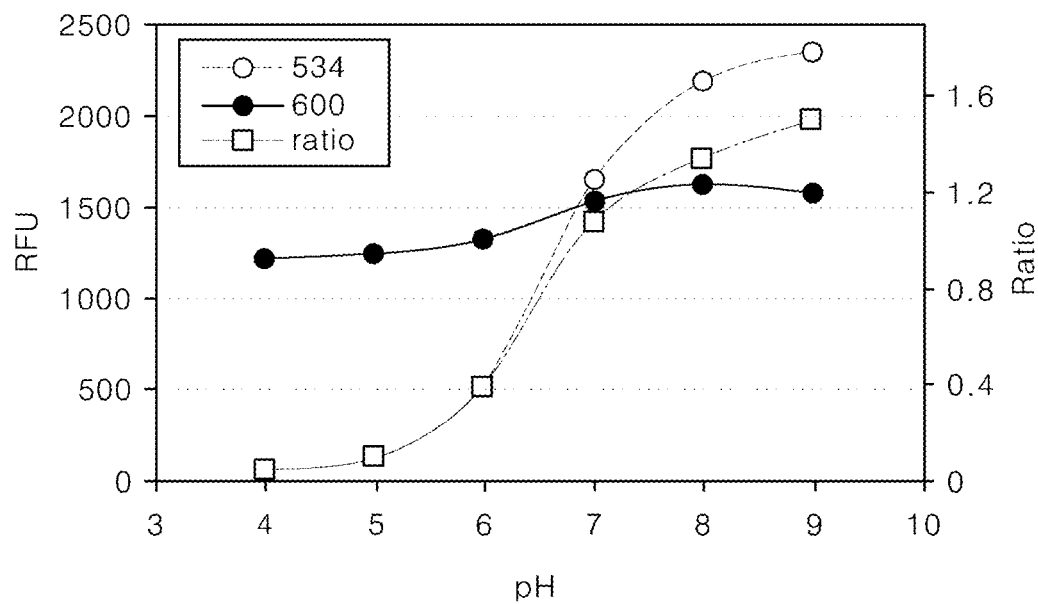
FIG. 15 shows sensitivity (brightness) and a ratio according to the change in pH of the film manufactured by Example 8, wherein 534 represents the fluorescence intensity according to the change in pH at 534 nm, 600 represents the fluorescence intensity according to the change in pH at 600 nm, and the ratio is a calculation value of the fluorescence intensity according to the change in pH at 534 nm/the fluorescence intensity according to the change in pH at 600 nm.
Figure 16:
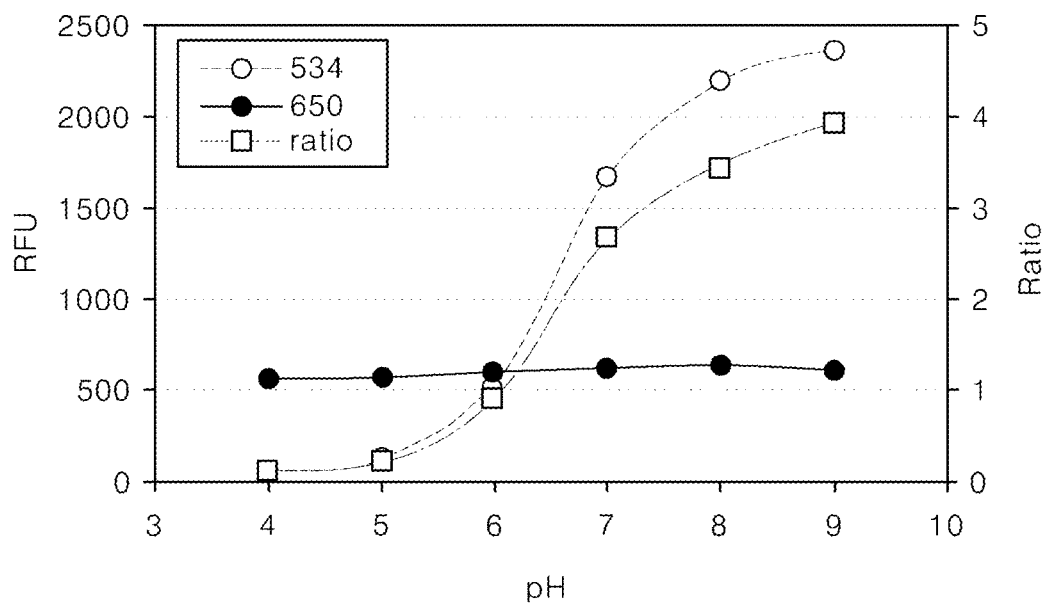
FIG. 16 shows sensitivity (brightness) and a ratio according to the change in pH of the film manufactured by Example 8, wherein 534 represents the fluorescence intensity according to the change in pH at 534 nm, 650 represents the fluorescence intensity according to the change in pH at 650 nm, and the ratio is a calculation value of the fluorescence intensity according to the change in pH at 534 nm/the fluorescence intensity according to the change in pH at 650 nm.
Figure 17:
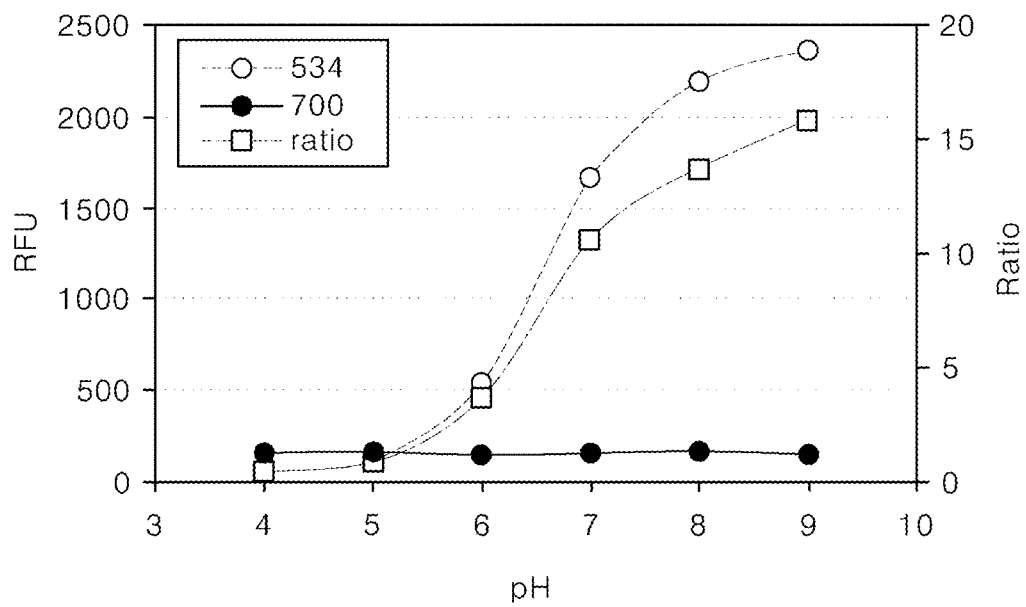
FIG. 17 shows sensitivity (brightness) and a ratio according to the change in pH of the film manufactured by Example 8, wherein 534 represents the fluorescence intensity according to the change in pH at 534 nm, 700 represents the fluorescence intensity according to the change in pH at 700 nm, and the ratio is a calculation value of the fluorescence intensity according to the change in pH at 534 nm/the fluorescence intensity according to the change in pH at 700 nm.
Figure 18:
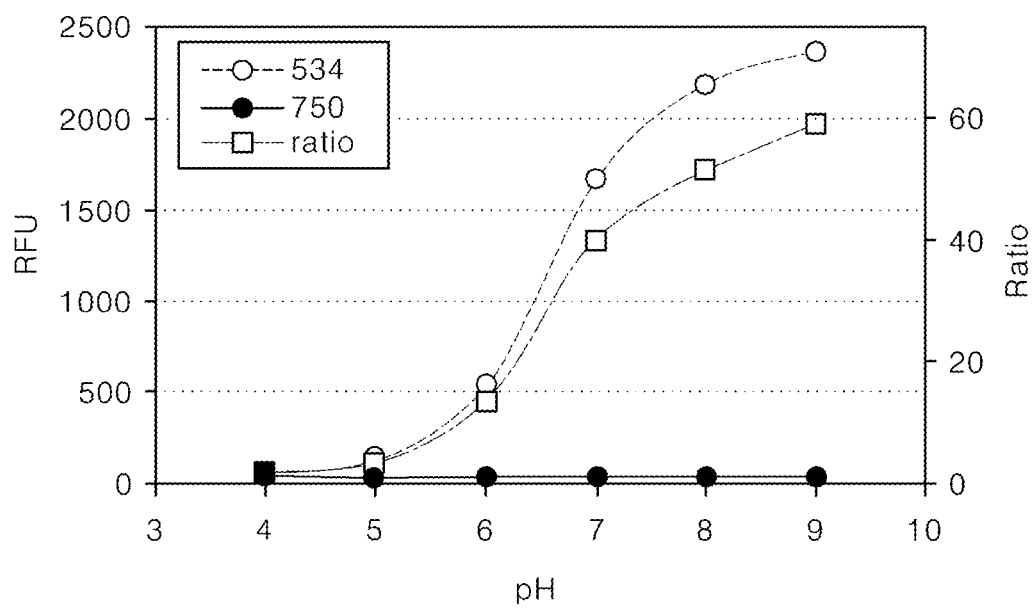
FIG. 18 shows sensitivity (brightness) and a ratio according to the change in pH of the film manufactured by Example 8, wherein 534 represents the fluorescence intensity according to the change in pH at 534 nm, 750 represents the fluorescence intensity according to the change in pH at 750 nm, and the ratio is a calculation value of the fluorescence intensity according to the change in pH at 534 nm/the fluorescence intensity according to the change in pH at 750 nm.

Experimental Example 6. Evaluation of Characteristic of Film Including Reference Dye The film manufactured by Example 8 was adhered to the plate so that the film coated with the reference dye faced a light source, the plate was put into a reader (Thermo Scientific VariosKan® Flash) using the phosphate buffer solution having a pH of 4 to 9, and the emission spectrum was measured at an excitation wavelength of 454 nm. The results are shown in FIG. 14.

The emission spectrum values according to the change in pH at the wavelengths of 534 nm, 600 nm, 650 nm, 700 nm and 750 nm are shown, and the sensitivities (brightness) according to the change in pH are shown in FIG. 15 to FIG. 18. Further, the ratio calculated by the fluorescence intensity according to the change in pH at 534 nm/the fluorescence intensity according to the change in pH at each wavelength (600, 650, 700, and 750 nm) is shown in FIG. 15 to FIG. 18.

(For reference, 534 nm is the light emission wavelength of the dye prepared by Preparation Example 12, 600 nm is the light emission wavelength of the reference dye used in Example 8, and the results are shown up to 650, 700, 750 nm in the order of decreasing wavelength overlap)

It could be confirmed from FIG. 15 to FIG. 18 that even though the ratio values were different from each other, the change in fluorescence intensity was shown as a substantially constant pattern with the change in fluorescence intensity of the film manufactured by Example 8 Therefore, if a predetermined pattern of ratio value is known, it is possible to directly obtain accurate measurement data without performing fluorescence calibration according to pH, and thus a number of advantages in time for preparing measurement, accuracy and reliability of data, etc., may be provided.

The fluorogenic pH-sensitive dye according to the present disclosure may exhibit excellent sensitivity to the change in pH to thereby be suitable for in-vivo pH detection, may have excellent resistance to buffer solutions, etc., to exhibit excellent stability at the time of manufacturing the dye into the film. Thus, the fluorogenic pH-sensitive dye according to the present disclosure may be effectively used as the kit for detecting pH, the film, etc., including the dye.

The present disclosure described above may be variously substituted, altered, and modified by those skilled in the art to which the present disclosure pertains without departing from the scope and sprit of the present disclosure. Therefore, the present disclosure is not limited to the above-mentioned exemplary embodiments and the accompanying drawings.

What is claimed is:

1. A fluorogenic pH-sensitive dye comprising:
   an aryl compound having a sulfonyl group (—$SO_2$); and
   an agarose compound covalently bonded to the sulfonyl group (—$SO_2$) of the aryl compound,
   wherein the aryl compound having the sulfonyl group (—$SO_2$) is derived from an aryl compound having a sulfonate (—$SO_3Ra$) group, and Ra is an anion, hydrogen or a substituent; and
   wherein the aryl compound and the agarose compound are directly covalently bonded using the sulfonate group as a linker.

2. The fluorogenic pH-sensitive dye of claim 1, wherein the agarose compound has a structure represented by Chemical Formula 1 below, and
   at least one R in the Chemical Formula 1 is present at a position covalently bonded to the sulfonyl group (—$SO_2$) of the aryl compound;

[Chemical Formula 1]

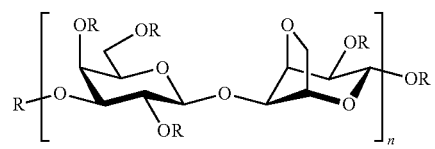

wherein, in Chemical Formula 1, n is an integer of 5 or more.

3. The fluorogenic pH-sensitive dye of claim 1, wherein the aryl compound having the sulfonate (—SO$_3$Ra) group includes a compound represented by Chemical Formula 2 below:

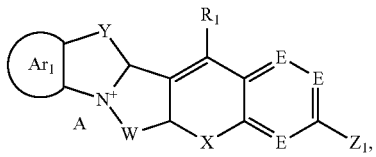

[Chemical Formula 2]

wherein, in Chemical Formula 2, at least one of Ar$_1$, Y, W, R$_1$, E, X and Z$_1$ has a sulfonate (—SO$_3$Ra) group, and the Ra is an anion, a hydrogen or a substituent, Ar$_1$ is substituted or unsubstituted aryl having 6 to 20 carbon atoms or substituted or unsubstituted heteroaryl having 2 to 20 carbon atoms, E is CR$_1$ or N, Z$_1$ is NR$_2$R$_3$, OR$_4$, or SR$_5$, X is O, S, NR$_8$R$_9$, SiR$_{10}$R$_{11}$, CR$_{12}$R$_{13}$ or Se, Y is CR$_{14}$R$_{15}$, NR$_{16}$, O, S, Se, SiR$_{17}$R$_{18}$ or CR$_{19}$R$_{20}$=CR$_{21}$R$_{22}$, W is CR$_{23}$R$_{24}$, CR$_{25}$R$_{26}$=CR5$_{27}$R$_{28}$, O, —[CR$_{29}$R$_{30}$—CR$_{31}$R$_{32}$]— or —[CR$_{33}$R$_{34}$—O]—, R$_{23}$ to R$_{34}$ are the same as or different from each other and each independently hydrogen, deuterium, alkyl or acyloxy, R$_1$ to R$_{22}$ and R$_{29}$ to R$_{41}$ are the same as or different from each other, and each independently any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, and A is an organic ion or an inorganic ion, and is present as an anion or a cation or is absent.

4. The fluorogenic pH-sensitive dye of claim 1, wherein the aryl compound having a sulfonate (—SO$_3$Ra) group includes a compound represented by Chemical Formula 3 below:

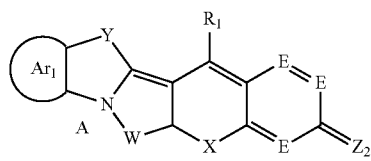

[Chemical Formula 3]

wherein, in Chemical Formula 3, at least one of Ar$_1$, Y, W, R$_1$, E, X and Z$_2$ has a sulfonate (—SO$_3$Ra) group, and the Ra is an anion, a hydrogen or a substituent, Ar$_1$ is substituted or unsubstituted aryl having 6 to 20 carbon atoms or substituted or unsubstituted heteroaryl having 2 to 20 carbon atoms, E is CR$_1$ or N, Z$_2$ is NR$_6$, O, S, or O+R$_7$, X is O, S, NR$_8$R$_9$, SiR$_{10}$R$_{11}$, CR$_{12}$R$_{13}$ or Se, Y is CR$_{14}$R$_{15}$, NR$_{16}$, O, S, Se, SiR$_{17}$R$_{18}$ or CR$_{19}$R$_{20}$=CR$_{21}$R$_{22}$, W is CR$_{23}$R$_{24}$, CR$_{25}$R$_{26}$=CR5$_{27}$R$_{28}$, O, —[CR$_{29}$R$_{30}$—CR$_{31}$R$_{32}$]— or —[CR$_{33}$R$_{34}$—O]—, R$_{23}$ to R$_{34}$ are the same as or different from each other and each independently hydrogen, deuterium, alkyl or acyloxy, R$_1$ to R$_{22}$ and R$_{29}$ to R$_{41}$ are the same as or different from each other, and each independently any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium, and A is an organic ion or an inorganic ion, and may be present as an anion or a cation or may be absent.

5. The fluorogenic pH-sensitive dye of claim 1, wherein the aryl compound having a sulfonate (—SO$_3$Ra) group includes a compound represented by Chemical Formula 4 below:

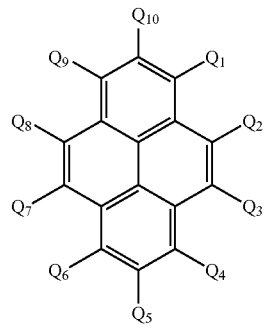

[Chemical Formula 4]

wherein, in Chemical Formula 4, at least one of Q1 to Q10 has a sulfonate (—SO$_3$Ra) group, at least one of Q1 to Q10 that do not have the sulfonate (—SO$_3$Ra) group has a hydroxyl group (—OH), and Q1 to Q10 that do not have the sulfonate (—SO$_3$Ra) group and the hydroxyl group (—OH) are hydrogen, deuterium or a substituent.

6. A film for detecting pH comprising:
the fluorogenic pH-sensitive dye of claim 1 on a polymer film.

7. A film for detecting pH comprising:
a first sub-film including the fluorogenic pH-sensitive dye of claim 1 on a polymer film; and
a second sub-film including a dye exhibiting light emission at a different wavelength band at the same pH as the fluorogenic pH-sensitive dye.

8. A method for coating a fluorogenic pH-sensitive dye comprising:
heating the fluorogenic pH-sensitive dye of claim 1 to form a solution; and
dropping the solution into each well of a plate, followed by gelling.

9. A method for detecting pH or disease in a sample comprising:
contacting the sample with the fluorogenic pH-sensitive dye of claim 1;
incubating the sample in contact with the fluorogenic pH-sensitive dye to form a cultured sample;
irradiating the cultured sample with light to emit light; and
detecting fluorescence emission from the sample.

10. The fluorogenic PH-sensitive dye of claim 3, wherein:
the $Ar_1$ is substituted with at least one substituent, respectively, and the at least one substituent is any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

11. The fluorogenic PH-sensitive dye of claim 10, wherein:
the at least one substituent is any one selected from alkyl, alkenyl, alkynyl, aryl, heteroaryl, arylalkyl, aryloxy, aryloxyalkyl, alkoxy and alkoxyalkyl, and the at least one substituent is further substituted with at least one further substituent selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

12. The fluorogenic PH-sensitive dye of claim 3, wherein:
two adjacent to each other of $R_{23}$ to $R_{34}$ are linked to form an alicyclic hydrocarbon.

13. The fluorogenic PH-sensitive dye of claim 3, wherein:
two of $R_1$ to $R_3$ and substituents adjacent thereto are linked to each other to form an alicyclic hydrocarbon ring, a monocyclic aromatic hydrocarbon ring or a polycyclic aromatic hydrocarbon ring, and at least one carbon atom of the formed alicyclic or aromatic hydrocarbon ring may be substituted with any one selected from N, S, O, Se, Te, Po, $NR_{35}$, $SiR_{36}R_{37}$, $GeR_{38}R_{39}$, $PR_{40}$, and $BR_{41}$.

14. The fluorogenic PH-sensitive dye of claim 3, wherein:
at least one of $R_1$ to $R_{22}$ and $R_{29}$ to $R_{41}$ is any one selected from alkyl, alkenyl, alkynyl, aryl, heteroaryl, arylalkyl, aryloxy, aryloxyalkyl, alkoxy and alkoxyalkyl, and is further substituted with at least one substituent selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

15. The fluorogenic PH-sensitive dye of claim 4, wherein:
the $Ar_1$ is substituted with at least one substituent, respectively, and the at least one substituent is any one selected from hydrogen, deuterium, substituted or unsubstituted alkyl, substituted or unsubstituted alkenyl, substituted or unsubstituted alkynyl, substituted or unsubstituted aryl, substituted or unsubstituted heteroaryl, substituted or unsubstituted arylalkyl, substituted or unsubstituted aryloxy, substituted or unsubstituted aryloxyalkyl, substituted or unsubstituted alkoxy, substituted or unsubstituted alkoxyalkyl, halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

16. The fluorogenic PH-sensitive dye of claim 15, wherein:
the at least one substituent is any one selected from alkyl, alkenyl, alkynyl, aryl, heteroaryl, arylalkyl, aryloxy, aryloxyalkyl, alkoxy and alkoxyalkyl, and is further substituted with at least one further substituent selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

17. The fluorogenic PH-sensitive dye of claim 4, wherein:
two adjacent to each other of $R_{23}$ to $R_{34}$ are linked to form an alicyclic hydrocarbon.

18. The fluorogenic PH-sensitive dye of claim 4, wherein:
two of $R_1$ to $R_3$ and substituents adjacent thereto are linked to each other to form an alicyclic hydrocarbon ring, a monocyclic aromatic hydrocarbon ring or a polycyclic aromatic hydrocarbon ring, and at least one carbon atom of the formed alicyclic or aromatic hydrocarbon ring is substituted with any one selected from N, S, O, Se, Te, Po, $NR_{35}$, $SiR_{36}R_{37}$, $GeR_{38}R_{39}$, $PR_{40}$, and $BR_{41}$.

19. The fluorogenic PH-sensitive dye of claim 4, wherein:
at least one of $R_1$ to $R_{22}$ and $R_{29}$ to $R_{41}$ is any one selected from alkyl, alkenyl, alkynyl, aryl, heteroaryl, arylalkyl, aryloxy, aryloxyalkyl, alkoxy and alkoxyalkyl, and is further substituted with at least one substituent selected from halogen, cyano, nitro, amine, hydroxy, aldehyde, amino, amide, hydrazine, thiol, acetal, ketal, phosphoryl, phosphate, phosphonate, sulfohydroxy, sulfonyl, sulfonate, sulfate, carboxylate, amide, azido, guanidinium, carbonyl, thiocarbonyl, aminothiocarbonyl, carboxyl, carboxylic acid, ketone, sulfhydryl, acyl chloride, sulfonic acid, ester, polyalkylene oxide, polyethylene glycol, and quaternary ammonium.

* * * * *